United States Patent
Axten et al.

(10) Patent No.: US 10,851,053 B2
(45) Date of Patent: Dec. 1, 2020

(54) CHEMICAL COMPOUNDS

(71) Applicant: GlaxoSmithKline Intellectual Property Development Limited, Brentford (GB)

(72) Inventors: Jeffrey Michael Axten, Collegeville, PA (US); Mui Cheung, Collegeville, PA (US); Anthony William Dean, Stevenage (GB); Michael P. DeMartino, Collegeville, PA (US); Hilary Schenck Eidam, Collegeville, PA (US); Biswajit Kalita, Bangalore (IN); Raghava Reddy Kethiri, Bangalore (IN); Rajendra Kristam, Bangalore (IN)

(73) Assignee: GlaxoSmithKline Intellectual Property Development Limited, Brentford (GB)

( * ) Notice: Subject to any disclaimer, the term of this patent is extended or adjusted under 35 U.S.C. 154(b) by 0 days.

(21) Appl. No.: 16/307,513

(22) PCT Filed: Jun. 7, 2017

(86) PCT No.: PCT/IB2017/053370
§ 371 (c)(1),
(2) Date: Dec. 6, 2018

(87) PCT Pub. No.: WO2017/212423
PCT Pub. Date: Dec. 14, 2017

(65) Prior Publication Data
US 2019/0144384 A1     May 16, 2019

(30) Foreign Application Priority Data

Jun. 8, 2016  (IN) .............................. 201611019696

(51) Int. Cl.
*A61K 31/403*     (2006.01)
*A61K 31/4025*   (2006.01)
(Continued)

(52) U.S. Cl.
CPC ............ *C07D 207/26* (2013.01); *A61P 25/00* (2018.01); *A61P 35/00* (2018.01); *C07D 207/09* (2013.01);
(Continued)

(58) Field of Classification Search
CPC .............. A61K 31/403; A61K 31/4025; A61K 31/4015; A61K 31/44; A61K 31/4439;
(Continued)

(56) References Cited

U.S. PATENT DOCUMENTS

| 5,100,901 A | 3/1992 | Sugimoto et al. |
| 2002/0035103 A1* | 3/2002 | Bennani .............. C07D 207/12 514/210.18 |

(Continued)

FOREIGN PATENT DOCUMENTS

| EP | 1179341 A1 * | 2/2002 | ......... A61K 31/4155 |
| EP | 1179341 A1 | 2/2002 | |

(Continued)

OTHER PUBLICATIONS

Golub et al., "Molecular classification of Cancer: class discovery and class prediction by gene expression monitoring" Science (1999), 286 (5439), pp. 531-537. (Year: 1999).*

(Continued)

*Primary Examiner* — Matthew P Coughlin
*Assistant Examiner* — Sagar Patel
(74) *Attorney, Agent, or Firm* — Nora L. Stein; Fang Qian; Kathryn Lutomski

(57) ABSTRACT

The invention is directed to substituted pyrrolidine derivatives. Specifically, the invention is directed to compounds according to Formula III:

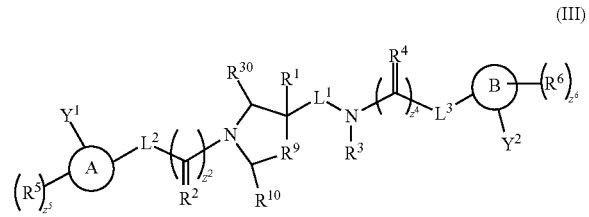

(III)

wherein A, B, $L^1$, $L^2$, $L^3$, $R^1$, $R^2$, $R^3$, $R^4$, $R^5$, $R^6$, $R^9$, $R^{10}$, $R^{30}$, $Y^1$, $Y^2$, $z^2$, $z^4$, $z^5$, and $z^6$ are as defined herein, and salts thereof.

The compounds of the invention are inhibitors of the ATF4 pathway and can be useful in the treatment of cancer, pre-cancerous syndromes and diseases associated with activated unfolded protein response pathways, such as Alzheimer's disease, spinal cord injury, traumatic brain injury, ischemic stroke, stroke, diabetes, Parkinson disease, Huntington's disease, Creutzfeldt-Jakob Disease, and related prion diseases, progressive supranuclear palsy, amyotrophic lateral sclerosis, myocardial infarction, cardiovascular disease, inflammation, fibrosis, chronic and acute diseases of the liver, chronic and acute diseases of the lung, chronic and acute diseases of the kidney, chronic traumatic encephalopathy (CTE), neurodegeneration, dementia, cognitive impairment, atherosclerosis, ocular diseases, arrhythmias, in organ transplantation and in the transportation of organs for transplantation. Accordingly, the invention is further directed to pharmaceutical compositions comprising a compound of the invention. The invention is still further (Continued)

directed to methods of inhibiting the ATF4 pathway and treatment of disorders associated therewith using a compound of the invention or a pharmaceutical composition comprising a compound of the invention.

4 Claims, No Drawings

(51) Int. Cl.

| | |
|---|---|
| A61K 31/4015 | (2006.01) |
| A61K 31/44 | (2006.01) |
| A61K 31/4439 | (2006.01) |
| C07D 209/52 | (2006.01) |
| C07D 207/26 | (2006.01) |
| C07D 207/09 | (2006.01) |
| C07D 401/06 | (2006.01) |
| C07D 401/12 | (2006.01) |
| C07D 401/14 | (2006.01) |
| A61P 25/28 | (2006.01) |
| A61P 25/00 | (2006.01) |
| A61P 35/00 | (2006.01) |
| C07D 487/10 | (2006.01) |
| C07D 405/06 | (2006.01) |
| C07D 405/12 | (2006.01) |
| C07D 487/04 | (2006.01) |

(52) U.S. Cl.
CPC ......... *C07D 209/52* (2013.01); *C07D 401/06* (2013.01); *C07D 405/06* (2013.01); *C07D 405/12* (2013.01); *C07D 487/04* (2013.01); *C07D 487/10* (2013.01)

(58) Field of Classification Search
CPC .. C07D 209/52; C07D 207/26; C07D 207/09; C07D 401/06; C07D 401/12; C07D 401/14; A61P 25/28; A61P 25/00; A61P 35/00
USPC ........ 514/414, 422, 424; 548/515, 468, 467, 548/518
See application file for complete search history.

(56) References Cited

U.S. PATENT DOCUMENTS

| | | |
|---|---|---|
| 2004/0053986 A1 | 3/2004 | Bjorsne et al. |
| 2005/0234034 A1 | 10/2005 | Pennell et al. |
| 2006/0019985 A1 | 1/2006 | Ma et al. |
| 2008/0207648 A1 | 8/2008 | Fairhurst et al. |
| 2012/0041001 A1 | 2/2012 | Van Emelen et al. |
| 2015/0266862 A1 | 9/2015 | Sherer et al. |
| 2016/0096800 A1 | 4/2016 | Walter et al. |

FOREIGN PATENT DOCUMENTS

| | | | | |
|---|---|---|---|---|
| WO | WO 2008/150231 A1 | 12/2008 | | |
| WO | WO-2013019561 A1 | * 2/2013 | ........... | C07D 401/12 |
| WO | WO 2013/065712 A1 | 5/2013 | | |

OTHER PUBLICATIONS

Lala et al., "Role of nitric oxide in tumor progression: Lessons from experimental tumors" Cancer and Metastasis Reviews (1998), 17: pp. 91-106. (Year: 1998).*
Sedeyn, J., H. Wu, R. Hobbs, E. Levin, R. Nagele and V. Venkataraman, "Histamine Induces Alzheimer's Disease-Like Blood Brain Barrier Breach and Local Cellular Responses in Mouse Brain Organotypic Cultures" Biomed. Res. Inter. (2015), 2015: pp. 1-12. (Year: 2015).*
Avivar-Valderas A, et al., *PERK integrates autophagy and oxidative stress responses to promote survival during extracellular matrix detachment.* Mol Cel Biol 31:3616-3629 (2011).
Axten JM., et al., *Discovery of 7-methy-5(I-( [3-10 (trifluoromethyl)phenyl]acetyl)-2, 3-dihydro-IH-indo1-5yl)-7H-pyrrolo [2, 3-d]pyrimidin-4 amine (GSK2606414), a potent and selective first-in class inhibitor of protein kinase R (PKR)-like endplasmic reticulum kinase (PERK),* J. Med. Chem. 55(16):7193-7207 (2012).
Bi M, et al., *ER stress-regulated translation increases tolerance to extreme hypoxia and promotes tumor growth.* EMBO J. 24:3470-3481 (2005).
Bobrovnikova-Marjon E, et al., *PERK promotes cancer cell proliferation and tumor growth by limiting oxidative DNA damage.* Oncogene 29: 3881-3895 (2010).
Borck G., et al., *eIF2y mutation that disrupts eIF2 complex integrity links intellectual disability to impaired translation 30 initiation.* Mol Cell 48:1-6 (2012).
Costa-Mattioli, et al., *Translational control of hippocampal synaptic plasticity and memory by the eIF2n kinase GCN2.* Nature 436:1166-1173 (2005).
Costa-Mattioli, et al., *eIF2n phosphorylation bidirectionally regulates the switch from short to long term synaptic plasticity and memory.* Cell 25 129: 195-206 (2007).
Database Registry [Online], Chemical Abstracts Service, Columbus, Ohio, US; Sep. 29, 2015, XP002772525, Database accession No. 1808577-76-5 abstract.
Fritz, et al., *Efficient Synthesis of Cyclopropane-Fused Heterocycles with Bromethylsulfonium Salt,* Chemistry—A European Journal, 19(33):10827-10831 (2013).
Gardner BM, et al., *Unfolded proteins are Ire1-activating ligands that directly induce the unfolded protein response. Science.,* 333(6051):1891-4 (2011).
Harding HP, et al., *Perk is essential for translational regulation and cell survival during the unfolded protein response. Mol Cell.,* 5(5):897-904 (2000).
Harding, et al., *Regulated translation initiation controls stress-induced gene expression in mammalian cells. Mol. Cell.,* 6(5):1099-108 (2000).
Hearn et al., *Structure-Activity Studies of Bis-O-Arylglycolamides: Inhibitors of the Integrated Stress Response,* ChemMedChem, 11(8):870-880 (2016).
Hinnebusch AG, *Translational regulation of GCN4 and the general amino acid control of yeast. Annu. Rev. Microbiol.* 59:407-50 (2005).
Hinnebusch, et al., *The mechanism of eukaryotic translation initiation: new insights and challenges. Cold Spring Harb Perspect Biol.,* 4(10) (2012).
Jackson RJ, et al., *The mechanism of eukaryotic translation initiation and principles of its regulation. Nat Rev Mol Cell Biol.,* I I(2):113-27 (2010).
Krishnamoorthy, et al., *Tight binding of the phosphorylated alpha subunit of initiation factor 2 (eIF2alpha) to the regulatory subunits of guanine nucleotide exchange factor eIF2B is required for inhibition of translation initiation. Mol Cell Biol.,* 21(15):5018-30 (2001).
Ma Y, et al., *Two distinct stress signaling pathways converge upon the CHOP promoter during the mammalian unfolded protein response.* J. Mol. Biol., 318(5):1351-65 (2002).
Mikami S., et al., *An efficient mammalian cell-free translation system supplemented with translation factors. Protein Expr. Purif.,* 46:348-357 (2006).
Moreno JA, et al., *Sustained translational repression by eIF2n-P mediates prion neurodegeneration,* Nature, 485:507-511 (2012).
Palam LR, et al., *Phosphorylation of eIF2 facilitates ribosomal bypass of an inhibitory upstream ORF to enhance CHOP translation, Journal of Biological Chemistry,* 2011 286(13):10939-49 (2011).
Pavitt GD, et al, *Protein synthesis and its control in neuronal cells with a focus on vanishing white matter disease. Biochem Soc Trans,* 37:1298-20 1310 (2009).

(56) References Cited

OTHER PUBLICATIONS

Pavitt GD, et al., *New insights into translational regulation in the endoplasmic reticulum unfolded protein response. Cold Spring Harb Perspect Biol.*, Jun;4(6) 2012.
Ron D, et al., *Signal integration in the endoplasmic reticulum unfolded protein response. Nat Rev Mol Cell Biol.*, Jul;8(7):519-29 (2007).
Rotstein, et al., Novel hexahydropyrrolo[3,4-c]pyrrole CCR5 antagonists, *Bioorg. Med. Chem. Letters*, 20(10):3116-3119 (2010).
Shore GCG, Papa FRF, Oakes SAS. *Signaling cell death from the endoplasmic reticulum stress response. Current Opinion in Cell Biology.*, Apr. 1;23(2):143-9 (2011).
Tabas I, Ron D. *Integrating the mechanisms of apoptosis induced by endoplasmic reticulum stress. Nat Cell Biol*, Mar. I;13(3):184-90 (2011).
Vattern KM, *Reinitiation involving upstream ORFs regulates ATF4 mRNA translation in mammalian cells. Proc Natl Acad Sci USA*, Aug. 3;101(31):11269-74 (2004).
Walter P, et al., *The unfolded protein response: from stress pathway to homeostatic regulation. Science*, Nov. 25;334(6059):1081-6 (2011).
Wek RR, et al., *Coping with stress: eIF2 kinases and translational control. Biochem. Soc. Trans.*, Feb;34(Pt I):7-11 (2006).
Ye J., et al., *The GCN2—ATF4 pathway is critical for tumour cell survival and proliferation in response to nutrient deprivation. EMBO J.* 29: 2082-2096 (2010).
Zeenko V., et al., *An efficient in vitro translation system from mammalian cell lacking translational inhibition caused by eIF2 phosphorylation. RNA* 14: 593-602 (2008).
Zhu P. J, et al., *Suppression of PKR promotes network excitability and enhanced cognition by interferon-7-mediated disinhibition, Cell*, 147: 1384-1396 (2011).

* cited by examiner

CHEMICAL COMPOUNDS

This application is a 371 of International Application No. PCT/IB2017/053370, filed 7 Jun. 2017, which claims priority to IN 201611019696, filed 8 Jun. 2016.

FIELD OF THE INVENTION

The present invention relates to substituted pyrrolidine derivatives that are inhibitors of the ATF4 pathway. The present invention also relates to pharmaceutical compositions comprising such compounds and methods of using such compounds in the treatment of diseases/injuries associated with activated unfolded protein response pathways, such as cancer, pre-cancerous syndromes, Alzheimer's disease, spinal cord injury, traumatic brain injury, ischemic stroke, stroke, diabetes, Parkinson disease, Huntington's disease, Creutzfeldt-Jakob Disease, and related prion diseases, progressive supranuclear palsy, amyotrophic lateral sclerosis, myocardial infarction, cardiovascular disease, inflammation, fibrosis, chronic and acute diseases of the liver, chronic and acute diseases of the lung, chronic and acute diseases of the kidney, chronic traumatic encephalopathy (CTE), neurodegeneration, dementia, cognitive impairment, atherosclerosis, ocular diseases, arrhythmias, in organ transplantation and in the transportation of organs for transplantation.

BACKGROUND OF THE INVENTION

In metazoa, diverse stress signals converge at a single phosphorylation event at serine 51 of a common effector, the translation initiation factor eIF2α. This step is carried out by four eIF2α kinases in mammalian cells: PERK, which responds to an accumulation of unfolded proteins in the endoplasmic reticulum (ER), GCN2 to amino acid starvation and UV light, PKR to viral infection, and HRI to heme deficiency. This collection of signaling pathways has been termed the "integrated stress response" (ISR), as they converge on the same molecular event. eIF2α phosphorylation results in an attenuation of translation with consequences that allow cells to cope with the varied stresses (1).

eIF2 (which is comprised of three subunits, α, β, and γ) binds GTP and the initiator Met-tRNA to form the ternary complex (eIF2-GTP-Met-tRNAi), which, in turn, associates with the 40S ribosomal subunit scanning the 5'UTR of mRNAs to select the initiating AUG codon. Upon phosphorylation of its a-subunit, eIF2 becomes a competitive inhibitor of its GTP-exchange factor (GEF), eIF2B (2). The tight and nonproductive binding of phosphorylated eIF2 to eIF2B prevents loading of the eIF2 complex with GTP thus blocking ternary complex formation and reducing translation initiation (3). Because eIF2B is less abundant than eIF2, phosphorylation of only a small fraction of the total eIF2 has a dramatic impact on eIF2B activity in cells.

Paradoxically, under conditions of reduced protein synthesis, a small group of mRNAs that contain upstream open reading frames (uORFs) in their 5'UTR are translationally up-regulated (4,5). These include mammalian ATF4 (a cAMP element binding (CREB) transcription factor) and CHOP (a pro-apoptotic transcription factor) (6-8). ATF4 regulates the expression of many genes involved in metabolism and nutrient uptake and additional transcription factors, such as CHOP, which is under both translational and transcriptional control (9). Phosphorylation of eIF2α thus leads to preferential translation of key regulatory molecules and directs diverse changes in the transcriptome of cells upon cellular stress.

One of the eIF2α kinases, PERK, lies at the intersection of the ISR and the unfolded protein response (UPR) that maintains homeostasis of protein folding rates in the ER (10). The UPR is activated by unfolded or misfolded proteins that accumulate in the ER lumen because of an imbalance between protein folding load and protein folding capacity, a condition known as "ER stress". In mammals, the UPR is comprised of three signaling branches mediated by ER-localized transmembrane sensors, PERK, IRE1, and ATF6. These sensor proteins detect the accumulation of unfolded protein in the ER and transmit the information across the ER membrane, initiating unique signaling pathways that converge in the activation of an extensive transcriptional response, which ultimately results in ER expansion (11). The lumenal stress-sensing domains of PERK and IRE1 are homologous and likely activated in analogous ways by direct binding to unfolded peptides (12). This binding event leads to oligomerization and trans-autophosphorylation of their cytosolic kinase domains, and, for PERK, phosphorylation of its only known substrate, eIF2α. In this way, PERK activation results in a quick reduction in the load of newly synthesized proteins that are translocated into the ER-lumen (13).

Upon ER stress, both the transcription factor XBP1s, produced as the consequence of a non-conventional mRNA splicing reaction initiated by IRE1, and the transcription factor ATF6, produced by proteolysis and release from the ER membrane, collaborate with ATF4 to induce the vast UPR transcriptional response. Transcriptional targets of the UPR include the ER protein folding machinery, the ER-associated degradation machinery, and many other components functioning in the secretory pathway (14). Although the UPR initially mitigates ER stress and as such confers cytoprotection, persistent and severe ER stress leads to activation of apoptosis that eliminates damaged cells (15, 16).

Small-molecule therapeutics that inhibit the UPR and/or the Integrated Stress Response could be used in cancer as a single agent or in combination with other chemotherapeutics (17, 18, 19), for enhancement of long-term memory (24,25), in neurodegenerative and prion associated diseases (20), in white matter disease (VWM) (23) and in biotechnology applications that would benefit from increased protein translation.

It is an object of the instant invention to provide novel compounds that prevent the translation of ATF4 or are inhibitors of the ATF4 pathway.

It is also an object of the present invention to provide pharmaceutical compositions that comprise a pharmaceutically acceptable excipient and compounds of Formula (III).

It is also an object of the present invention to provide a method for treating neurodegenerative diseases, cancer, and other diseases/injuries associated with activated unfolded protein response pathways such as: Alzheimer's disease, spinal cord injury, traumatic brain injury, ischemic stroke, stroke, diabetes, Parkinson disease, Huntington's disease, Creutzfeldt-Jakob Disease, and related prion diseases, amyotrophic lateral sclerosis, progressive supranuclear palsy, myocardial infarction, cardiovascular disease, inflammation, fibrosis, chronic and acute diseases of the liver, chronic and acute diseases of the lung, chronic and acute diseases of the kidney, chronic traumatic encephalopathy (CTE), neurodegeneration, dementias, atherosclerosis, ocular diseases, arrhythmias, in organ transplantation and in the transportation of organs for transplantation that comprises administering novel inhibitors of the ATF4 pathway.

SUMMARY OF THE INVENTION

The invention is directed to substituted pyrrolidine derivatives. Specifically, the invention is directed to compounds according to Formula III:

(III)

$$\text{[chemical structure]}$$

wherein A, B, $L^1$, $L^2$, $L^3$, $R^1$, $R^2$, $R^3$, $R^4$, $R^5$, $R^6$, $R^9$, $R^{10}$, $R^{30}$, $Y^1$, $Y^2$, $z^2$, $z^4$, $z^5$, and $z^6$ are as defined below; or a salt thereof including a pharmaceutically acceptable salt thereof.

The present invention also relates to the discovery that the compounds of Formula (III) are active as inhibitors of the ATF4 pathway.

The present invention also relates to the discovery that the compounds of Formula (III) prevent the translation of ATF4.

This invention also relates to a method of treating Alzheimer's disease, which comprises administering to a subject in need thereof an effective amount of a compound of Formula (III) or a pharmaceutically acceptable salt thereof.

This invention also relates to a method of treating Parkinson's disease, which comprises administering to a subject in need thereof an effective amount of a compound of Formula (III) or a pharmaceutically acceptable salt thereof.

This invention also relates to a method of treating amyotrophic lateral sclerosis, which comprises administering to a subject in need thereof an effective amount of a compound of Formula (III) or a pharmaceutically acceptable salt thereof.

This invention also relates to a method of treating Huntington's disease, which comprises administering to a subject in need thereof an effective amount of a compound of Formula (III) or a pharmaceutically acceptable salt thereof.

This invention also relates to a method of treating Creutzfeldt-Jakob Disease, which comprises administering to a subject in need thereof an effective amount of a compound of Formula (III) or a pharmaceutically acceptable salt thereof.

This invention also relates to a method of treating progressive supranuclear palsy (PSP), which comprises administering to a subject in need thereof an effective amount of a compound of Formula (III) or a pharmaceutically acceptable salt thereof.

This invention also relates to a method of treating dementia, which comprises administering to a subject in need thereof an effective amount of a compound of Formula (III) or a pharmaceutically acceptable salt thereof.

This invention also relates to a method of treating spinal cord injury, which comprises administering to a subject in need thereof an effective amount of a compound of Formula (III) or a pharmaceutically acceptable salt thereof.

This invention also relates to a method of treating traumatic brain injury, which comprises administering to a subject in need thereof an effective amount of a compound of Formula (III) or a pharmaceutically acceptable salt thereof.

This invention also relates to a method of treating ischemic stroke, which comprises administering to a subject in need thereof an effective amount of a compound of Formula (III) or a pharmaceutically acceptable salt thereof.

This invention also relates to a method of treating diabetes, which comprises administering to a subject in need thereof an effective amount of a compound of Formula (III) or a pharmaceutically acceptable salt thereof.

This invention also relates to a method of treating a disease state selected from: myocardial infarction, cardiovascular disease, atherosclerosis, ocular diseases, and arrhythmias, which comprises administering to a subject in need thereof an effective amount of a compound of Formula (III) or a pharmaceutically acceptable salt thereof.

This invention also relates to a method of treating an integrated stress response-associated disease in a patient in need of such treatment, the method including administering a therapeutically effective amount of a compound of Formula (III) or a pharmaceutically acceptable salt thereof, to the patient.

This invention also relates to a method of treating a disease associated with phosphorylation of eIF2α in a patient in need of such treatment, the method including administering a therapeutically effective amount of a compound of Formula (III), or a pharmaceutically acceptable salt thereof, to the patient.

This invention also relates to a method of treating a disease in a patient in need of such treatment, the method including administering a therapeutically effective amount of a compound of Formula (III) or a pharmaceutically acceptable salt thereof, to the patient, wherein the disease is selected from the group consisting of cancer, a neurodegenerative disease, vanishing white matter disease, childhood ataxia with CNS hypomyelination, and an intellectual disability syndrome.

This invention also relates to a method of improving long-term memory in a patient, the method including administering a therapeutically effective amount of a compound of Formula (III) or a pharmaceutically acceptable salt thereof, to the patient.

This invention also relates to a method of increasing protein expression of a cell or in vitro expression system, the method including administering an effective amount of a compound of Formula (III) or a pharmaceutically acceptable salt thereof, to the cell or expression system.

This invention also relates to a method of treating an inflammatory disease in a patient in need of such treatment, the method including administering a therapeutically effective amount of a compound of Formula (III), or a pharmaceutically acceptable salt thereof, to the patient.

This invention also relates to a method of using the compounds of Formula (III) in organ transplantation and in the transportation of organs for transplantation.

Also included in the present invention are methods of co-administering the presently invented compounds with further active ingredients.

Included in the present invention is a method for treating neurodegenerative diseases, cancer, and other diseases/injuries associated with activated unfolded protein response pathways such as: Alzheimer's disease, spinal cord injury, traumatic brain injury, ischemic stroke, stroke, diabetes, Parkinson disease, Huntington's disease, Creutzfeldt-Jakob Disease, and related prion diseases, amyotrophic lateral sclerosis, progressive supranuclear palsy, myocardial infarction, cardiovascular disease, inflammation, fibrosis, chronic and acute diseases of the liver, chronic and acute diseases of the lung, chronic and acute diseases of the kidney, chronic traumatic encephalopathy (CTE), neurodegeneration, dementias, atherosclerosis, ocular diseases, arrhythmias, in organ transplantation and in the transportation of organs for transplantation that comprises administering the compounds of Formula (III).

The invention also relates to a compound of Formula (III) or a pharmaceutically acceptable salt thereof for use in therapy.

The invention also relates to a compound of Formula (III) or a pharmaceutically acceptable salt thereof for use in the treatment of Alzheimer's disease.

The invention also relates to a compound of Formula (III) or a pharmaceutically acceptable salt thereof for use in the treatment of Parkinson's disease syndromes.

The invention also relates to a compound of Formula (III) or a pharmaceutically acceptable salt thereof for use in the treatment of amyotrophic lateral sclerosis.

The invention also relates to a compound of Formula (III) or a pharmaceutically acceptable salt thereof for use in the treatment of Huntington's disease.

The invention also relates to a compound of Formula (III) or a pharmaceutically acceptable salt thereof for use in the treatment of Creutzfeldt-Jakob Disease.

The invention also relates to a compound of Formula (III) or a pharmaceutically acceptable salt thereof for use in the treatment of progressive supranuclear palsy (PSP).

The invention also relates to a compound of Formula (III) or a pharmaceutically acceptable salt thereof for use in the treatment of dementia.

The invention also relates to a compound of Formula (III) or a pharmaceutically acceptable salt thereof for use in the treatment of spinal cord injury.

The invention also relates to a compound of Formula (III) or a pharmaceutically acceptable salt thereof for use in the treatment of traumatic brain injury.

The invention also relates to a compound of Formula (III) or a pharmaceutically acceptable salt thereof for use in the treatment of ischemic stroke.

The invention also relates to a compound of Formula (III) or a pharmaceutically acceptable salt thereof for use in the treatment of diabetes.

The invention also relates to a compound of Formula (III) or a pharmaceutically acceptable salt thereof for use in the treatment of a disease state selected from: myocardial infarction, cardiovascular disease, atherosclerosis, ocular diseases, and arrhythmias.

The invention also relates to the use of a compound of Formula (III) or a pharmaceutically acceptable salt thereof in the manufacture of a medicament for the treatment of an integrated stress response-associated disease.

The invention also relates to the use of a compound of Formula (III) or a pharmaceutically acceptable salt thereof in the manufacture of a medicament for the treatment of a disease associated with phosphorylation of eIF2α.

The invention also relates to the use of a compound of Formula (III) or a pharmaceutically acceptable salt thereof in the manufacture of a medicament for the treatment of a disease selected from the group consisting of: cancer, a neurodegenerative disease, vanishing white matter disease, childhood ataxia with CNS hypomyelination, and an intellectual disability syndrome.

The invention also relates to the use of a compound of Formula (III) or a pharmaceutically acceptable salt thereof in the manufacture of a medicament for improving long-term memory.

The invention also relates to the use of a compound of Formula (III) or a pharmaceutically acceptable salt thereof in the manufacture of a medicament for increasing protein expression of a cell or in vitro expression system.

The invention also relates to the use of a compound of Formula (III) or a pharmaceutically acceptable salt thereof in the manufacture of a medicament for the treatment of inflammatory disease.

The invention also relates to the use of a compound of Formula (III) or a pharmaceutically acceptable salt thereof in the manufacture of a medicament in organ transplantation and in the transportation of organs for transplantation.

The invention also relates to the use of a compound of Formula (III) or a pharmaceutically acceptable salt thereof in the manufacture of a medicament for the treatment of a disease state selected from: neurodegenerative diseases, cancer, and other diseases/injuries associated with activated unfolded protein response pathways such as: Alzheimer's disease, spinal cord injury, traumatic brain injury, ischemic stroke, stroke, diabetes, Parkinson disease, Huntington's disease, Creutzfeldt-Jakob Disease, and related prion diseases, amyotrophic lateral sclerosis, progressive supranuclear palsy, myocardial infarction, cardiovascular disease, inflammation, fibrosis, chronic and acute diseases of the liver, chronic and acute diseases of the lung, chronic and acute diseases of the kidney, chronic traumatic encephalopathy (CTE), neurodegeneration, dementias, atherosclerosis, ocular diseases, arrhythmias, in organ transplantation and in the transportation of organs for transplantation.

Included in the present invention are pharmaceutical compositions that comprise a pharmaceutical excipient and a compound of Formula (III) or a pharmaceutically acceptable salt thereof.

The invention also relates to a pharmaceutical composition as defined above for use in therapy.

The invention also relates to a combination for use in therapy which comprises a therapeutically effective amount of (i) a compound of Formula (III) or a pharmaceutically acceptable salt thereof; and (ii) further active ingredients.

DETAILED DESCRIPTION OF THE INVENTION

Included in the compounds of the invention and used in the methods of the invention are compounds of Formula (III):

(I)

wherein:
X$^1$ and X$^2$ are independently —CH— or —N—;
L$^2$ and L$^3$ are independently a bond, —NH—, —O—, —S—, —S(O)—, —S(O)$_2$—, substituted or unsubstituted C$_{1-6}$alkylene or substituted or unsubstituted C$_{1-6}$heteroalkylene;
L$^1$ is selected from: a bond, —NH—, —C(R$^7$)—, —O—, —S—, —S(O)—, —S(O)$_2$—, substituted or unsubstituted C$_{1-6}$alkylene and substituted or unsubstituted C$_{1-6}$heteroalkylene;
Y$^1$ is hydrogen or is C$_{1-4}$alkyl and taken together with L$^2$ to form a heterocycloalkyl, which is optionally substituted with from 1 to 5 substituents independently selected from:
fluoro, chloro, C$_{1-6}$alkyl, C$_{1-6}$alkyl substituted 1 to 6 times by fluoro, C$_{1-4}$alkoxy, C$_{1-4}$alkoxy substituted 1 to 6 times by fluoro, oxo, and —NH$_2$;
Y$^2$ is hydrogen or is C$_{1-4}$alkyl and taken together with L$^3$ to form a heterocycloalkyl, which is optionally substituted with from 1 to 5 substituents independently selected from:
fluoro, chloro, C$_{1-6}$alkyl, C$_{1-6}$alkyl substituted 1 to 6 times by fluoro, C$_{1-4}$alkoxy, C$_{1-4}$alkoxy substituted 1 to 6 times by fluoro, oxo, and —NH$_2$;
R$^1$ is selected from: hydrogen, C$_{1-6}$alkyl, C$_{1-6}$alkyl substituted 1 to 6 times by fluoro, R$^1$ taken together with R$^3$ and the nitrogen to which R$^3$ is attached, and optionally from 1 to 3 additional heteroatoms, form a heterocycloalkyl, which is optionally substituted with from 1 to 5 substituents independently selected from:
fluoro, chloro, C$_{1-6}$alkyl, C$_{1-6}$alkyl substituted 1 to 6 times by fluoro, C$_{1-4}$alkoxy, C$_{1-4}$alkoxy substituted 1 to 6 times by fluoro, oxo, and —NH$_2$, and
R$^1$ taken together with L$^1$ form a cycloalkyl or heterocycloalkyl, which is optionally substituted with from 1 to 5 substituents independently selected from:
fluoro, chloro, C$_{1-6}$alkyl, C$_{1-6}$alkyl substituted 1 to 6 times by fluoro, C$_{1-4}$alkoxy, C$_{1-4}$alkoxy substituted 1 to 6 times by fluoro, oxo, and —NH$_2$, or;
R$^3$, R$^5$ and R$^6$ and are independently hydrogen, fluoro, chloro, bromo, iodo, —OCH$_3$, —OCH$_2$Ph, —C(O)Ph, —CH$_3$, —CF$_3$, —CN, —S(O)CH$_3$, —OH, —NH$_2$, —COOH, —CONH$_2$, —NO$_2$, —C(O)CH$_3$, —CH(CH$_3$)$_2$, —CCH, —CH$_2$CCH, —SO$_3$H, —SO$_2$NH$_2$, —NHC(O)NH$_2$, —NHC(O)H, —NHOH, —OCF$_3$, —OCHF$_2$, substituted or unsubstituted C$_{1-6}$alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^2$ and R$^4$ are independently NR$^8$, O, CH$_2$, or S;
R$^7$ is selected from: =NR$^8$, =O, =CH$_2$ and =S;
R$^8$ is selected from: hydrogen, C$_{1-6}$alkyl and C$_{1-6}$alkyl substituted 1 to 6 times by fluoro;
R$^9$ is selected from: —CH—, R$^9$ taken together with R$^3$ and the nitrogen to which R$^3$ is attached, and optionally from 1 to 3 additional heteroatoms, form a heterocycloalkyl, which is optionally substituted with from 1 to 5 substituents independently selected from:
fluoro, chloro, C$_{1-6}$alkyl, C$_{1-6}$alkyl substituted 1 to 6 times by fluoro, C$_{1-4}$alkoxy, C$_{1-4}$alkoxy substituted 1 to 6 times by fluoro, oxo, and —NH$_2$, and
R$^9$ taken together with L$^1$ form a C$_{3-7}$cycloalkyl, which is optionally substituted with from 1 to 5 substituents independently selected from:
fluoro, chloro, C$_{1-3}$alkyl, C$_{1-3}$alkyl substituted 1 to 3 times by fluoro, C$_{1-3}$alkoxy, C$_{1-3}$alkoxy substituted 1 to 3 times by fluoro, and oxo;

R$^{10}$ is selected from: hydrogen, C$_{1-3}$alkyl, oxo, hydroxyl and C$_{1-3}$alkoxy;
Z$^2$ and z$^4$ are independently 0 or 1; and
Z$^5$ and z$^6$ are independently an integer from 0 to 4;
and salts thereof.

This invention also relates to pharmaceutically acceptable salts of the compounds of Formula (III).

Included in the compounds of the invention and used in the methods of the invention are compounds of Formula (II):

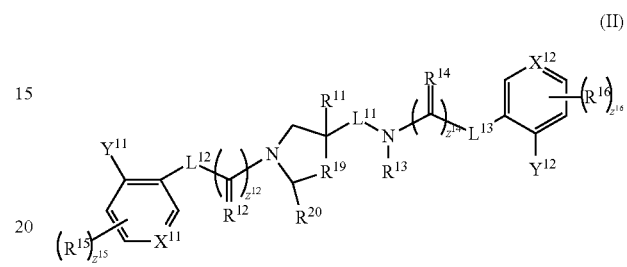

(II)

wherein:
X$^{11}$ and X$^{12}$ are independently —CH— or —N—;
L$^{12}$ and L$^{13}$ are independently: —NH—, —NH—CH$_2$—, —CH$_2$—C(O)—NH—, —NH—C(O)—CH$_2$—, —CH$_2$—CH$_2$—CH$_2$—O—, —O—CH$_2$—, —O—CH$_2$—CH$_2$— or —O—CH$_2$—CH$_2$—CH$_2$—;
L$^{11}$ is selected from: a bond, —CH$_2$—, —CH$_2$—CH$_2$—, and —CH$_2$—CH$_2$—CH$_2$—;
Y$^{11}$ is hydrogen or is C$_{1-2}$alkyl and taken together with L$^{12}$ to form piperidinyl, tetrahydrofuranyl or tetrahydropyranyl;
Y$^{12}$ is hydrogen or is C$_{1-2}$alkyl and taken together with L$^{13}$ to form tetrahydrofuranyl or tetrahydropyranyl;
R$^{11}$ is selected from: hydrogen, methyl, R$^{11}$ taken together with R$^{13}$ form pyrrolidinyl, and R$^{11}$ taken together with L$^{11}$ form cyclohexyl;
R$^{13}$, when not part of a ring with R$^{11}$ or R$^{19}$, is hydrogen;
R$^{19}$ is selected from: —CH—, R$^{19}$ taken together with R$^{13}$ and the nitrogen to which R$^{13}$ is attached form pyrrolidinyl, and R$^{19}$ taken together with L$^{11}$ form cyclopropyl;
R$^{15}$ and R$^{16}$ are independently hydrogen, fluoro or chloro;
R$^{12}$ and R$^{14}$ are O;
R$^{20}$ is selected from hydrogen and oxo;
z$^{12}$ and z$^{14}$ are independently 0 or 1; and
z$^{15}$ and z$^{16}$ are independently an integer from 0 to 2;
and salts thereof.

This invention also relates to pharmaceutically acceptable salts of the compounds of Formula (II).

Included in the compounds of the invention and used in the methods of the invention are compounds of Formula (III):

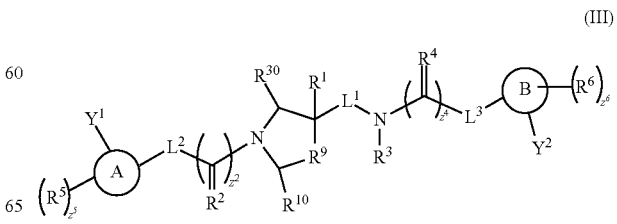

(III)

wherein:
A and B are independently phenyl or pyridyl;
$L^2$ and $L^3$ are independently a bond, —NH—, —N(CH$_3$)—, —O—, —S—, —S(O)—, —S(O)$_2$—, substituted or unsubstituted C$_{1-6}$alkylene or substituted or unsubstituted C$_{1-6}$heteroalkylene;
$L^1$ is selected from: a bond, —NH—, —C(R$^7$)—, —O—, —S—, —S(O)—, —S(O)$_2$—, substituted or unsubstituted C$_{1-6}$alkylene and substituted or unsubstituted C$_{1-6}$heteroalkylene;
$Y^1$ is hydrogen or is C$_{1-4}$alkyl and taken together with $L^2$ to form a heterocycloalkyl, which is optionally substituted with from 1 to 5 substituents independently selected from:
fluoro, chloro, C$_{1-6}$alkyl, C$_{1-6}$alkyl substituted 1 to 6 times by fluoro, C$_{1-4}$alkoxy, C$_{1-4}$alkoxy substituted 1 to 6 times by fluoro, oxo, and —NH$_2$;
$Y^2$ is hydrogen or is C$_{1-4}$alkyl and taken together with $L^3$ to form a heterocycloalkyl, which is optionally substituted with from 1 to 5 substituents independently selected from:
fluoro, chloro, C$_{1-6}$alkyl, C$_{1-6}$alkyl substituted 1 to 6 times by fluoro, C$_{1-4}$alkoxy, C$_{1-4}$alkoxy substituted 1 to 6 times by fluoro, oxo, and —NH$_2$;
$R^1$ is selected from: hydrogen, fluoro, chloro, —OH, C$_{1-6}$alkyl, C$_{1-6}$alkyl substituted 1 to 6 times by fluoro, $R^1$ taken together with $R^3$ and the nitrogen to which $R^3$ is attached, and optionally from 1 to 3 additional heteroatoms, form a heterocycloalkyl, which is optionally substituted with from 1 to 5 substituents independently selected from:
fluoro, chloro, C$_{1-6}$alkyl, C$_{1-6}$alkyl substituted 1 to 6 times by fluoro, C$_{1-4}$alkoxy, C$_{1-4}$alkoxy substituted 1 to 6 times by fluoro, oxo, and —NH$_2$, and
$R^1$ taken together with $L^1$ form a cycloalkyl or heterocloalkyl, which is optionally substituted with from 1 to 5 substituents independently selected from:
fluoro, chloro, C$_{1-6}$alkyl, C$_{1-6}$alkyl substituted 1 to 6 times by fluoro, C$_{1-4}$alkoxy, C$_{1-4}$alkoxy substituted 1 to 6 times by fluoro, oxo, and —NH$_2$, or;
$R^3$, $R^5$ and $R^6$ and are independently hydrogen, fluoro, chloro, bromo, iodo, —OCH$_3$, —OCH$_2$Ph, —C(O)Ph, —CH$_3$, —CF$_3$, —CN, —S(O)CH$_3$, —OH, —NH$_2$, —COOH, —CONH$_2$, —NO$_2$, —C(O)CH$_3$, —CH(CH$_3$)$_2$, —CCH, —CH$_2$CCH, —SO$_3$H, —SO$_2$NH$_2$, —NHC(O)NH$_2$, —NHC(O)H, —NHOH, —OCF$_3$, —OCHF$_2$, substituted or unsubstituted C$_{1-6}$alkylene, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ and $R^4$ are independently NR$^8$, O, CH$_2$, or S;
$R^7$ is selected from: =NR$^8$, =O, =CH$_2$ and =S;
$R^8$ is selected from: hydrogen, C$_{1-6}$alkyl and C$_{1-6}$alkyl substituted 1 to 6 times by fluoro;
$R^9$ is selected from: —CH—, —C(CH$_3$)—, $R^9$ taken together with $R^3$ and the nitrogen to which $R^3$ is attached, and optionally from 1 to 3 additional heteroatoms, form a heterocycloalkyl, which is optionally substituted with from 1 to 5 substituents independently selected from:
fluoro, chloro, C$_{1-6}$alkyl, C$_{1-6}$alkyl substituted 1 to 6 times by fluoro, C$_{1-4}$alkoxy, C$_{1-4}$alkoxy substituted 1 to 6 times by fluoro, oxo, and —NH$_2$, and
$R^9$ taken together with $L^1$ form a C$_{3-7}$cycloalkyl, which is optionally substituted with from 1 to 5 substituents independently selected from:
fluoro, chloro, C$_{1-3}$alkyl, C$_{1-3}$alkyl substituted 1 to 3 times by fluoro, C$_{1-3}$alkoxy, C$_{1-3}$alkoxy substituted 1 to 3 times by fluoro, and oxo;
$R^{10}$ is selected from: hydrogen, C$_{1-3}$alkyl, oxo, hydroxyl and C$_{1-3}$alkoxy;
$R^{30}$ is selected from: hydrogen, C$_{1-3}$alkyl, oxo, hydroxyl and C$_{1-3}$alkoxy;
$z^2$ and $z^4$ are independently 0 or 1; and
$z^5$ and $z^6$ are independently an integer from 0 to 4; and salts thereof.

This invention also relates to pharmaceutically acceptable salts of the compounds of Formula (III).

Included in the compounds of the invention and used in the methods of the invention are compounds of Formula (IV):

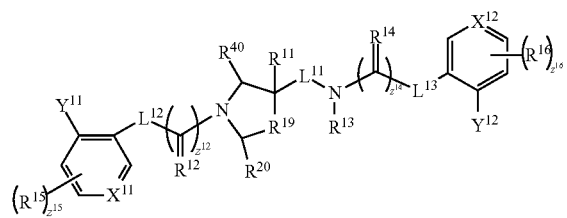

(IV)

wherein:
$X^{11}$ and $X^{12}$ are independently —CH— or —N—;
$L^{12}$ and $L^{13}$ are independently: —NH—, —N(CH$_3$)—, —NH—CH$_2$—, —CH$_2$—C(O)—NH—, —NH—C(O)—CH$_2$—, —CH$_2$—CH$_2$—CH$_2$—O—; —O—CH$_2$—CH$_2$— or —O—CH$_2$—CH$_2$—CH$_2$—;
$L^{11}$ is selected from: a bond, —O—, —CH$_2$—, —CH$_2$—CH$_2$—, and —CH$_2$—CH$_2$—CH$_2$—;
$Y^{11}$ is hydrogen or is C$_{1-2}$alkyl and taken together with $L^{12}$ to form piperidinyl, tetrahydrofuranyl or tetrahydropyranyl;
$Y^{12}$ is hydrogen or is C$_{1-2}$alkyl and taken together with $L^{13}$ to form tetrahydrofuranyl or tetrahydropyranyl;
$R^{11}$ is selected from: hydrogen, methyl, fluoro, —OH, $R^{11}$ taken together with $R^{13}$ form pyrrolidinyl, and $R^{11}$ taken together with $L^{11}$ form cyclohexyl;
$R^{13}$, when not part of a ring with $R^{11}$ or $R^{19}$, is hydrogen;
$R^{19}$ is selected from: —CH—, —C(CH$_3$)—, $R^{19}$ taken together with $R^{13}$ and the nitrogen to which $R^{13}$ is attached form pyrrolidinyl, and $R^{19}$ taken together with $L^{11}$ form cyclopropyl;
$R^{15}$ and $R^{16}$ are independently hydrogen, —CH$_3$—, —OCH$_3$—, —CF$_3$—, fluoro or chloro;
$R^{12}$ and $R^{14}$ are O;
$R^{20}$ is selected from hydrogen, —CH$_3$—, and oxo;
$R^{40}$ is selected from hydrogen, —CH$_3$—, and oxo;
$z^{12}$ and $z^{14}$ are independently 0 or 1; and
$z^{15}$ and $z^{16}$ are independently an integer from 0 to 2; and salts thereof.

This invention also relates to pharmaceutically acceptable salts of the compounds of Formula (IV).

Included in the compounds of Formula (III) are:
2-(4-chlorophenoxy)-N-((1-(2-(4-chlorophenoxy)acetyl)pyrrolidin-3-yl)methyl)acetamide;
2-(4-chlorophenoxy)-N-((1-(2-(4-chlorophenoxy)ethyl)pyrrolidin-3-yl)methyl)acetamide;
2-(4-chlorophenoxy)-N-((1-(2-(4-chlorophenoxy)ethyl)-5-oxopyrrolidin-3-yl)methyl)acetamide;

2-(4-chlorophenoxy)-N-((1-(2-((4-chlorophenyl)amino)-2-oxoethyl)pyrrolidin-3-yl)methyl)acetamide;
2-(4-chloro-3-fluorophenoxy)-N-((1-(2-(4-chlorophenoxy)acetyl)pyrrolidin-3-yl)methyl)acetamide;
1,1'-(tetrahydropyrrolo[3,4-c]pyrrole-2,5(1H,3H)-diyl)bis(2-(4-chlorophenoxy)ethanone);
2-(4-chlorophenoxy)-N-(1-(2-(4-chlorophenoxy)acetyl)pyrrolidin-3-yl)acetamide;
N-((1-(6-chlorochroman-2-carbonyl)pyrrolidin-3-yl)methyl)-2-(4-chlorophenoxy)acetamide;
N-((1-(5-chloro-2,3-dihydrobenzofuran-2-carbonyl)pyrrolidin-3-yl)methyl)-2-(4-chlorophenoxy)acetamide;
2-(4-chlorophenoxy)-N-((1-(2-((5-chloropyridin-3-yl)oxy)acetyl)pyrrolidin-3-yl)methyl)acetamide;
2-(4-chlorophenoxy)-N-((1-(2-((6-chloropyridin-3-yl)oxy)acetyl)pyrrolidin-3-yl)methyl)acetamide (enantiomer 1);
2-(4-chlorophenoxy)-N-((1-(2-((6-chloropyridin-3-yl)oxy)acetyl)pyrrolidin-3-yl)methyl)acetamide (enantiomer 2);
2-(4-chlorophenoxy)-N-((1-(2-((6-chloropyridin-3-yl)oxy)ethyl)pyrrolidin-3-yl)methyl)acetamide;
2-(4-chlorophenoxy)-N-((1-(3-(4-chlorophenoxy)propanoyl)pyrrolidin-3-yl)methyl)acetamide;
4-chlorophenethyl 3-((2-(4-chlorophenoxy)acetamido)methyl)pyrrolidine-1-carboxylate;
2-(4-chlorophenoxy)-N-(2-(1-(2-(4-chlorophenoxy)acetyl)pyrrolidin-3-yl)ethyl)acetamide;
2-(4-chlorophenoxy)-N-((1-(2-(4-chlorophenoxy)acetyl)-3-methylpyrrolidin-3-yl)methyl)acetamide;
5-chloro-N-((1-(2-(4-chlorophenoxy)acetyl)pyrrolidin-3-yl)methyl)-2,3-dihydrobenzofuran-2-carboxamide;
N-((1-(2-(4-chlorophenoxy)acetyl)pyrrolidin-3-yl)methyl)-2-((6-chloropyridin-3-yl)oxy)acetamide;
2-(4-chlorophenoxy)-N-((1-(2-((6-chloropyridin-3-yl)oxy)acetyl)pyrrolidin-3-yl)methyl)acetamide;
2-(4-chlorophenoxy)-1-(3-(((2-(4-chlorophenoxy)ethyl)amino)methyl)pyrrolidin-1-yl)ethanone;
6-chloro-N-((1-(2-(4-chlorophenoxy)acetyl)pyrrolidin-3-yl)methyl)chroman-2-carboxamide;
2-(4-chlorophenoxy)-N-(2-(2-(4-chlorophenoxy)acetyl)-2-azaspiro[4.5]decan-8-yl)acetamide;
N-((1-(6-chloro-1,2,3,4-tetrahydroisoquinoline-2-carbonyl)pyrrolidin-3-yl)methyl)-2-(4-chlorophenoxy)acetamide;
2-(4-chlorophenoxy)-N-((1-(2-((4-chlorophenyl)amino)acetyl)pyrrolidin-3-yl)methyl)acetamide);
1,1'-(2,7-diazaspiro[4.4]nonane-2,7-diyl)bis(2-(4-chlorophenoxy)ethanone);
2-(4-chlorophenoxy)-N-((1-(3-(4-chlorophenoxy)propyl)pyrrolidin-3-yl)methyl)acetamide;
2-(4-chlorophenoxy)-N-((1R,5S,6s)-3-(3-(4-chlorophenoxy)propyl)-3 azabicyclo[3.1.0]hexan-6-yl)acetamide;
(S)-2-(4-chlorophenoxy)-N-((1-(2-(4-chlorophenoxy)acetyl)pyrrolidin-3-yl)methyl)acetamide;
((R)-2-(4-chlorophenoxy)-N-((1-(2-(4-chlorophenoxy)acetyl)pyrrolidin-3-yl)methyl)acetamide;
2-(4-chlorophenoxy)-N-((1R,5S,6s)-3-(2-(4-chlorophenoxy)acetyl)-3-azabicyclo[3.1.0]hexan-6-yl)acetamide;
2-(4-chlorophenoxy)-N-((1S,5R)-3-(2-(4-chlorophenoxy)acetyl)-3-azabicyclo[3.2.0]heptan-6-yl)acetamide;
2-(4-chlorophenoxy)-N-((1-(2-(4-chlorophenoxy)acetyl)pyrrolidin-3-yl)oxy)acetamide;
2-(4-chlorophenoxy)-N-((1-(2-(4-chlorophenyl)cyclopropane-1-carbonyl)pyrrolidin-3-yl)oxy)acetamide;
2-(4-chlorophenoxy)-N-((1-(3-(4-chlorophenoxy)propanoyl)pyrrolidin-3-yl)oxy)acetamide;
2-(4-chlorophenoxy)-N-((1-(2-(4-chlorophenoxy)acetyl)-3-fluoropyrrolidin-3-yl)methyl)acetamide;
2-(4-chlorophenoxy)-N-((1R,5S,6s)-3-(2-(4-chlorophenyl)cyclopropane-1-carbonyl)-3-azabicyclo[3.1.0]hexan-6-yl)acetamide;
2-(4-chlorophenoxy)-N-((1-(4-(4-chlorophenyl)butanoyl)pyrrolidin-3-yl)methyl)acetamide;
2-(4-chlorophenoxy)-N-((1-(2-(4-chlorophenoxy)acetyl)-5-methylpyrrolidin-3-yl)methyl)acetamide;
2-(4-chlorophenoxy)-N-((1-(2-(4-chlorophenyl)cyclopropanecarbonyl)pyrrolidin-3-yl)methyl)acetamide;
2-(4-chlorophenoxy)-N-((1-(2-(4-chlorophenoxy)ethyl)-5-methylpyrrolidin-3-yl)methyl)acetamide;
2-(4-chlorophenoxy)-N-((1-(2-(4-chlorophenoxy)ethyl)-3-fluoropyrrolidin-3-yl)methyl)acetamide;
2-(4-chlorophenoxy)-N-((1-(2-(4-chlorophenoxy)ethyl)-3-methylpyrrolidin-3-yl)methyl)acetamide;
N-((1-(3-(4-chlorophenoxy)propyl)pyrrolidin-3-yl)methyl)-2-(3,4-dichlorophenoxy)acetamide;
N-((1-(3-(4-chlorophenoxy)propyl)pyrrolidin-3-yl)methyl)-2-(4-(trifluoromethyl)phenoxy)acetamide;
2-(2-chloro-4-fluorophenoxy)-N-((1-(3-(4-chlorophenoxy)propyl)pyrrolidin-3-yl)methyl)acetamide;
2-(4-chloro-3-methylphenoxy)-N-((1-(3-(4-chlorophenoxy)propyl)pyrrolidin-3-yl)methyl)acetamide;
2-(4-chloro-3-fluorophenoxy)-N-((1-(3-(4-chloro-3-fluorophenoxy)propyl)pyrrolidin-3-yl)methyl)acetamide;
2-(4-chlorophenoxy)-N-((1-(3-(4-fluorophenoxy)propyl)pyrrolidin-3-yl)methyl)acetamide;
2-(4-chlorophenoxy)-N-((1-(3-(3-chlorophenoxy)propyl)pyrrolidin-3-yl)methyl)acetamide;
N-((1R,5S,6s)-3-(3-(4-chlorophenoxy)propyl)-3-azabicyclo[3.1.0]hexan-6-yl)-2-((6-chloropyridin-3-yl)oxy)acetamide;
N-((1R,5S,6s)-3-(3-(4-chlorophenoxy)propyl)-3-azabicyclo[3.1.0]hexan-6-yl)-2-((5-chloropyridin-2-yl)oxy)acetamide;
2-(4-chlorophenoxy)-N-((1R,5S,6s)-3-(3-((5-chloropyridin-2-yl)oxy)propyl)-3-azabicyclo[3.1.0]hexan-6-yl)acetamide;
N-((1-(3-(4-chloro-3-methoxyphenoxy)propyl)pyrrolidin-3-yl)methyl)-2-(4-chlorophenoxy)acetamide;
2-(4-chloro-3-fluorophenoxy)-N-((1-(3-(4-chlorophenoxy)propyl)pyrrolidin-3-yl)methyl)acetamide;
N-((1-(3-(4-chlorophenoxy)propyl)pyrrolidin-3-yl)methyl)-2-((5-chloropyridin-2-yl)oxy)acetamide;
N-((1-(3-(4-chloro-3-methylphenoxy)propyl)pyrrolidin-3-yl)methyl)-2-(4-chlorophenoxy)acetamide;
2-(4-chlorophenoxy)-N-(((3R)-1-(3-(4-chlorophenoxy)propyl)-5-methylpyrrolidin-3-yl)methyl)acetamide;
2-(4-chlorophenoxy)-N-((1-(3-(4-chlorophenoxy)propyl)pyrrolidin-3-yl)methyl)acetamide;
2-(4-chlorophenoxy)-N-((1-(3-(4-chlorophenoxy)propyl)-3-fluoropyrrolidin-3-yl)methyl)acetamide;
2-(4-chlorophenoxy)-N-((1-(3-(3,4-dichlorophenoxy)propyl)pyrrolidin-3-yl)methyl)acetamide;
N-((1-(3-(4-chloro-2-fluorophenoxy)propyl)pyrrolidin-3-yl)methyl)-2-(4-chlorophenoxy)acetamide;
2-(4-chlorophenoxy)-N-((1-(3-(4-(trifluoromethyl)phenoxy)propyl)pyrrolidin-3-yl)methyl)acetamide;
N-((1-(3-(4-chloro-3-fluorophenoxy)propyl)pyrrolidin-3-yl)methyl)-2-(4-chlorophenoxy)acetamide;
2-(4-chlorophenoxy)-N-((1R,5S,6s)-3-(3-((6-chloropyridin-3-yl)oxy)propyl)-3-azabicyclo[3.1.0]hexan-6-yl)acetamide;
2-(4-chlorophenoxy)-N-((1-(3-(2,4-dichlorophenoxy)propyl)pyrrolidin-3-yl)methyl)acetamide;
N-((1-(3-(4-chloro-2-methylphenoxy)propyl)pyrrolidin-3-yl)methyl)-2-(4-chlorophenoxy)acetamide;

N-((1-(3-(4-chloro-3-(trifluoromethyl)phenoxy)propyl)pyrrolidin-3-yl)methyl)-2-(4-chlorophenoxy)acetamide;
2-(4-chlorophenoxy)-N-((1-(3-((5-chloropyridin-2-yl)oxy)propyl)pyrrolidin-3-yl)methyl)acetamide;
(S)-2-(4-chlorophenoxy)-N-((1-(3-(4-chlorophenoxy)propyl)pyrrolidin-3-yl)methyl)acetamide;
N-((1R,5S,6s)-3-(3-(4-chlorophenoxy)propyl)-3-azabicyclo[3.1.0]hexan-6-yl)-2-((6-chloropyridin-3-yl)oxy)acetamide;
2-(4-chloro-3-(trifluoromethyl)phenoxy)-N-((1-(3-(4-chlorophenoxy)propyl)pyrrolidin-3-yl)methyl)acetamide;
(R)-2-(4-chlorophenoxy)-N-((1-(3-(4-chlorophenoxy)propyl)pyrrolidin-3-yl)methyl)acetamide;
2-(4-chlorophenoxy)-N-((1-(3-(4-chlorophenoxy)propyl)-3-hydroxypyrrolidin-3-yl)methyl)acetamide;
2-(4-chlorophenoxy)-N-((1-(3-(4-chlorophenoxy)propyl)-2-oxopyrrolidin-3-yl)methyl)acetamide;
2-(4-chlorophenoxy)-N-((1R,5S,6s)-3-(3-(4-chlorophenoxy)-2-hydroxypropyl)-3-azabicyclo[3.1.0]hexan-6-yl)acetamide;
2-(4-chlorophenoxy)-N-((1-(3-(4-chlorophenoxy)-2-hydroxypropyl)pyrrolidin-3-yl)methyl)acetamide;
2-(4-chlorophenoxy)-N-((1R,5S,6s)-3-(3-(4-chlorophenoxy)-2-fluoropropyl)-3-azabicyclo[3.1.0]hexan-6-yl)acetamide;
N-(4-chlorobenzyl)-3-((2-(4-chlorophenoxy)acetamido)methyl)-N-methylpyrrolidine-1-carboxamide;
2-(4-chlorophenoxy)-N-((1-(3-(4-chlorophenoxy)propyl)-4-hydroxypyrrolidin-3-yl)methyl)acetamide;
2-(4-chlorophenoxy)-N-((1-(3-(4-chlorophenoxy)propyl)-5-oxopyrrolidin-3-yl)methyl)acetamide; and
4-(4-chlorophenoxy)-2-((1R,5S)-6-(2-(4-chlorophenoxy)acetamido)-3-azabicyclo[3.1.0]hexan-3-yl)butanoic acid;
and salts thereof including pharmaceutically acceptable salts thereof.

$L^1$ may be a bond or substituted or unsubstituted $C_1$-$C_6$ alkylene alkylene. $L^1$ may be substituted or unsubstituted $C_1$-$C_5$ alkylene. $L^1$ may be substituted or unsubstituted $C_1$-$C_3$ alkylene. $L^1$ may be substituted or unsubstituted methylene. $L^1$ may be a bond. $L^1$ may be an unsubstituted alkylene. $L^1$ may be an unsubstituted methylene. $L^1$ may be an unsubstituted ethylene. $L^1$ may be a methylene substituted with an unsubstituted alkyl. $L^1$ may be a methylene substituted with an unsubstituted $C_1$-$C_4$ alkyl. $L^1$ may be a methylene substituted with an unsubstituted $C_1$-$C_3$ alkyl.

Suitably, $R^3$ is hydrogen. Suitably, $R^3$ is —CH$_2$CCH.

Suitably, $R^3$ is substituted or unsubstituted $C_{1-6}$alkylene, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Suitably, $R^3$ is substituted or unsubstituted $C_{1-6}$alkylene. Suitably, $R^3$ is substituted or unsubstituted $C_1$-$C_5$ alkyl. Suitably, $R^3$ is substituted or unsubstituted $C_1$-$C_4$ alkyl. Suitably, $R^3$ is substituted or unsubstituted $C_1$-$C_3$ alkyl. Suitably, $R^3$ is unsubstituted $C_{1-6}$alkylene. Suitably, $R^3$ is unsubstituted $C_1$-$C_5$ alkyl. Suitably, $R^3$ is unsubstituted $C_1$-$C_4$ alkyl. Suitably, $R^3$ is unsubstituted $C_1$-$C_3$ alkyl. Suitably, $R^3$ is substituted or unsubstituted heteroalkyl. Suitably, $R^3$ is substituted or unsubstituted 2 to 8 membered heteroalkyl. Suitably, $R^3$ is unsubstituted 2 to 8 membered heteroalkyl.

In embodiments, $R^5$ is independently hydrogen, fluoro, chloro, bromo, iodo, —OCH$_3$, —OCH$_2$Ph, —C(O)Ph, —CH$_3$, —CF$_3$, —CN, —S(O)CH$_3$, —OH, —NH$_2$, —COOH, —CONH$_2$, —NO$_2$, —C(O)CH$_3$, —CH(CH$_3$)$_2$, —CCH, —CH$_2$CCH, —SO$_3$H, —SO$_2$NH$_2$, —NHC(O)NH$_2$, —NHC(O)H, —NHOH, —OCH$_3$, —OCF$_3$, —OCHF$_2$, substituted or unsubstituted $C_{1-6}$alkylene, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^5$ is independently hydrogen, fluoro, chloro, bromo, iodo, —OCH$_3$, —OCH$_2$Ph, —CH$_3$, —OH, —CF$_3$, —CN, —S(O)CH$_3$, —NO$_2$, —C(O)CH$_3$, —C(O)Ph, —CH(CH$_3$)$_2$, or —CCH. In embodiments, $R^5$ is —F. In embodiments, $R^5$ is —Cl. In embodiments, $R^5$ is —Br. In embodiments, $R^5$ is —I. In embodiments, $R^5$ is substituted or unsubstituted $C_{1-6}$alkylene, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^5$ is unsubstituted $C_{1-6}$alkylene, unsubstituted heteroalkyl, unsubstituted cycloalkyl, unsubstituted heterocycloalkyl, unsubstituted aryl, or unsubstituted heteroaryl. In embodiments, $R^5$ is —OCH$_3$. In embodiments, $R^5$ is —OCH$_2$Ph. In embodiments, $R^5$ is —CH$_3$. In embodiments, $R^5$ is —OH. In embodiments, $R^5$ is —CF$_3$. In embodiments, $R^5$ is —CN. In embodiments, $R^5$ is —S(O)CH$_3$. In embodiments, $R^5$ is —NO$_2$. In embodiments, $R^5$ is —C(O)CH$_3$. In embodiments, $R^5$ is —C(O)Ph. In embodiments, $R^5$ is —CH(CH$_3$)$_2$. In embodiments, $R^5$ is —CCH. In embodiments, $R^5$ is —CH$_2$CCH. In embodiments, $R^5$ is —SO$_3$H. In embodiments, $R^5$ is —SO$_2$NH$_2$. In embodiments, $R^5$ is —NHC(O)NH$_2$. In embodiments, $R^5$ is —NHC(O)H. In embodiments, $R^5$ is —NHOH. In embodiments, $R^5$ is-OCH$_3$. In embodiments, R is —OCF$_3$. In embodiments, $R^5$ is —OCHF$_2$.

In embodiments, $R^6$ is independently hydrogen, fluoro, chloro, bromo, iodo, —OCH$_3$, —OCH$_2$Ph, —C(O)Ph, —CH$_3$, —CF$_3$, —CN, —S(O)CH$_3$, —OH, —NH$_2$, —COOH, —CONH$_2$, —NO$_2$, —C(O)CH$_3$, —CH(CH$_3$)$_2$, —CCH, —CH$_2$CCH, —SO$_3$H, —SO$_2$NH$_2$, —NHC(O)NH$_2$, —NHC(O)H, —NHOH, —OCH$_3$, —OCF$_3$, —OCHF$_2$, substituted or unsubstituted $C_{1-6}$alkylene, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^6$ is independently hydrogen, fluoro, chloro, bromo, iodo, —OCH$_3$, —OCH$_2$Ph, —CH$_3$, —OH, —CF$_3$, —CN, —S(O)CH$_3$, —NO$_2$, —C(O)CH$_3$, —C(O)Ph, —CH(CH$_3$)$_2$, or —CCH. In embodiments, $R^6$ is —F. In embodiments, $R^6$ is —Cl. In embodiments, $R^6$ is —Br. In embodiments, $R^6$ is —I. In embodiments, $R^6$ is substituted or unsubstituted $C_{1-6}$alkylene, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^6$ is unsubstituted $C_{1-6}$alkylene, unsubstituted heteroalkyl, unsubstituted cycloalkyl, unsubstituted heterocycloalkyl, unsubstituted aryl, or unsubstituted heteroaryl. In embodiments, $R^6$ is —OCH$_3$. In embodiments, $R^6$ is —OCH$_2$Ph. In embodiments, $R^6$ is —CH$_3$. In embodiments, $R^6$ is —OH. In embodiments, $R^6$ is —CF$_3$. In embodiments, $R^6$ is —CN. In embodiments, $R^6$ is —S(O)CH$_3$. In embodiments, $R^6$ is —NO$_2$. In embodiments, $R^6$ is —C(O)CH$_3$. In embodiments, $R^6$ is —C(O)Ph. In embodiments, $R^6$ is —CH(CH$_3$)$_2$. In embodiments, $R^6$ is —CCH. In embodiments, $R^6$ is —CH$_2$CCH. In embodiments, $R^6$ is —SO$_3$H. In embodiments, $R^6$ is —SO$_2$NH$_2$. In embodiments, $R^6$ is —NHC(O)NH$_2$. In embodiments, $R^6$ is —NHC(O)H. In embodiments, $R^6$ is —NHOH. In embodiments, $R^6$ is-OCH$_3$. In embodiments, $R^6$ is —OCF$_3$. In embodiments, $R^6$ is —OCHF$_2$.

In embodiments, $R^2$ is $NR^8$. In embodiments, $R^2$ is NH. In embodiments, $R^2$ is O. In embodiments, $R^2$ is S. In embodiments, $R^4$ is $NR^8$. In embodiments, $R^4$ is NH. In embodiments, $R^4$ is O. In embodiments, $R^4$ is S. In embodiments, $R^2$ and $R^4$ are NH. In embodiments, $R^2$ and $R^4$ are O. In embodiments, $R^2$ and $R^4$ are S. In embodiments, $R^2$ and $R^4$ are $NR^8$.

In embodiments, $L^2$ is a bond. In embodiments, $L^2$ is a substituted or unsubstituted $C_{1-6}$alkylene. In embodiments, $L^2$ is a substituted or unsubstituted $C_{1-6}$heteroalkylene. In embodiments, $L^2$ is $L^{2A}$-$L^{2B}$-$L^{2C}$ and $L^{2A}$ is bonded to the substituted or unsubstituted phenyl, which may be substituted with $R^5$. $L^{2A}$ is a bond, —O—, —S—, —NH—, —S(O)—, or —S(O)$_2$—. $L^{2B}$ is a bond or substituted or unsubstituted $C_{1-6}$alkylene. $L^{2C}$ is a bond, —O—, or NH—. In embodiments, $L^{2A}$ is a bond. In embodiments, $L^{2A}$ is —O—. In embodiments, $L^{2A}$ is —S—. In embodiments, $L^{2A}$ is —NH—. In embodiments, $L^{2A}$ is —S(O)—. In embodiments, $L^{2A}$ is —S(O)$_2$—. In embodiments, $L^{2B}$ is a bond. In embodiments, $L^{2B}$ is a substituted or unsubstituted $C_{1-6}$alkylene. In embodiments, $L^{2B}$ is an unsubstituted $C_{1-6}$alkylene. In embodiments, $L^{2B}$ is a substituted or unsubstituted $C_1$-$C_5$ alkylene. In embodiments, $L^{2B}$ is an unsubstituted $C_1$-$C_5$ alkylene. In embodiments, $L^{2B}$ is a substituted or unsubstituted $C_1$-$C_4$ alkylene. In embodiments, $L^{2B}$ is an unsubstituted $C_4$ alkylene. In embodiments, $L^{2B}$ is a substituted or unsubstituted $C_1$-$C_3$ alkylene. In embodiments, $L^{2B}$ is an unsubstituted $C_1$-$C_3$ alkylene. In embodiments, $L^{2B}$ is a substituted $C_1$-$C_5$ alkylene. In embodiments, $L^{2B}$ is a substituted $C_1$-$C_6$ alkylene. In embodiments, $L^{2B}$ is a substituted $C_1$-$C_5$ alkylene. In embodiments, $L^{2B}$ is a substituted $C_1$-$C_4$ alkylene. In embodiments, $L^{2B}$ is a $C_1$-$C_6$ alkylene substituted with —$CF_3$. In embodiments, $L^{2C}$ is a bond. In embodiments, $L^{2C}$ is —O—. In embodiments, $L^{2C}$ is —NH—. In embodiments, $L^{2A}$ is a bond; $L^{2B}$ is unsubstituted methylene; and $L^{2C}$ is —O—.

In embodiments, $L^3$ is a bond. In embodiments, $L^3$ is a substituted or unsubstituted $C_{1-6}$alkylene. In embodiments, $L^3$ is a substituted or unsubstituted $C_{1-6}$heteroalkylene. In embodiments, $L^3$ is $L^{3A}$-$L^{3B}$-$L^{3C}$ and $L^{3A}$ is bonded to the substituted or unsubstituted phenyl, which may be substituted with $R^5$. $L^{3A}$ is a bond, —O—, —S—, —NH—, —S(O)—, or —S(O)$_2$—. $L^{3B}$ is a bond or substituted or unsubstituted $C_{1-6}$alkylene. $L^{3C}$ is a bond, —O—, or NH—. In embodiments, $L^{3A}$ is a bond. In embodiments, $L^{3A}$ is —O—. In embodiments, $L^{3A}$ is —S—. In embodiments, $L^{3A}$ is —NH—. In embodiments, $L^{3A}$ is —S(O)—. In embodiments, $L^{3A}$ is —S(O)$_2$—. In embodiments, $L^{3B}$ is a bond. In embodiments, $L^{3B}$ is a substituted or unsubstituted $C_{1-6}$alkylene. In embodiments, $L^{3B}$ is an unsubstituted $C_{1-6}$alkylene. In embodiments, $L^{3B}$ is a substituted or unsubstituted $C_1$-$C_5$ alkylene. In embodiments, $L^{3B}$ is an unsubstituted $C_1$-$C_5$ alkylene. In embodiments, $L^{3B}$ is a substituted or unsubstituted $C_1$-$C_4$ alkylene. In embodiments, $L^{3B}$ is an unsubstituted $C_1$-$C_4$ alkylene. In embodiments, $L^{3B}$ is a substituted or unsubstituted $C_1$-$C_3$alkylene. In embodiments, $L^{3B}$ is an unsubstituted $C_1$-$C_3$ alkylene. In embodiments, $L^{3B}$ is a substituted $C_1$-$C_5$ alkylene. In embodiments, $L^{3B}$ is a substituted $C_1$-$C_6$ alkylene. In embodiments, $L^{3B}$ is a substituted $C_1$-$C_5$ alkylene. In embodiments, $L^{3B}$ is a substituted $C_1$-$C_4$ alkylene. In embodiments, $L^{3B}$ is a $C_1$-$C_6$ alkylene substituted with —$CF_3$. In embodiments, $L^{3C}$ is a bond. In embodiments, $L^{3C}$ is —O—. In embodiments, $L^{3C}$ is —NH—. In embodiments, $L^{3A}$ is a bond; $L^{3B}$ is unsubstituted methylene; and $L^{3C}$ is —O—.

In embodiments, the symbol $z^2$ is 0. In embodiments, the symbol $z^2$ is 1. In embodiments, the symbol $z^4$ is 0. In embodiments, the symbol $z^4$ is 1. In embodiments, the symbols $z^2$ and $z^4$ are 0. In embodiments, the symbols $z^2$ and $z^4$ are 1. In embodiments, the symbol $z^5$ is 0. In embodiments, the symbol $z^5$ is 1. In embodiments, the symbol $z^5$ is 2. In embodiments, the symbol $z^5$ is 3. In embodiments, the symbol $z^5$ is 4. In embodiments, the symbol $z^6$ is 0. In embodiments, the symbol $z^6$ is 1. In embodiments, the symbol $z^6$ is 2. In embodiments, the symbol $z^6$ is 3. In embodiments, the symbol $z^6$ is 4.

The skilled artisan will appreciate that salts, including pharmaceutically acceptable salts, of the compounds according to Formula (III) may be prepared. Indeed, in certain embodiments of the invention, salts including pharmaceutically-acceptable salts of the compounds according to Formula (III) may be preferred over the respective free or unsalted compound. Accordingly, the invention is further directed to salts, including pharmaceutically-acceptable salts, of the compounds according to Formula (III).

The salts, including pharmaceutically acceptable salts, of the compounds of the invention are readily prepared by those of skill in the art.

As used herein, when enantiomers are isolated in enatiomerically enriched form with unknown absolute chemistry, they are assigned as enantiomer 1 or enantiomer 2 based on their respective chiral HPLC retention times. For the given set of purification conditions by chromatography generally according to the conditions for Examples 11 and 12, the first enantiomer to elute is assigned as "enantiomer 1" and the slower eluting enantiomer is assigned as "enantiomer 2".

Typically, the salts of the present invention are pharmaceutically acceptable salts. Salts encompassed within the term "pharmaceutically acceptable salts" refer to non-toxic salts of the compounds of this invention.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicylate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl)

amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

The compounds according to Formula (III) may contain one or more asymmetric centers (also referred to as a chiral center) and may, therefore, exist as individual enantiomers, diastereomers, or other stereoisomeric forms, or as mixtures thereof. Chiral centers, such as chiral carbon atoms, may be present in a substituent such as an alkyl group. Where the stereochemistry of a chiral center present in a compound of Formula (III), or in any chemical structure illustrated herein, if not specified the structure is intended to encompass all individual stereoisomers and all mixtures thereof. Thus, compounds according to Formula (III) containing one or more chiral centers may be used as racemic mixtures, enantiomerically or diastereomerically enriched mixtures, or as enantiomerically or diastereomerically pure individual stereoisomers.

The compounds according to Formula (III) and pharmaceutically acceptable salts thereof may contain isotopically-labelled compounds, which are identical to those recited in Formula (III) and following, but for the fact that one or more atoms are replaced by an atom having an atomic mass or mass number different from the atomic mass or mass number usually found in nature. Examples of such isotopes include isotopes of hydrogen, carbon, nitrogen, oxygen, phosphorous, sulphur, fluorine, iodine, and chlorine, such as 2H, 3H, 11C, 13C, 14C, 15N, 17O, 18O, 31P, 32P, 35S, 18F, 36Cl, 123I and 125I.

Isotopically-labelled compounds, for example those into which radioactive isotopes such as 3H or 14C are incorporated, are useful in drug and/or substrate tissue distribution assays. Tritiated, i.e., 3H, and carbon-14, i.e., 14C, isotopes are particularly preferred for their ease of preparation and detectability. 11C and 18F isotopes are particularly useful in PET (positron emission tomography), and 125I isotopes are particularly useful in SPECT (single photon emission computerized tomography), both are useful in brain imaging. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds can generally be prepared by substituting a readily available isotopically labelled reagent for a non-isotopically labelled reagent.

The compounds according to Formula (III) may also contain double bonds or other centers of geometric asymmetry. Where the stereochemistry of a center of geometric asymmetry present in Formula (III), or in any chemical structure illustrated herein, is not specified, the structure is intended to encompass the trans (E) geometric isomer, the cis (Z) geometric isomer, and all mixtures thereof. Likewise, all tautomeric forms are also included in Formula (III) whether such tautomers exist in equilibrium or predominately in one form.

The compounds of Formula (III) or salts, including pharmaceutically acceptable salts, thereof may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates wherein water is the solvent that is incorporated into the crystalline lattice are typically referred to as "hydrates." Hydrates include stoichiometric hydrates as well as compositions containing variable amounts of water.

The skilled artisan will further appreciate that certain compounds of Formula (III) or salts, including pharmaceutically acceptable salts thereof that exist in crystalline form, including the various solvates thereof, may exhibit polymorphism (i.e. the capacity to occur in different crystalline structures). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

While aspects for each variable have generally been listed above separately for each variable this invention includes those compounds in which several or each aspect in Formula (III) is selected from each of the aspects listed above. Therefore, this invention is intended to include all combinations of aspects for each variable.

Definitions

"Alkyl" and "alkylene", and derivatives thereof, refer to a hydrocarbon chain having the specified number of "member atoms". Alkyl being monovalent and alkylene being bivalent. For example, $C_1$-$C_6$ alkyl refers to an alkyl group having from 1 to 6 member atoms. Alkyl groups may be saturated, unsaturated, straight or branched. Representative branched alkyl groups have one, two, or three branches. Alkyl and alkylene includes methyl, ethyl, ethylene, propyl (n-propyl and isopropyl), butene, butyl (n-butyl, isobutyl, and t-butyl), pentyl and hexyl.

In an embodiment, "alkyl" and "alkylene" further includes cycloalkyl in the carbon chain, for example —CH$_3$cyclopropane-.

"Alkoxy" refers to an —O-alkyl group wherein "alkyl" is as defined herein. For example, $C_1$-$C_4$alkoxy refers to an alkoxy group having from 1 to 4 member atoms.

Representative branched alkoxy groups have one, two, or three branches. Examples of such groups include methoxy, ethoxy, propoxy, and butoxy.

"Aryl" refers to an aromatic hydrocarbon ring. Aryl groups are monocyclic, bicyclic, and tricyclic ring systems having a total of five to fourteen ring member atoms, wherein at least one ring system is aromatic and wherein each ring in the system contains 3 to 7 member atoms, such as phenyl, naphthalene, tetrahydronaphthalene and biphenyl. Suitably aryl is phenyl.

"Cycloalkyl", unless otherwise defined, refers to a saturated or unsaturated non aromatic hydrocarbon ring having from three to seven carbon atoms. Cycloalkyl groups are monocyclic ring systems. For example, $C_3$-$C_7$ cycloalkyl refers to a cycloalkyl group having from 3 to 7 member atoms. Examples of cycloalkyl as used herein include: cyclopropyl, cyclobutyl, cyclopentyl, cyclohexyl, cyclobutenyl, cyclopentenyl, cyclohexenyl and cycloheptyl.

"Halo" refers to fluoro, chloro, bromo, and iodo.

"Heteroaryl" refers to a monocyclic aromatic 4 to 8 member ring containing 1 to 7 carbon atoms and 1 to 4 heteroatoms, provided that when the number of carbon atoms is 3, the aromatic ring contains at least two heteroatoms, or to such aromatic ring fused to one or more rings, such as heteroaryl rings, aryl rings, heterocyclic rings, cycloalkyl rings. Heteroaryl groups containing more than one heteroatom may contain different heteroatoms. Heteroaryl includes but is not limited to: benzoimidazolyl, benzothiazolyl, benzothiazolyl, benzothiophenyl, benzopyrazinyl, benzotriazolyl, benzotriazinyl, benzo[1,4]dioxanyl, benzofuranyl, 9H-a-carbolinyl, cinnolinyl, furanyl, pyrazolyl, imidazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolopyrimidinyl, pyrazolopyridinyl, pyrrolizinyl, pyrimidyl, isothiazolyl, furazanyl, pyrimidinyl, tetrazinyl, isoxazolyl, quinoxalinyl, quinazolinyl, quinolinyl, quinolizinyl, thienyl, thiophenyl, triazolyl, triazinyl, tetrazolopyrimidinyl, triazolopyrimidinyl, tetrazolyl, thiazolyl and thiazolidinyl. Suitably heteroaryl is selected from: pyrazolyl, imidazolyl, oxazolyl and thienyl. Suitably heteroaryl is a pyridyl group or an imidazolyl group. Suitably heteroaryl is a pyridyl.

"Heterocycloalkyl" refers to a saturated or unsaturated non-aromatic ring containing 4 to 12 member atoms, of which 1 to 11 are carbon atoms and from 1 to 6 are heteroatoms. Heterocycloalkyl groups containing more than one heteroatom may contain different heteroatoms. Heterocycloalkyl groups are monocyclic ring systems or a monocyclic ring fused with an aryl ring or to a heteroaryl ring having from 3 to 6 member atoms.

Heterocycloalkyl includes: pyrrolidinyl, tetrahydrofuranyl, dihydrofuranyl, pyranyl, tetrahydropyranyl, dihydropyranyl, tetrahydrothienyl, pyrazolidinyl, oxazolidinyl, oxetanyl, thiazolidinyl, piperidinyl, homopiperidinyl, piperazinyl, morpholinyl, thiamorpholinyl, 1,3-dioxolanyl, 1,3-dioxanyl, 1,4-dioxanyl, 1,3-oxathiolanyl, 1,3-oxathianyl, 1,3-dithianyl, 1,3oxazolidin-2-one, hexahydro-1H-azepin, 4,5,6,7, tetrahydro-1H-benzimidazol, piperidinyl, 1,2,3,6-tetrahydro-pyridinyl and azetidinyl. Suitably, "heterocycloalkyl" includes: piperidine, tetrahydrofuran, tetrahydropyran and pyrrolidine.

"Heteroatom" refers to a nitrogen, sulphur or oxygen atom.

"Heteroalkyl" and "heteroalkylene" by itself or in combination with another term, means, unless otherwise stated, a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. Heteroalkyl being monovalent and heteroalkylene being bivalent. The heteroalkyl and heteroalkylene groups may be taken together with another substituent to form a heterocycloalkyl group. The heteroatom(s) O, N, P, S, and Si may be placed at any interior position of the heteroalkyl or heteroalkylene group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)$_2$, —$CH_2$—S—$CH_2$—$CH_3$, —$CH_2$—$CH_3$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CHN($CH_3$)$_2$, —O—$CH_3$, —O—$CH_2$—$CH_3$, and —CN. Examples include, but are not limited to: —$CH_3$, —$CH_2$—, —$CH_2$—$CH_2$—O—$CH_2$—, $CH_2$—$CH_2$—NH—$CH_2$—, —$CH_2$—$CH_2$—N($CH_3$)$CH_2$—, —$CH_2$—S—$CH_2$—$CH_2$—, —$CH_2$—$CH_2$—, —S(O)—$CH_2$—, —$CH_2$—$CH_2$—S(O)$_2$—$CH_2$—, —CH=CH—O—$CH_2$—, —Si($CH_3$)$_2$$CH_2$—, —N($CH_3$)$CH_2$—, —O—$CH_2$—$CH_2$—$CH_2$—, —$CH_2$—CH=N—$OCH_2$—, —CH=CHN($CH_3$)$CH_2$—, —O—$CH_2$—, and —O—$CH_2$—$CH_2$—. Up to two or three heteroatoms may be consecutive, such as, for example, —$CH_2$—NH—$OCH_3$ and —$CH_2$—O—Si($CH_3$)$_3$.

"Substituted" as used herein, unless otherwise defined, is meant that the subject chemical moiety has from one to nine substituents, suitably from one to five substituents, selected from the group consisting of:

fluoro,
chloro,
bromo,
iodo,
$C_{1-6}$alkyl,
$C_{1-6}$alkyl substituted with from 1 to 6 substituents independently selected from: fluoro, oxo, —OH, —COOH, —$NH_2$, and —CN,
$OC_{1-6}$alkyl,
$OC_{1-6}$alkyl substituted with from 1 to 6 substituents independently selected from: fluoro, oxo, —OH, —COOH, —$NH_2$, and —CN,
mercapto,
—$SR^x$,
  where $R^x$ is selected from $C_{1-6}$alkyl, and $C_{1-6}$alkyl substituted with from 1 to 6 substituents independently selected from: fluoro, oxo, —OH, —COOH, —$NH_2$, and —CN,
—S(O)$R^x$,
  where $R^x$ is selected from $C_{1-6}$alkyl, and $C_{1-6}$alkyl substituted with from 1 to 6 substituents independently selected from: fluoro, oxo, —OH, —COOH, —$NH_2$, and —CN,
—S(O)$_2$H,
—S(O)$_2$$R^x$,
  where $R^x$ is selected from $C_{1-6}$alkyl, and $C_{1-6}$alkyl substituted with from 1 to 6 substituents independently selected from: fluoro, oxo, —OH, —COOH, —$NH_2$, and —CN,
oxo,
hydroxy,
amino,
—$NHR^x$,
  where $R^x$ is selected from $C_{1-6}$alkyl, and $C_{1-6}$alkyl substituted with from 1 to 6 substituents independently selected from: fluoro, oxo, —OH, —COOH, —$NH_2$, and —CN,
—$NR^{x1}R^{x2}$,
  where $R^{x1}$ and $R^{x2}$ are each independently selected from $C_{1-6}$alkyl, and $C_{1-6}$alkyl substituted with from 1 to 6 substituents independently selected from: fluoro, oxo, —OH, —COOH, —$NH_2$, and —CN,
guanidino,
—C(O)OH,
—C(O)$OR^x$, where $R^x$ is selected from $C_{1-6}$alkyl, and $C_{1-6}$alkyl substituted with from 1 to 6 substituents independently selected from: fluoro, oxo, —OH, —COOH, —NH$_2$, and —CN,
—C(O)NH$_2$,
—C(O)NHR$^x$,
where $R^x$ is selected from $C_{1-6}$alkyl, and $C_{1-6}$alkyl substituted with from 1 to 6 substituents independently selected from: fluoro, oxo, —OH, —COOH, —NH$_2$, and —CN,
—C(O)NR$^{x1}$R$^{x2}$,
where $R^{x1}$ and $R^{x2}$ are each independently selected from $C_{1-6}$alkyl, and $C_{1-6}$alkyl substituted with from 1 to 6 substituents independently selected from: fluoro, oxo, —OH, —COOH, —NH$_2$, and —CN,
—S(O)$_2$NH$_2$,
—S(O)$_2$NHR$^x$,
where $R^x$ is selected from $C_{1-6}$alkyl, and $C_{1-6}$alkyl substituted with from 1 to 6 substituents independently selected from: fluoro, oxo, —OH, —COOH, —NH$_2$, and —CN,
—S(O)$_2$NR$^{x1}$R$^{x2}$,
where $R^{x1}$ and $R^{x2}$ are each independently selected from $C_{1-6}$alkyl, and $C_{1-6}$alkyl substituted with from 1 to 6 substituents independently selected from: fluoro, oxo, —OH, —COOH, —NH$_2$, and —CN,
NHS(O)$_2$H,
NHS(O)$_2$R$^x$,
where $R^x$ is selected from $C_{1-6}$alkyl, and $C_{1-6}$alkyl substituted with from 1 to 6 substituents independently selected from: fluoro, oxo, —OH, —COOH, —NH$_2$, and —CN,
—NHC(O)H,
—NHC(O)R$^x$,
where $R^x$ is selected from $C_{1-6}$alkyl, and $C_{1-6}$alkyl substituted with from 1 to 6 substituents independently selected from: fluoro, oxo, —OH, —COOH, —NH$_2$, and —CN,
—NHC(O)NH$_2$,
—NHC(O)NHR$^x$,
where $R^x$ is selected from $C_{1-6}$alkyl, and $C_{1-6}$alkyl substituted with from 1 to 6 substituents independently selected from: fluoro, oxo, —OH, —COOH, —NH$_2$, and —CN,
—NHC(O)NR$^{x1}$R$^{x2}$,
where $R^{x1}$ and $R^{x2}$ are each independently selected from $C_{1-6}$alkyl, and $C_{1-6}$alkyl substituted with from 1 to 6
Substituents independently selected from: fluoro, oxo, —OH, —COOH, —NH$_2$, and —CN,
nitro, and
cyano.

Suitably "substituted" means the subject chemical moiety has from one to four substituents selected from the group consisting of:
fluoro,
chloro,
bromo,
iodo,
$C_{1-4}$alkyl,
$C_{1-4}$alkyl substituted with from 1 to 4 substituents independently selected from: fluoro, oxo, —OH, —COOH, —NH$_2$, and —CN,
OC$_{1-4}$alkyl,
OC$_{1-4}$alkyl substituted with from 1 to 4 substituents independently selected from: fluoro, oxo, —OH, —COOH, —NH$_2$, and —CN,
—SH,
—S(O)$_2$H,
oxo,
hydroxy,
amino,
—NHR$^X$,
where $R^x$ is selected from $C_{1-4}$alkyl, and $C_{1-6}$alkyl substituted one to 4 times by fluoro,
—NR$^{x1}$R$^{x2}$,
where $R^{x1}$ and $R^{x2}$ are each independently selected from $C_{1-4}$alkyl, and $C_{1-4}$alkyl substituted one to four times by fluoro,
guanidino,
—C(O)OH,
—C(O)OR$^x$,
where $R^x$ is selected from $C_{1-4}$alkyl, and $C_{1-4}$alkyl substituted one to four times by fluoro,
—C(O)NH$_2$,
—C(O)NHR$^x$,
where $R^x$ is selected from $C_{1-4}$alkyl, and $C_{1-4}$alkyl substituted one to four times by fluoro,
—C(O)NR$^{x1}$R$^{x2}$,
where $R^{x1}$ and $R^{x2}$ are each independently selected from $C_{1-4}$alkyl, and $C_{1-4}$alkyl substituted one to four times by fluoro,
—S(O)$_2$NH$_2$,
NHS(O)$_2$H,
—NHC(O)H,
—NHC(O)NH$_2$,
nitro, and
cyano.

As used herein the symbols and conventions used in these processes, schemes and examples are consistent with those used in the contemporary scientific literature, for example, the *Journal of the American Chemical Society or the Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

Ac (acetyl);
Ac$_2$O (acetic anhydride);
ACN (acetonitrile);
AIBN (azobis(isobutyronitrile));
BINAP (2,2'-bis(diphenylphosphino)-1,1'-binaphthyl);
BMS (borane—dimethyl sulphide complex);
Bn (benzyl);
Boc (tert-Butoxycarbonyl);
Boc$_2$O (di-tert-butyl dicarbonate);
BOP (Benzotriazole-1-yl-oxy-tris-(dimethylamino)-phosphonium hexafluorophosphate);
CAN (cerric ammonium nitrate);
Cbz (benzyloxycarbonyl);
CSI (chlorosulfonyl isocyanate);
CSF (cesium fluoride);
DABCO (1,4-Diazabicyclo[2.2.2]octane);
DAST (Diethylamino)sulfur trifluoride);
DBU (1,8-Diazabicyclo[5.4.0]undec-7-ene);
DCC (Dicyclohexyl Carbodiimide);
DCE (1,2-dichloroethane);
DCM (dichloromethane);
DDQ (2,3-Dichloro-5,6-dicyano-1,4-benzoquinone);
ATP (adenosine triphosphate);

Bis-pinacolatodiboron (4,4,4',4',5,5,5',5'-Octamethyl-2,2'-bi-1,3,2-dioxaborolane);
BSA (bovine serum albumin);
C18 (refers to 18-carbon alkyl groups on silicon in HPLC stationary phase);
CH$_3$CN (acetonitrile);
Cy (cyclohexyl);
DCM (dichloromethane);
DIPEA (Hunig's base, N-ethyl-N-(1-methylethyl)-2-propanamine);
Dioxane (1,4-dioxane);
DMAP (4-dimethylaminopyridine);
DME (1,2-dimethoxyethane);
DMEDA (N,N'-dimethylethylenediamine);
DMF (N,N-dimethylformamide);
DMSO (dimethylsulfoxide);
DPPA (diphenyl phosphoryl azide);
EDC (N-(3-dimethylaminopropyl)-N'ethylcarbodiimide);
EDTA (ethylenediaminetetraacetic acid);
EtOAc (ethyl acetate);
EtOH (ethanol);
Et$_2$O (diethyl ether);
HEPES (4-(2-hydroxyethyl)-1-piperazine ethane sulfonic acid);
HATU (0-(7-Azabenzotriazol-1-yl)-N,N,N',N'-tetramethyluronium hexafluorophosphate);
HOAt (1-hydroxy-7-azabenzotriazole);
HOBt (1-hydroxybenzotriazole);
HOAc (acetic acid);
HPLC (high pressure liquid chromatography);
HMDS (hexamethyldisilazide);
Hunig's Base (N,N-Diisopropylethylamine);
IPA (isopropyl alcohol);
Indoline (2,3-dihydro-1H-indole);
KHMDS (potassium hexamethyldisilazide);
LAH (lithium aluminum hydride);
LDA (lithium diisopropylamide);
LHMDS (lithium hexamethyldisilazide);
MeOH (methanol);
MTBE (methyl tert-butyl ether);
mCPBA (m-chloroperbezoic acid);
NaHMDS (sodium hexamethyldisilazide);
NBS (N-bromosuccinimide);
PE (petroleum ether);
Pd$_2$(dba)$_3$ (Tris(dibenzylideneacetone)dipalladium(0);
Pd(dppf)Cl$_2$.DCM Complex([1,1'-Bis(diphenylphosphino)ferrocene]dichloropalladium(II).dichloromethane complex);
PyBOP (benzotriazol-1-yl-oxytripyrrolidinophosphonium hexafluorophosphate);
PyBrOP (bromotripyrrolidinophosphonium hexafluorophosphate);
RPHPLC (reverse phase high pressure liquid chromatography);
RT (room temperature);
Sat. (saturated)
SFC (supercritical fluid chromatography);
SGC (silica gel chromatography);
SM (starting material);
TLC (thin layer chromatography);
TEA (triethylamine);
TEMPO (2,2,6,6-Tetramethylpiperidine 1-oxyl, free radical);
TFA (trifluoroacetic acid); and
THF (tetrahydrofuran).

All references to ether are to diethyl ether and brine refers to a saturated aqueous solution of NaCl.

Methods of Use

The compounds according to Formula (III) and pharmaceutically acceptable salts thereof are inhibitors of the ATF4 pathway. Compounds which are inhibitors of the ATF4 pathway are readily identified by exhibiting activity in the ATF4 Cell Based Assay below. These compounds are potentially useful in the treatment of conditions wherein the underlying pathology is attributable to (but not limited to) modulation of the eIF2alpha pathway, for example, neurodegenerative disorders, cancer, cardiovascular and metabolic diseases. Accordingly, in another aspect the invention is directed to methods of treating such conditions.

The Integrated Stress Response (ISR) is a collection of cellular stress response pathways that converge in phosphorylation of the translation initiation factor eIF2α resulting in a reduction in overall translation in cells. Mammalian cells have four eIF2α kinases that phosphorylate this initiation factor in the same residue (serine 51); PERK is activated by the accumulation of unfolded proteins in the endoplasmic reticulum (ER), GCN2 is activated by amino acid starvation, PKR by viral infection and HRI by heme deficiency. Activation of these kinases decreases bulk protein synthesis but it also culminates in increased expression of specific mRNAs that contain uORFs. Two examples of these mRNAs are the transcription factor ATF4 and the pro-apoptotic gene CHOP. Phosphorylation of eIF2α upon stress and the concomitant reduction in protein translation has been shown to both have cytoprotective and cytotoxic effects depending on the cellular context and duration and severity of the stress. An integrated stress response-associated disease is a disease characterized by increased activity in the integrated stress response (e.g. increased phosphorylation of eIF2α by an eIF2α kinase compared to a control such as a subject without the disease). A disease associated with phosphorylation of eIF2α is disease characterized by an increase in phosphorylation of eIF2α relative to a control, such as a subject without the disease.

Activation of PERK occurs upon ER stress and hypoxic conditions and its activation and effect on translation has been shown to be cytoprotective for tumor cells [17]. Adaptation to hypoxia in the tumor microenvironment is critical for survival and metastatic potential. PERK has also been shown to promote cancer proliferation by limiting oxidative DNA damage and death [18, 19]. Moreover, a newly identified PERK inhibitor has been shown to have antitumor activity in a human pancreatic tumor xenograft model [20]. Compounds disclosed herein decrease the viability of cells that are subjected to ER-stress. Thus, pharmacological and acute inhibition of the PERK branch with the compounds disclosed herein results in reduced cellular fitness. During tumor growth, compounds disclosed herein, that block the cytoprotective effects of eIF2α phosphorylation upon stress may prove to be potent anti-proliferative agents.

It is known that under certain stress conditions several eIF2α kinases can be simultaneously activated. For example, during tumor growth, the lack of nutrients and hypoxic conditions are known to both activate GCN2 and PERK. Like PERK, GCN2 and their common target, ATF4, have been proposed to play a cytoprotective role [21]. By blocking signaling by both kinases, compounds disclosed herein may bypass the ability of the ISR to protect cancer cells against the effects of low nutrients and oxygen levels encountered during the growth of the tumor.

Prolonged ER stress leads to the accumulation of CHOP, a pro-apoptotic molecule. In a prion mouse model, overexpression of the phosphatase of eIF2α increased survival of prion-infected mice whereas sustained eIF2α phosphorylation decreased survival [22]. The restoration of protein translation rates during prion disease was shown to rescue synaptic deficits and neuronal loss. The compounds disclosed herein that make cells insensitive to eIF2α phosphorylation sustain protein translation. Compounds disclosed herein could prove potent inhibitors of neuronal cell death in prion disease by blocking the deleterious effects of prolonged eIF2α phosphorylation. Given the prevalence of protein misfolding and activation on the UPR in several neurodegenerative diseases (e.g. Alzheimer's (AD) and Parkinson's (PD)), manipulation of the PERK-eIF2α branch could prevent synaptic failure and neuronal death across the spectrum of these disorders.

Another example of tissue-specific pathology that is linked to heightened eIF2α phosphorylation is the fatal brain disorder, vanishing white matter disease (VWM) or childhood ataxia with CNS hypo-myelination (CACH). This disease has been linked to mutation in eIF2B, the GTP exchange factor that is necessary for eIF2 function in translation [23]. eIF2α phosphorylation inhibits the activity of eIF2B and mutations in this exchange factor that reduce its exchange activity exacerbate the effects of eIF2α phosphorylation. The severe consequences of the CACH mutations point to the dangers of UPR hyper-activation, especially as it pertains to the myelin-producing oligodendrocyte. Small molecules, such as compounds disclosed herein, that block signaling through eIF2α phosphorylation may reduce the deleterious effects of its hyper-activation in VWM.

In another aspect is provided a method of improving long-term memory in a patient, the method including administering a therapeutically effective amount of a compound of Formula (III) to the patient. In embodiments, the patient is human. In embodiments, the patient is a mammal.

In embodiments, the compounds set forth herein are provided as pharmaceutical compositions including the compound and a pharmaceutically acceptable excipient. In embodiments of the method, the compound, or a pharmaceutically acceptable salt thereof, is co-adminstered with a second agent (e.g. therapeutic agent). In embodiments of the method, the compound, or a pharmaceutically acceptable salt thereof, is co-adminstered with a second agent (e.g. therapeutic agent), which is administered in a therapeutically effective amount. In embodiments, the second agent is an agent for improving memory.

Induction of long-term memory (LTM) has been shown to be facilitated by decreased and impaired by increased eIF2α phosphorylation. The data strongly support the notion that under physiological conditions, a decrease in eIF2α phosphorylation constitutes a critical step for the long term synaptic changes required for memory formation and ATF4 has been shown to be an important regulator of these processes [24] [25] [26]. It is not known what the contributions of the different eIF2α kinases to learning is or whether each play a differential role in the different parts of the brain. Regardless of the eIF2α kinase/s responsible for phosphorylation of eIF2α in the brain, compounds disclosed herein that block translation and ATF4 production make them ideal molecules to block the effects of this phosphorylation event on memory. Pharmacological treatment with compounds disclosed herein increase spatial memory and enhance auditory and contextual fear conditioning.

Regulators of translation, such as the compounds of Formula (III), could serve as therapeutic agents that improve memory in human disorders associated with memory loss such as Alzheimer's disease and in other neurological disorders that activate the UPR in neurons and thus could have negative effects on memory consolidation such as Parkinson's disease, Amyotrophic lateral sclerosis and prion diseases. In addition, a mutation in eIF2γ, that disrupts complex integrity linked intellectual disability (intellectual disability syndrome or ID) to impaired translation initiation in humans [27]. Hence, two diseases with impaired eIF2 function, ID and VWM, display distinct phenotypes but both affect mainly the brain and impair learning.

The compounds of Formula (III) are also useful in applications where increasing protein production output is desirable, such as in vitro cell free systems for protein production. In vitro systems have basal levels of eIF2α phosphorylation that reduce translational output [28, 29]. Similarly production of antibodies by hybridomas may also be improved by addition of compounds disclosed herein.

In another aspect is provided a method of increasing protein expression of a cell or in vitro expression system, the method including administering an effective amount of a compound of Formula (III) to the cell or expression system. In embodiments, the method is a method of increasing protein expression by a cell and includes administering an effective amount of a compound of Formula (III) to the cell. In embodiments, the method is a method of increasing protein expression by an in vitro protein expression system and includes administering an effective amount of a compound of Formula (III) to the in vitro (e.g. cell free) protein expression system.

In embodiments, the compounds set forth herein are provided as pharmaceutical compositions including the compound and a pharmaceutically acceptable excipient. In embodiments of the method, the compound, or a pharmaceutically acceptable salt thereof, is co-adminstered with a second agent. In embodiments of the method, the compound, or a pharmaceutically acceptable salt thereof, is co-adminstered with a second agent, which is administered in a therapeutically effective amount. In embodiments, the second agent is an agent for improving protein expression.

Suitably, the present invention relates to a method for treating or lessening the severity of breast cancer, including inflammatory breast cancer, ductal carcinoma, and lobular carcinoma.

Suitably the present invention relates to a method for treating or lessening the severity of colon cancer.

Suitably the present invention relates to a method for treating or lessening the severity of pancreatic cancer, including insulinomas, adenocarcinoma, ductal adenocarcinoma, adenosquamous carcinoma, acinar cell carcinoma, and glucagonoma.

Suitably the present invention relates to a method for treating or lessening the severity of skin cancer, including melanoma, including metastatic melanoma.

Suitably the present invention relates to a method for treating or lessening the severity of lung cancer including small cell lung cancer, non-small cell lung cancer, squamous cell carcinoma, adenocarcinoma, and large cell carcinoma.

Suitably the present invention relates to a method for treating or lessening the severity of cancers selected from the group consisting of brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal adenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), neuroendocrine cancers and testicular cancer.

Suitably the present invention relates to a method for treating or lessening the severity of pre-cancerous syndromes in a mammal, including a human, wherein the pre-cancerous syndrome is selected from: cervical intraepithelial neoplasia, monoclonal gammapathy of unknown significance (MGUS), myelodysplastic syndrome, aplastic anemia, cervical lesions, skin nevi (pre-melanoma), prostatic intraepithleial (intraductal) neoplasia (PIN), Ductal Carcinoma in situ (DCIS), colon polyps and severe hepatitis or cirrhosis.

Suitably the present invention relates to a method for treating or lessening the severity of neurodegenerative diseases/injury, such as Alzheimer's disease, spinal cord injury, traumatic brain injury, ischemic stroke, stroke, diabetes, Parkinson disease, Huntington's disease, Creutzfeldt-Jakob Disease, and related prion diseases, progressive supranuclear palsy, amyotrophic lateral sclerosis, myocardial infarction, cardiovascular disease, inflammation, fibrosis, chronic and acute diseases of the liver, chronic and acute diseases of the lung, chronic and acute diseases of the kidney, chronic traumatic encephalopathy (CTE), neurodegeneration, dementia, cognitive impairment, atherosclerosis, ocular diseases, arrhythmias, in organ transplantation and in the transportation of organs for transplantation.

Suitably the present invention relates to a method for preventing organ damage during and after organ transplantation and in the transportation of organs for transplantation. The method of preventing organ damage during and after organ transplantation will comprise the in vivo administration of a compound of Formula (III). The method of preventing organ damage during the transportation of organs for transplantation will comprise adding a compound of Formula (III) to the solution housing the organ during transportation.

Suitably the present invention relates to a method for treating or lessening the severity of ocular diseases/angiogenesis. The method of treating or lessening the severity of ocular diseases/angiogenesis will comprise the in vivo administration of a compound of Formula (III). In embodiments of methods according to the invention, the disorder of ocular diseases, including vascular leakage can be: edema or neovascularization for any occlusive or inflammatory retinal vascular disease, such as rubeosis irides, neovascular glaucoma, pterygium, vascularized glaucoma filtering blebs, conjunctival papilloma; choroidal neovascularization, such as neovascular age-related macular degeneration (AMD), myopia, prior uveitis, trauma, or idiopathic; macular edema, such as post surgical macular edema, macular edema secondary to uveitis including retinal and/or choroidal inflammation, macular edema secondary to diabetes, and macular edema secondary to retinovascular occlusive disease (i.e. branch and central retinal vein occlusion); retinal neovascularization due to diabetes, such as retinal vein occlusion, uveitis, ocular ischemic syndrome from carotid artery disease, ophthalmic or retinal artery occlusion, sickle cell retinopathy, other ischemic or occlusive neovascular retinopathies, retinopathy of prematurity, or Eales Disease; and genetic disorders, such as VonHippel-Lindau syndrome.

In some embodiments, the neovascular age-related macular degeneration is wet age-related macular degeneration. In other embodiments, the neovascular age-related macular degeneration is dry age-related macular degeneration and the patient is characterized as being at increased risk of developing wet age-related macular degeneration.

The methods of treatment of the invention comprise administering an effective amount of a compound according to Formula (III) or a pharmaceutically acceptable salt, thereof to a patient in need thereof.

The invention also provides a compound according to Formula (III) or a pharmaceutically-acceptable salt thereof for use in medical therapy, and particularly in therapy for: cancer, pre-cancerous syndromes, Alzheimer's disease, spinal cord injury, traumatic brain injury, ischemic stroke, stroke, diabetes, Parkinson disease, Huntington's disease, Creutzfeldt-Jakob Disease, and related prion diseases, progressive supranuclear palsy, amyotrophic lateral sclerosis, myocardial infarction, cardiovascular disease, inflammation, fibrosis, chronic and acute diseases of the liver, chronic and acute diseases of the lung, chronic and acute diseases of the kidney, chronic traumatic encephalopathy (CTE), neurodegeneration, dementia, cognitive impairment, atherosclerosis, ocular diseases, in organ transplantation and arrhythmias. The invention also provides a compound according to Formula (III) or a pharmaceutically-acceptable salt thereof for use in preventing organ damage during the transportation of organs for transplantation. Thus, in further aspect, the invention is directed to the use of a compound according to Formula (III) or a pharmaceutically acceptable salt thereof in the preparation of a medicament for the treatment of a disorder characterized by activation of the UPR, such as cancer.

The methods of treatment of the invention comprise administering a safe and effective amount of a compound of Formula (III), or a pharmaceutically acceptable salt thereof to a mammal, suitably a human, in need thereof.

As used herein, "treating", and derivatives thereof, in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

The term "treating" and derivatives thereof refers to therapeutic therapy. Therapeutic therapy is appropriate to alleviate symptoms or to treat at early signs of disease or its progression. Prophylactic therapy is appropriate when a subject has, for example, a strong family history of neurodegenerative diseases. Prophylactic therapy is appropriate when a subject has, for example, a strong family history of cancer or is otherwise considered at high risk for developing cancer, or when a subject has been exposed to a carcinogen.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of Formula (III), or a pharmaceutically acceptable salt thereof, means an amount of the compound sufficient to treat the patient's condition but low enough to avoid serious side effects (at a reasonable benefit/risk ratio) within the scope of sound medical judgment. A safe and effective amount of the compound will vary with the particular route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient", and derivatives thereof refers to a human or other mammal, suitably a human.

The compounds of Formula (III) or pharmaceutically acceptable salts thereof may be administered by any suitable route of administration, including systemic administration. Systemic administration includes oral administration, and parenteral administration. Parenteral administration refers to routes of administration other than enteral, transdermal, or by inhalation, and is typically by injection or infusion. Parenteral administration includes intravenous, intramuscular, and subcutaneous injection or infusion.

The compounds of Formula (III) or pharmaceutically acceptable salts thereof may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Additionally, the compounds of Formula (III) or pharmaceutically-acceptable salts thereof may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Where a —COOH or —OH group is present, pharmaceutically acceptable esters can be employed, for example methyl, ethyl, and the like for —COOH, and acetate maleate and the like for —OH, and those esters known in the art for modifying solubility or hydrolysis characteristics.

The compounds of Formula (III) and pharmaceutically acceptable salts thereof may be co-administered with at least one other active agent known to be useful in the treatment of cancer or pre-cancerous syndromes.

By the term "co-administration" as used herein is meant either simultaneous administration or any manner of separate sequential administration of an ATF4 pathway inhibiting compound, as described herein, and a further active agent or agents, known to be useful in the treatment of cancer, including chemotherapy and radiation treatment. The term further active agent or agents, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered by injection and another compound may be administered orally.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; cell cycle signaling inhibitors; proteasome inhibitors; and inhibitors of cancer metabolism.

Examples of a further active ingredient or ingredients (anti-neoplastic agent) for use in combination or co-administered with the presently invented ATF4 pathway inhibiting compounds are chemotherapeutic agents.

Suitably, the pharmaceutically active compounds of the invention are used in combination with a VEGFR inhibitor, suitably 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt thereof, which is disclosed and claimed in in International Application No. PCT/US01/49367, having an International filing date of Dec. 19, 2001, International Publication Number WO02/059110 and an International Publication date of Aug. 1, 2002, the entire disclosure of which is hereby incorporated by reference, and which is the compound of Example 69. 5-[[4-[(2,3-dimethyl-2H-indazol-6-yl)methylamino]-2-pyrimidinyl]amino]-2-methylbenzenesulfonamide can be prepared as described in International Application No. PCT/US01/49367.

In one embodiment, the cancer treatment method of the claimed invention includes the co-administration a compound of Formula (III) and/or a pharmaceutically acceptable salt thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, cell cycle signaling inhibitors; proteasome inhibitors; and inhibitors of cancer metabolism.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{64}$C $^{67}$C, $^{89}$Sr, $^{86}$Y, $^{87}$Y, and $^{212}$Bi, optionally conjugated to antibodies directed against tumor antigens.

Additional examples of a further active ingredient or ingredients (anti-neoplastic agent) for use in combination or co-administered with the presently invented ATF4 pathway inhibiting compounds are anti-PD-L1 agents.

Anti-PD-L1 antibodies and methods of making the same are known in the art.

Such antibodies to PD-L1 may be polyclonal or monoclonal, and/or recombinant, and/or humanized.

Exemplary PD-L1 antibodies are disclosed in:
U.S. Pat. No. 8,217,149; Ser. No. 12/633,339;
U.S. Pat. No. 8,383,796; Ser. No. 13/091,936;
U.S. Pat. No. 8,552,154; Ser. No. 13/120,406;
US patent publication No. 20110280877; Ser. No. 13/068,337;
US Patent Publication No. 20130309250; Ser. No. 13/892,671;
WO2013019906;
WO2013079174;
U.S. application Ser. No. 13/511,538 (filed Aug. 7, 2012), which is the US National Phase of International Application No. PCT/US10/58007 (filed 2010); and
U.S. application Ser. No. 13/478,511 (filed May 23, 2012).

Additional exemplary antibodies to PD-L1 (also referred to as CD274 or B7-H1) and methods for use are disclosed in U.S. Pat. No. 7,943,743; US20130034559, WO2014055897, U.S. Pat. Nos. 8,168,179; and 7,595,048. PD-L1 antibodies are in development as immuno-modulatory agents for the treatment of cancer.

In one embodiment, the antibody to PD-L1 is an antibody disclosed in U.S. Pat. No. 8,217,149. In another embodiment, the anti-PD-L1 antibody comprises the CDRs of an antibody disclosed in U.S. Pat. No. 8,217,149.

In another embodiment, the antibody to PD-L1 is an antibody disclosed in U.S. application Ser. No. 13/511,538. In another embodiment, the anti-PD-L1 antibody comprises the CDRs of an antibody disclosed in U.S. application Ser. No. 13/511,538.

In another embodiment, the antibody to PD-L1 is an antibody disclosed in application Ser. No. 13/478,511. In another embodiment, the anti-PD-L1 antibody comprises the CDRs of an antibody disclosed in U.S. application Ser. No. 13/478,511.

In one embodiment, the anti-PD-L1 antibody is BMS-936559 (MDX-1105). In another embodiment, the anti-PD-L1 antibody is MPDL3280A (RG7446). In another embodiment, the anti-PD-L1 antibody is MED14736.

Additional examples of a further active ingredient or ingredients (anti-neoplastic agent) for use in combination or co-administered with the presently invented ATF4 pathway inhibiting compounds are PD-1 antagonist.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any embodiments of the aspects or embodiments of the present invention in which a human individual is to be treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in the any of the aspects of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')2, scFv and Fv fragments.

Examples of mAbs that bind to human PD-1, and useful in the various aspects and embodiments of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Specific anti-human PD-1 mAbs useful as the PD-1 antagonist in any of the aspects and embodiments of the present invention include: MK-3475, a humanized IgG4 mAb with the structure described in *WHO Drug Information*, Vol. 27, No. 2, pages 161-162 (2013) and which comprises the heavy and light chain amino acid sequences shown in FIG. 6; nivolumab, a human IgG4 mAb with the structure described in *WHO Drug Information*, Vol. 27, No. 1, pages 68-69 (2013) and which comprises the heavy and light chain amino acid sequences shown in FIG. 7; the humanized antibodies h409A11, h409A16 and h409A17, which are described in WO2008/156712, and AMP-514, which is being developed by Medimmune.

Other PD-1 antagonists useful in the any of the aspects and embodiments of the present invention include an immunoadhesin that specifically binds to PD-1, and preferably specifically binds to human PD-1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Other examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MED14736, MSB0010718C.

KEYTRUDA/pembrolizumab is an anti-PD-1 antibody marketed for the treatment of lung cancer by Merck. The amino acid sequence of pembrolizumab and methods of using are disclosed in U.S. Pat. No. 8,168,757.

Opdivo/nivolumab is a fully human monoclonal antibody marketed by Bristol Myers Squibb directed against the negative immunoregulatory human cell surface receptor PD-1 (programmed death-1 or programmed cell death-1/PCD-1) with immunopotentiation activity. Nivolumab binds to and blocks the activation of PD-1, an Ig superfamily transmembrane protein, by its ligands PD-L1 and PD-L2, resulting in the activation of T-cells and cell-mediated immune responses against tumor cells or pathogens. Activated PD-1 negatively regulates T-cell activation and effector function through the suppression of P13k/Akt pathway activation. Other names for nivolumab include: BMS-936558, MDX-1106, and ONO-4538. The amino acid sequence for nivolumab and methods of using and making are disclosed in U.S. Pat. No. 8,008,449.

Additional examples of a further active ingredient or ingredients (anti-neoplastic agent) for use in combination or co-administered with the presently invented ATF4 pathway inhibiting compounds are immuno-modulators.

As used herein "immuno-modulators" refer to any substance including monoclonal antibodies that affects the immune system. The ICOS binding proteins of the present invention can be considered immune-modulators. Immuno-modulators can be used as anti-neoplastic agents for the treatment of cancer. For example, immune-modulators include, but are not limited to, anti-CTLA-4 antibodies such as ipilimumab (YERVOY) and anti-PD-1 antibodies (Opdivo/nivolumab and Keytruda/pembrolizumab). Other immuno-modulators include, but are not limited to, OX-40 antibodies, PD-L1 antibodies, LAG3 antibodies, TIM-3 antibodies, 41BB antibodies and GITR antibodies.

Yervoy (ipilimumab) is a fully human CTLA-4 antibody marketed by Bristol Myers Squibb. The protein structure of ipilimumab and methods are using are described in U.S. Pat. Nos. 6,984,720 and 7,605,238.

Suitably, the compounds of the invention are combined with an inhibitor of the activity of the protein kinase R (PKR)-like ER kinase, PERK.

Suitably, the compounds of Formula (III) and pharmaceutically acceptable salts thereof may be co-administered with at least one other active agent known to be useful in the treatment of neurodegenerative diseases/injury.

Suitably, the compounds of Formula (III) and pharmaceutically acceptable salts thereof may be co-administered with at least one other active agent known to be useful in the treatment of diabetes.

Suitably, the compounds of Formula (III) and pharmaceutically acceptable salts thereof may be co-administered with at least one other active agent known to be useful in the treatment of cardiovascular disease.

Suitably, the compounds of Formula (III) and pharmaceutically acceptable salts thereof may be co-administered with at least one other active agent known to be useful in the treatment of ocular diseases.

The compounds described herein can be used in combination with one another, with other active agents known to be useful in treating cancer (e.g. pancreatic cancer, breast cancer, multiple myeloma, or cancers of secretory cells), neurodegenerative diseases, vanishing white matter disease, childhood ataxia with CNS hypo-myelination, and/or intellectual disability syndromes (e.g. associated with impaired function of eIF2 or components in a signal transduction pathway including eIF2), or with adjunctive agents that may not be effective alone, but may contribute to the efficacy of the active agent.

In embodiments, the compounds set forth herein are provided as pharmaceutical compositions including the compound and a pharmaceutically acceptable excipient. In embodiments of the method, the compound, or a pharmaceutically acceptable salt thereof, is co-adminstered with a second agent (e.g. therapeutic agent). In embodiments of the method, the compound, or a pharmaceutically acceptable salt thereof, is co-adminstered with a second agent (e.g. therapeutic agent), which is administered in a therapeutically effective amount. In embodiments of the method, the second agent is an agent for treating cancer (e.g. pancreatic cancer, breast cancer, multiple myeloma, or cancers of secretory cells), neurodegenerative diseases, vanishing white matter disease, childhood ataxia with CNS hypo-myelination, and/or intellectual disability syndromes (e.g. associated with impaired function of eIF2 or components in a signal transduction pathway including eIF2), or an inflammatory disease (e.g. POCD or TBI). In embodiments, the second agent is an anti-cancer agent. In embodiments, the second agent is a chemotherapeutic. In embodiments, the second agent is an agent for improving memory. In embodiments, the second agent is an agent for treating a neurodegenerative disease. In embodiments, the second agent is an agent for treating vanishing white matter disease. In embodiments, the second agent is an agent for treating childhood ataxia with CNS hypo-myelination. In embodiments, the second agent is an agent for treating an intellectual disability syndrome. In embodiments, the second agent is an agent for treating pancreatic cancer. In embodiments, the second agent is an agent for treating breast cancer. In embodiments, the second agent is an agent for treating multiple myeloma. In embodiments, the second agent is an agent for treating myeloma. In embodiments, the second agent is an agent for treating a cancer of a secretory cell. In embodiments, the second agent is an agent for reducing eIF2a phosphorylation. In embodiments, the second agent is an agent for inhibiting a pathway activated by eIF2α phosphorylation. In embodiments, the second agent is an agent for inhibiting the integrated stress response. In embodiments, the second agent is an anti-inflammatory agent.

The term "eIF2alpha" or "eIF2α" refers to the protein "Eukaryotic translation initiation factor 2A". In embodiments, "eIF2alpha" or "eIF2α" refers to the human protein. Included in the term "eIF2alpha" or "eIF2α" are the wild-type and mutant forms of the protein. In embodiments, "eIF2alpha" or "eIF2α" refers to the protein associated with Entrez Gene 83939, OMIM 609234, UniProt Q9BY44, and/or RefSeq (protein) NP 114414.

Suitably, the present invention relates to a method for treating an integrated stress response associated disease in a patient in need of such treatment, the method including administering a therapeutically effective amount of a compound of Formula (III), or a pharmaceutically acceptable salt thereof, to the patient.

Suitably, the integrated stress response-associated disease is cancer. Suitably, the integrated stress response-associated disease is a neurodegenerative disease. Suitably, the integrated stress response-associated disease is vanishing white matter disease. Suitably, the integrated stress response-associated disease is childhood ataxia with CNS hypo-myelination. Suitably, the integrated stress response-associated disease is an intellectual disability syndrome.

Suitably, the present invention relates to a method for treating a disease associated with phosphorylation of eIF2α in a patient in need of such treatment, the method including administering a therapeutically effective amount of a compound of Formula (III), or a pharmaceutically acceptable salt thereof, to the patient.

Suitably, the disease associated with phosphorylation of eIF2 α is cancer. Suitably, the disease associated with phosphorylation of eIF2 α is a neurodegenerative disease. Suitably, the disease associated with phosphorylation of eIF2 α is vanishing white matter disease. Suitably, the disease associated with phosphorylation of eIF2 α is childhood ataxia with CNS hypo-myelination. Suitably, the disease associated with phosphorylation of eIF2 α is an intellectual disability syndrome.

Suitably, the present invention relates to a method for treating a disease selected from the group consisting of cancer, a neurodegenerative disease, vanishing white matter disease, childhood ataxia with CNS hypomyelination, and an intellectual disability syndrome.

Suitably, the present invention relates to a method for treating an inflammatory disease in a patient in need of such treatment, the method including administering a therapeutically effective amount of a compound of Formula (III), or a pharmaceutically acceptable salt thereof, to the patient.

Suitably, the inflammatory disease is associated with neurological inflammation. Suitably, the inflammatory disease is postoperative cognitive dysfunction. Suitably, the inflammatory disease is traumatic brain injury or chronic traumatic encephalopathy (CTE).

In embodiments of the method of treating a disease, the disease is selected from the group consisting of cancer, a neurodegenerative disease, vanishing white matter disease, childhood ataxia with CNS hypo-myelination, and an intellectual disability syndrome. In embodiments of the method of treating a disease, the disease is cancer. In embodiments of the method of treating a disease, the disease is a neurodegenerative disease. In embodiments of the method of treating a disease, the disease is vanishing white matter disease. In embodiments of the method of treating a disease, the disease is childhood ataxia with CNS hypo-myelination. In embodiments of the method of treating a disease, the disease is an intellectual disability syndrome. In embodiments of the method of treating a disease, the disease is associated with phosphorylation of eIF2α. In embodiments of the method of treating a disease, the disease is associated with an eIF2α signaling pathway. In embodiments of the method of treating a disease, the disease is a cancer of a secretory cell type. In embodiments of the method of treating a disease, the disease is pancreatic cancer. In embodiments of the method of treating a disease, the disease is breast cancer. In embodiments of the method of treating a disease, the disease is multiple myeloma. In embodiments of the method of treating a disease, the disease is lymphoma. In embodiments of the method of treating a disease, the disease is leukemia. In embodiments of the method of treating a disease, the disease is a hematopoietic cell cancer.

In embodiments of the method of treating a disease, the disease is Alzheimer's disease. In embodiments of the method of treating a disease, the disease is Amyotrophic lateral sclerosis. In embodiments of the method of treating a disease, the disease is Creutzfeldt-Jakob disease. In embodiments of the method of treating a disease, the disease is frontotemporal dementia. In embodiments of the method of treating a disease, the disease is Gerstmann-Straussler-Scheinker syndrome. In embodiments of the method of treating a disease, the disease is Huntington's disease. In embodiments of the method of treating a disease, the disease is HIV-associated dementia. In embodiments of the method of treating a disease, the disease is kuru. In embodiments of the method of treating a disease, the disease is Lewy body dementia. In embodiments of the method of treating a disease, the disease is Multiple sclerosis. In embodiments of the method of treating a disease, the disease is Parkinson's disease. In embodiments of the method of treating a disease, the disease is a Prion disease.

In embodiments of the method of treating a disease, the disease is an inflammatory disease. In embodiments, the inflammatory disease is postoperative cognitive dysfunction. In embodiments, the inflammatory disease is traumatic brain injury. In embodiments, the inflammatory disease is arthritis. In embodiments, the inflammatory disease is rheumatoid arthritis. In embodiments, the inflammatory disease is psoriatic arthritis. In embodiments, the inflammatory disease is juvenile idiopathic arthritis. In embodiments, the inflammatory disease is multiple sclerosis. In embodiments, the inflammatory disease is systemic lupus erythematosus (SLE). In embodiments, the inflammatory disease is myasthenia gravis. In embodiments, the inflammatory disease is juvenile onset diabetes. In embodiments, the inflammatory disease is diabetes mellitus type 1. In embodiments, the inflammatory disease is Guillain-Barre syndrome. In embodiments, the inflammatory disease is Hashimoto's encephalitis. In embodiments, the inflammatory disease is Hashimoto's thyroiditis. In embodiments, the inflammatory disease is ankylosing spondylitis. In embodiments, the inflammatory disease is psoriasis. In embodiments, the inflammatory disease is Sjogren's syndrome. In embodiments, the inflammatory disease is vasculitis. In embodiments, the inflammatory disease is glomerulonephritis. In embodiments, the inflammatory disease is auto-immune thyroiditis. In embodiments, the inflammatory disease is Behcet's disease. In embodiments, the inflammatory disease is Crohn's disease. In embodiments, the inflammatory disease is ulcerative colitis. In embodiments, the inflammatory disease is bullous pemphigoid. In embodiments, the inflammatory disease is sarcoidosis. In embodiments, the inflammatory disease is ichthyosis. In embodiments, the inflammatory disease is Graves ophthalmopathy. In embodiments, the inflammatory disease is inflammatory bowel disease. In embodiments, the inflammatory disease is Addison's disease. In embodiments, the inflammatory disease is Vitiligo. In embodiments, the inflammatory disease is asthma. In embodiments, the inflammatory disease is allergic asthma. In embodiments, the inflammatory disease is acne vulgaris. In embodiments, the inflammatory disease is celiac disease. In embodiments, the inflammatory disease is chronic prostatitis. In embodiments, the inflammatory disease is inflammatory bowel disease. In embodiments, the inflammatory disease is pelvic inflammatory disease. In embodiments, the inflammatory disease is reperfusion injury. In embodiments, the inflammatory disease is sarcoidosis. In embodiments, the inflammatory disease is transplant rejection. In embodiments, the inflammatory disease is interstitial cystitis. In embodiments, the inflammatory disease is atherosclerosis. In embodiments, the inflammatory disease is atopic dermatitis.

In embodiments, the method of treatment is a method of prevention. For example, a method of treating postsurgical cognitive dysfunction may include preventing postsurgical cognitive dysfunction or a symptom of postsurgical cognitive dysfunction or reducing the severity of a symptom of postsurgical cognitive dysfunction by administering a compound described herein prior to surgery.

In an embodiment, this invention provides a compound of Formula (III), or a pharmaceutically acceptable salt thereof, for use in the treatment of a disease selected from the group consisting of cancer, a neurodegenerative disease, vanishing white matter disease, childhood ataxia with CNS hypomyelination, and an intellectual disability syndrome.

In an embodiment, this invention provides a compound of Formula (III), or a pharmaceutically acceptable salt thereof, for use in the treatment of an integrated stress response associated disease.

In an embodiment, this invention provides a compound of Formula (III), or a pharmaceutically acceptable salt thereof, for use in the treatment of a disease associated with phosphorylation of eIF2α.

In an embodiment, this invention provides for the use of a compound of Formula (III), or a pharmaceutically acceptable salt thereof, in the manufacture of a medicament for the treatment of a disease selected from the group consisting of cancer, a neurodegenerative disease, vanishing white matter disease, childhood ataxia with CNS hypomyelination, and an intellectual disability syndrome.

In an embodiment, this invention provides for the use of a compound of Formula (III), or a pharmaceutically acceptable salt thereof, in the manufacture of a medicament for the treatment an integrated stress response associated disease.

In an embodiment, this invention provides for the use of a compound of Formula (III), or a pharmaceutically acceptable salt thereof, in the manufacture of a medicament for the treatment of a disease associated with phosphorylation of eIF2α.

Compositions

The pharmaceutically active compounds within the scope of this invention are useful as ATF4 pathway inhibitors in mammals, particularly humans, in need thereof.

The present invention therefore provides a method of treating cancer, neurodegeneration and other conditions requiring ATF4 pathway inhibition, which comprises administering an effective amount of a compound of Formula (III) or a pharmaceutically acceptable salt thereof. The compounds of Formula (III) also provide for a method of treating the above indicated disease states because of their demonstrated ability to act as ATF4 pathway inhibitors. The drug may be administered to a patient in need thereof by any conventional route of administration, including, but not limited to, intravenous, intramuscular, oral, topical, subcutaneous, intradermal, intraocular and parenteral. Suitably, a ATF4 pathway inhibitor may be delivered directly to the brain by intrathecal or intraventricular route, or implanted at an appropriate anatomical location within a device or pump that continuously releases the ATF4 pathway inhibiting drug.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical compositions are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001-100 mg/kg of active compound, preferably 0.001-50 mg/kg. When treating a human patient in need of a ATF4 pathway inhibitor, the selected dose is administered preferably from 1-6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages, is preferred. Parenteral administration, at high dosages, however, also can be used when safe and convenient for the patient.

Optimal dosages to be administered may be readily determined by those skilled in the art, and will vary with the particular ATF4 pathway inhibitor in use, the strength of the preparation, the mode of administration, and the advancement of the disease condition. Additional factors depending on the particular patient being treated will result in a need to adjust dosages, including patient age, weight, diet, and time of administration.

When administered to prevent organ damage in the transportation of organs for transplantation, a compound of Formula (III) is added to the solution housing the organ during transportation, suitably in a buffered solution.

The method of this invention of inducing ATF4 pathway inhibitory activity in mammals, including humans, comprises administering to a subject in need of such activity an effective ATF4 pathway inhibiting amount of a pharmaceutically active compound of the present invention.

The invention also provides for the use of a compound of Formula (III) or a pharmaceutically acceptable salt thereof in the manufacture of a medicament for use as a ATF4 pathway inhibitor.

The invention also provides for the use of a compound of Formula (III) or a pharmaceutically acceptable salt thereof in the manufacture of a medicament for use in therapy.

The invention also provides for the use of a compound of Formula (III) or a pharmaceutically acceptable salt thereof in the manufacture of a medicament for use in treating cancer, pre-cancerous syndromes, Alzheimer's disease, spinal cord injury, traumatic brain injury, ischemic stroke, stroke, diabetes, Parkinson disease, Huntington's disease, Creutzfeldt-Jakob Disease, and related prion diseases, progressive supranuclear palsy, amyotrophic lateral sclerosis, myocardial infarction, cardiovascular disease, inflammation, fibrosis, chronic and acute diseases of the liver, chronic and acute diseases of the lung, chronic and acute diseases of the kidney, chronic traumatic encephalopathy (CTE), neurodegeneration, dementia, cognitive impairment, atherosclerosis, ocular diseases, arrhythmias, in organ transplantation and in the transportation of organs for transplantation.

The invention also provides for the use of a compound of Formula (III) or a pharmaceutically acceptable salt thereof in the manufacture of a medicament for use in preventing organ damage during the transportation of organs for transplantation.

The invention also provides for a pharmaceutical composition for use as a ATF4 pathway inhibitor which comprises a compound of Formula (III) or a pharmaceutically acceptable salt thereof and a pharmaceutically acceptable carrier.

The invention also provides for a pharmaceutical composition for use in the treatment of cancer which comprises a compound of Formula (III) or a pharmaceutically acceptable salt thereof and a pharmaceutically acceptable carrier.

In addition, the pharmaceutically active compounds of the present invention can be co-administered with further active ingredients, such as other compounds known to treat cancer, or compounds known to have utility when used in combination with a ATF4 pathway inhibitor.

The invention also provides novel processes and novel intermediates useful in preparing the presently invented compounds.

The invention also provides a pharmaceutical composition comprising from 0.5 to 1,000 mg of a compound of Formula (III) or pharmaceutically acceptable salt thereof and from 0.5 to 1,000 mg of a pharmaceutically acceptable excipient.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Example 1

2-(4-chlorophenoxy)-N-((1-(2-(4-chlorophenoxy)acetyl)pyrolidin-3-yl)methyl)acetamide

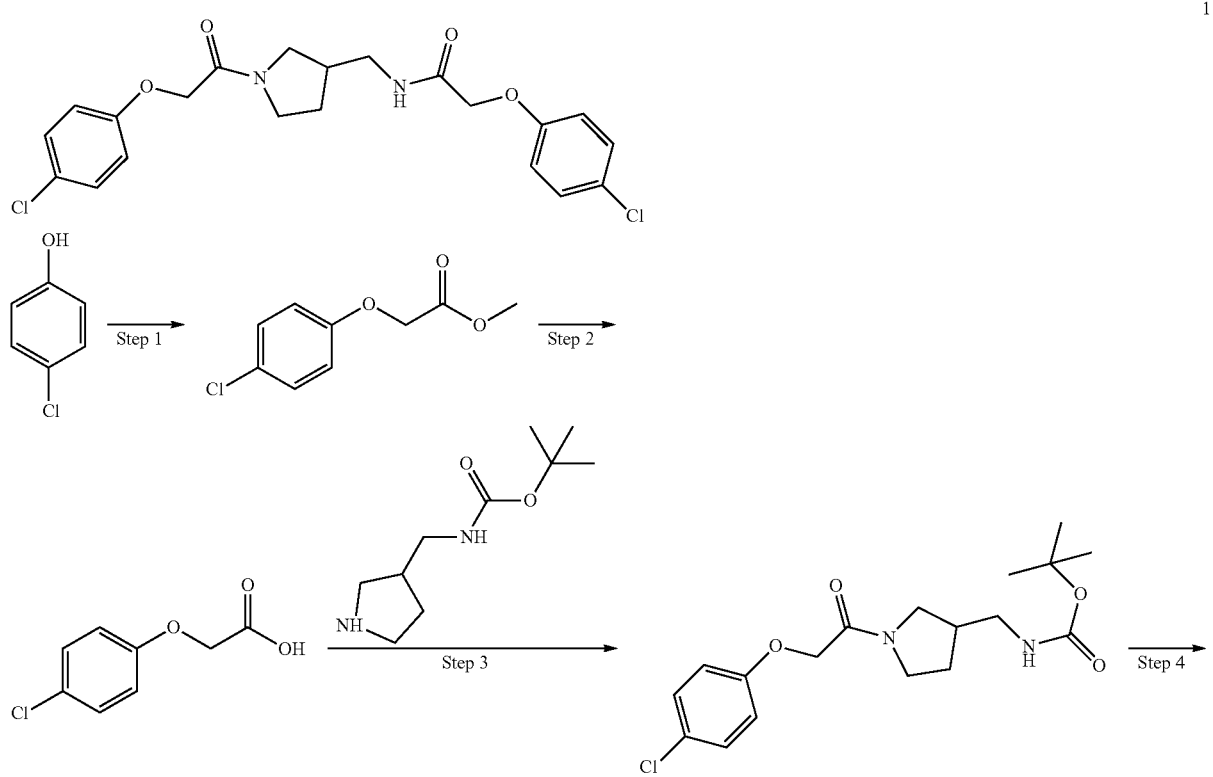

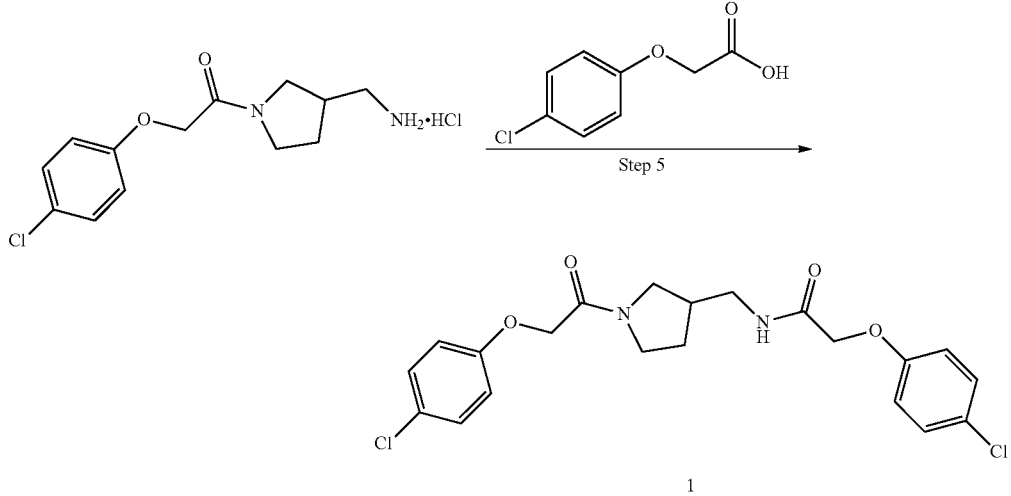

Step 1:

To a solution of 4-chlorophenol (15 g, 116.67 mmol, 1 equiv) in DMF (100 mL) at room temperature was added anhydrous potassium carbonate (24.15 g, 175.01 mmol, 1.5 equiv) portionwise. After stirring for 2 minutes, methyl-2-bromoacetate (13.3 mL, 140.01 mmol, 1.2 equiv) was added. The reaction mixture was heated at 80° C. for 4 h. After consumption of the starting material (TLC, 5% EtOAc in hexane), the reaction mixture was cooled to room temperature, diluted with water (100 mL) and extracted with EtOAc (2×100 mL). The combined organic layer was washed with brine solution (50 mL), dried over anhydrous sodium sulphate, filtered and concentrated en vacuo to give the crude product. The crude product was purified by flash column chromatography (Combiflash) using a silica gel column and the product was eluted at 15% ethyl acetate in hexane. Fractions containing product were concentrated to give methyl 2-(4-chlorophenoxy)acetate (22.5 g, 96.5% yield) as pale yellow liquid. $^1$H NMR (400 MHz, CDCl$_3$): δ ppm 3.67 (s, 3H), 4.78 (s, 2H), 6.91-6.95 (m, 2H), 7.28-7.32 (m, 2H).

Step 2:

To a solution of methyl 2-(4-chlorophenoxy)acetate (22.5 g, 112.15 mmol) in ethanol (100 mL) at 0° C. was added a solution of sodium hydroxide (5.38 g, 134.58 mmol) in water (10 mL). After stirring for 5 minutes at 0° C., the reaction mixture was allowed to warm to room temperature and then refluxed for 2.5 h during which the starting material was completely consumed. Heating was removed and the reaction mixture was allowed to cool down to room temperature. Ethanol was removed en vacuo and the reaction mixture was diluted with water (50 mL) followed by extraction with Et$_2$O (50 mL). The aqueous layer was acidified with 1 N HCl upto pH 3 and the precipitated product was filtered through a cintered funnel, washed with ice-cold water (10 mL) and dried under high vacuum to give 2-(4-chlorophenoxy)acetic acid (20 g, 95.6% yield) as white solid. LCMS (ES) m/z=186.1 [M+H]$^+$. $^1$H NMR (400 MHz, DMSO-d$_6$) δ ppm 4.65 (s, 2H), 6.91 (d, J=9.2 Hz, 2H), 7.29 (d, J=8.8 Hz, 2H), 12.98 (bs, 1H).

Step 3:

To a solution of tert-butyl (pyrrolidin-3-ylmethyl)carbamate (1 g, 5 mmol, 1 equiv) in DCM (20 mL) at 0° C. was added triethylamine (2 mL, 15 mmol, 3 equiv) and 2-(4-chlorophenoxy)acetic acid (1.3 g, 7.5 mmol, 1.5 equiv). After stirring at 0° C. for 5 minutes, T$_3$P (50 wt. % in ethyl acetate) (4.4 mL, 15 mmol, 3 equiv) was added and the reaction mixture was stirred at room temperature for 12 h. The reaction mixture was evaporated to dryness under reduced pressure to give the crude product which was purified by flash column chromatography using a silica gel column and the product was eluted at 50% ethyl acetate in hexane. Fractions containing product were concentrated to give tert-butyl ((1-(2-(4-chlorophenoxy)acetyl)pyrrolidin-3-yl)methyl)carbamate (1.2 g, 65.21% yield) as gummy solid. LCMS (ES) m/z=369.2 [M+H]$^+$. $^1$H NMR (400 MHz, DMSO-d$_6$) δ ppm 1.35 (s, 9H), 1.54-1.57 (m, 1H), 1.59-1.62 (m, 0.5H), 1.64-1.79 (m, 0.5H), 1.83-1.96 (m, 0.5H), 2.17-2.20 (m, 0.5H), 2.91-2.93 (m, 3H), 3.27-3.39 (m, 2H), 3.40-3.41 (m, 1H), 4.67-4.69 (m, 2H), 6.89-6.95 (m, 3H), 7.28 (d, J=8.8 Hz, 2H).

Step 4:

To a solution of tert-butyl ((1-(2-(4-chlorophenoxy)acetyl)pyrrolidin-3-yl)methyl)carbamate (1.2 g, 3.25 mmol, 1 equiv) in DCM (15 mL) at 0° C. was added 4 M HCl in dioxane (8 mL) in a dropwise manner and the reaction mixture allowed to stir at room temperature for 12 h. After consumption of the starting material, solvent was evaporated under reduced pressure. The solid obtained was triturated with Et$_2$O (10 mL). The ether layer was decanted and the solid was dried under high vacuum to give 1-(3-(aminomethyl)pyrrolidin-1-yl)-2-(4-chlorophenoxy)ethanone hydrochloride (0.950 g, 95.6 yield) as off-white solid. LCMS (ES) m/z=269.1 [M+H]$^+$.

Step 5:

To 1-(3-(aminomethyl)pyrrolidin-1-yl)-2-(4-chlorophenoxy)ethanone hydrochloride (0.125 g, 0.4 mmol, 1 equiv) in DCM (25 mL) at 0° C. were added triethylamine (0.14 mL, 1.0 mmol, 2.5 equiv) and 2-(4-chlorophenoxy)acetic acid (0.091 g, 0.49 mmol, 1.2 equiv). After stirring the reaction mixture for 5 minutes at 0° C., T$_3$P (50 wt. % in ethyl acetate) (0.60 mL, 1.0 mmol, 2.5 equiv) was added and the reaction mixture was stirred at room temperature for 18 h. The reaction mixture was then diluted with water (50 mL) and extracted with DCM (100 mL). The organic extract was washed with saturated aqueous NaHCO$_3$ solution (2×50 mL), dried over anhydrous sodium sulphate, filtered and concentrated under reduced pressure to give the crude product which was purified by flash column chromatography using a silica gel column and EtOAc in hexane as eluent. The product was eluted at 50% EtOAc in hexane. Fractions containing the product were concentrated under reduced pressure and dried under high vacuum to give 2-(4-chlorophenoxy)-N-((1-(2-(4-chlorophenoxy)acetyl)pyrrolidin-3-yl)methyl)acetamide (0.04 g, 23% yield) as off-white sticky solid. LCMS (ES) m/z=437.1, 439.1 [M+H]$^+$. $^1$H NMR (400 MHz, DMSO-d$_6$) δ ppm 1.46-1.59 (m, 0.5H), 1.62-1.66 (m, 0.5H), 1.78-1.86 (m, 0.5H), 1.88-1.96 (m, 0.5H), 2.25-2.30 (m, 0.5H), 2.38-2.47 (m, 0.5H), 2.97-3.27 (m, 3H), 3.39-3.55 (m, 3H), 4.48 (s, 2H), 4.67 (d, J=13.6 Hz, 1H), 4.73 (s, 1H), 6.89-6.97 (m, 4H), 7.27-7.32 (m, 4H), 8.22 (d, J=6.0 Hz, 1H).

Example 2

2-(4-chlorophenoxy)-N-((1-(2-(4-chlorophenoxy)ethyl)pyrrolidin-3-yl)methyl)acetamide

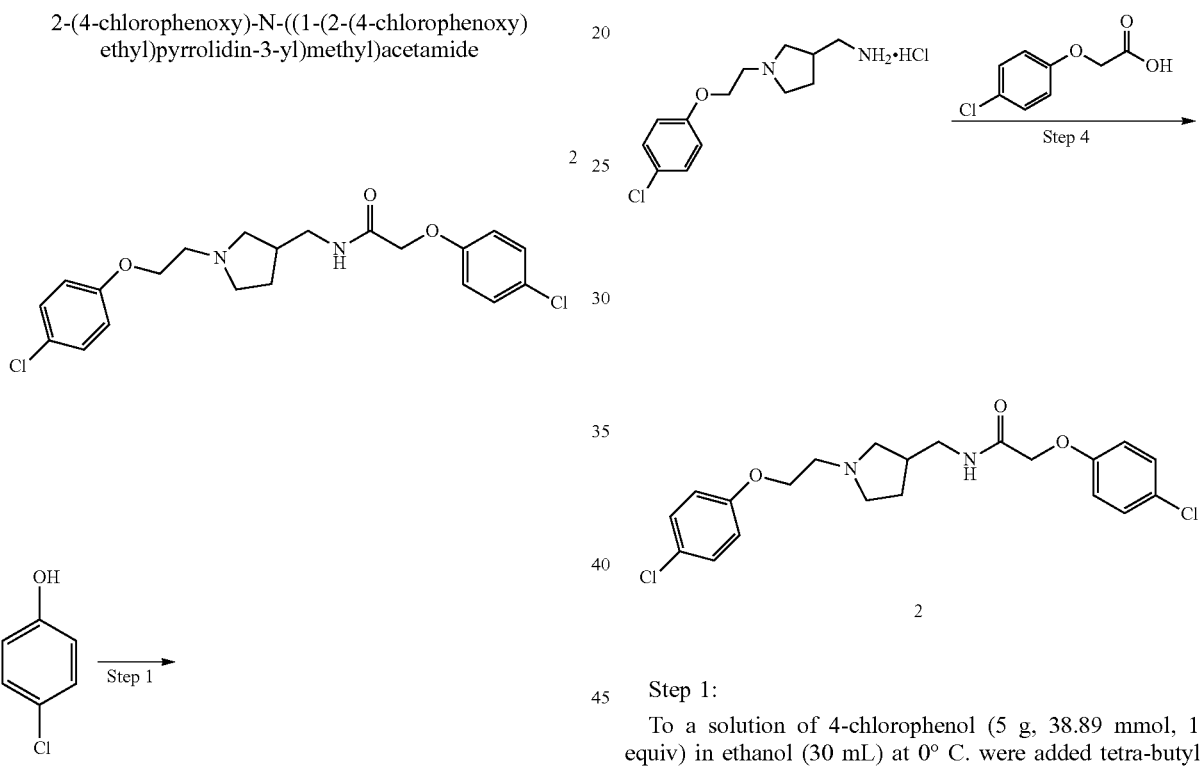

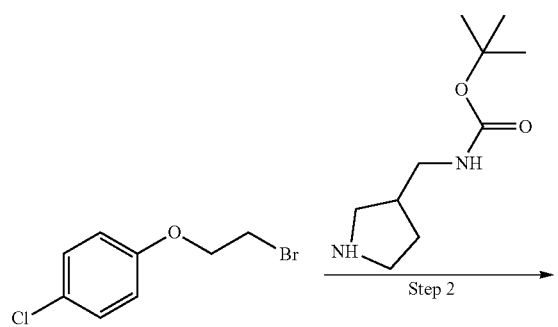

Step 1:

To a solution of 4-chlorophenol (5 g, 38.89 mmol, 1 equiv) in ethanol (30 mL) at 0° C. were added tetra-butyl ammonium bromide (1.25 g, 3.88 mmol, 0.1 equiv) and NaOH (1.55 g, 38.89 mmol, 1 equiv). The reaction mixture was stirred at reflux temperature for 1 h and then cooled to room temperature. 1,2-dibromoethane (10.05 mL, 116.67 mmol, 3 equiv) was added to the reaction mixture and was stirred at reflux temperature for 16 h. After consumption of the starting material, the reaction mixture was cooled to room temperature. Ethanol was evaporated under reduced pressure. The crude mixture was diluted with water (50 mL), extracted with EtOAc (2×40 mL). The combined EtOAc extract was dried over anhydrous sodium sulphate, filtered and concentrated under reduced pressure to the give the crude product which was purified by flash column chromatography using a silica gel column and MeOH in DCM as eluant. The product was eluted at 5% MeOH in DCM as an eluent. Fractions containing the product were concentrated under reduced pressure and dried under high vacuum to give 1-(2-bromoethoxy)-4-chlorobenzene (3 g, 32.96% yield) as colorless liquid. LCMS (ES) m/z=234 [M+H]$^+$, 236 [M$^+$+2

¹H NMR (400 MHz, CDCl₃) δ ppm 3.61 (t, J=6.4 Hz, 2H), 4.26 (t, J=6.8 Hz, 2H), 6.86 (d, J=9.2 Hz, 2H), 7.22-7.25 (m, 2H).

Step 2:

To a solution of tert-butyl (pyrrolidin-3-ylmethyl)carbamate (0.5 g, 2.4 mmol, 1 equiv) in DMF (20 mL) were added cesium carbonate (2.0 g, 6.0 mmol, 2.5 equiv) and 1-(2-bromoethoxy)-4-chlorobenzene (0.7 g, 2.9 mmol, 1.2 equiv). The reaction mixture was heated at 80° C. for 6 h. The reaction mixture was cooled to room temperature, diluted with ice-cold water (100 mL) and extracted with EtOAc (2×100 mL). The combined organic extract was washed with cold water (2×50 mL), dried over anhydrous sodium sulphate, filtered and concentrated under reduced pressure. The crude reaction mixture was purified by flash column chromatography using a silica gel column and EtOAc in hexane as eluant where the product was eluted at 50% EtOAc in hexane. Fractions containing the product were concentrated under reduced pressure and dried under high vacuum to give tert-butyl ((1-(2-(4-chlorophenoxy)ethyl)pyrrolidin-3-yl)methyl)carbamate (0.25 g, 29.37% yield) as pale brown syrup. LCMS (ES) m/z=355.2 [M+H]⁺. ¹H NMR (400 MHz, DMSO-d₆) δ ppm 1.21 (s, 2H), 1.34 (s, 9H), 1.72-1.77 (m, 1H), 2.13-2.25 (m, 2H), 2.47-2.56 (m, 2H), 2.70-2.72 (m, 2H), 2.83-2.86 (m, 2H), 3.99-4.01 (m, 2H), 6.83 (bs, 1H), 6.93 (d, J=8.8 Hz, 2H), 7.28 (d, J=9.2 Hz, 2H).

Step 3:

To a solution of tert-butyl ((1-(2-(4-chlorophenoxy)ethyl)pyrrolidin-3-yl)methyl)carbamate (0.25 g, 0.7 mmol, 1 equiv) in dioxane (5 mL) at 0° C. was added 4 M HCl in dioxane (5 mL) and the reaction mixture allowed to stir at room temperature for 16 h. After consumption of the starting material, solvent was evaporated under reduced pressure. The solid obtained was triturated with Et₂O (2×10 mL). The ether layer was decanted and the solid was dried under high vacuum to give (1-(2-(4-chlorophenoxy)ethyl)pyrrolidin-3-yl)methanamine hydrochloride (0.150 g, 73.5% yield) as off-white solid. LCMS (ES) m/z=255.1 [M+H]⁺.

Step 4:

To (1-(2-(4-chlorophenoxy)ethyl)pyrrolidin-3-yl)methanamine hydrochloride (0.15 g, 0.5 mmol, 1 equiv) taken in DCM (45 mL) at 0° C. were added triethylamine (0.178 mL, 1.27 mmol, 2.5 equiv), 2-(4-chlorophenoxy)acetic acid (0.115 g, 0.61 mmol, 1.2 equiv) and a solution of T₃P (50 wt. % in ethyl acetate) (0.76 mL, 1.27 mmol, 2.5 equiv). The reaction mixture was then allowed to stir at room temperature for 18 h, diluted with DCM (100 mL) and washed with water (50 mL) followed by 10% aqueous NaHCO₃ solution (2×50 mL). The combined organic extract was dried over anhydrous sodium sulphate, filtered and concentrated under reduced pressure to give the crude product. The crude mixture was purified by prep HPLC using a gradient mobile phase (0.1% Ammonia in water:CH₃CN). Fractions containing the product were concentrated to give 2-(4-chlorophenoxy)-N-((1-(2-(4-chlorophenoxy)ethyl)pyrrolidin-3-yl)methyl)acetamide (0.06 g, 27.90% yield) as pale yellow viscous liquid. LCMS (ES) m/z=423.1 [M+H]⁺. ¹H NMR (400 MHz, DMSO-d₆) δ ppm 1.32-1.38 (m, 1H), 1.72-1.80 (m, 1H), 2.25-2.32 (m, 2H), 2.42-2.53 (m, 3H), 2.70 (t, J=5.6 Hz, 2H), 3.07 (t, J=6.0 Hz, 2H), 4.00 (t, J=5.8 Hz, 2H), 4.45 (s, 2H), 6.91-6.95 (m, 4H), 7.29 (d, J=9.4 Hz, 4H), 8.10 (bs, 1H).

Examples 3 to 28

The Compounds of Examples 3 to 28 were prepared generally according to the procedures described above for Examples 1 and 2.

TABLE 1

| Cmpd # | Structure | Name | LCMS m/z [M + H]⁺ | ¹H-NMR (400 MHz, DMSO-d₆) |
|---|---|---|---|---|
| 3 | 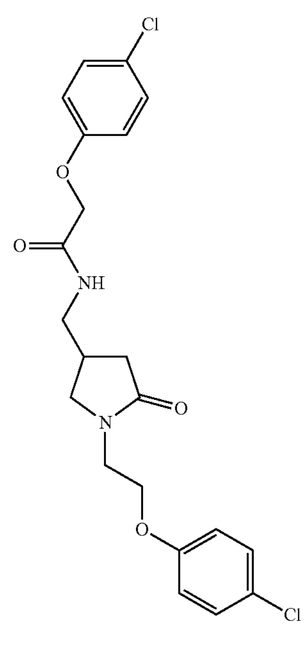 [SMILES: O=C(COc1ccc(Cl)cc1)NCC1CC(=O)N(CCOc2ccc(Cl)cc2)C1] | 2-(4-chlorophenoxy)-N-((1-(2-(4-chlorophenoxy)ethyl)-5-oxopyrrolidin-3-yl)methyl)acetamide | 437.1 | 1.97-2.02 (m, 1 H), 2.25-2.31 (m, 1 H), 3.08-3.91 (m, 4 H), 3.42-3.51 (m, 3 H), 4.01-4.02 (m, 2 H), 4.46 (s, 2 H), 6.93-6.95 (m, 4 H), 7.30 (t, J = 9.6 Hz, 4 H), 8.19-8.28 (m, 1 H). |

TABLE 1-continued

| Cmpd # | Structure | Name | LCMS m/z [M + H]+ | $^1H$-NMR (400 MHz, DMSO-$d_6$) |
|---|---|---|---|---|
| 4 | 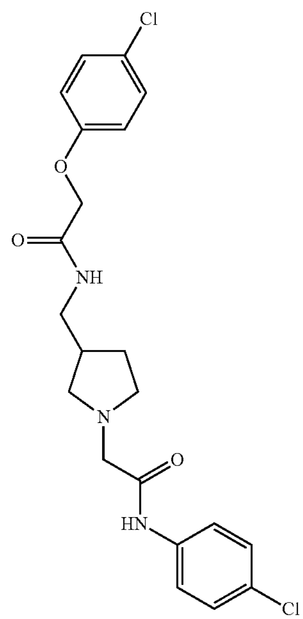 [SMILES: O=C(COc1ccc(Cl)cc1)NCC1CCN(CC(=O)Nc2ccc(Cl)cc2)C1] | 2-(4-chlorophenoxy)-N-((1-(2-((4-chlorophenyl)amino)-2-oxoethyl)pyrrolidin-3-yl)methyl)acetamide | 436.1 | 1.40-1.42 (m, 1 H), 1.82-1.83 (m, 1 H), 2.32-2.33 (m, 2 H), 2.55-2.64 (m, 3 H), 3.10-3.15 (m, 2 H), 3.18 (s, 2 H), 4.45 (s, 2 H), 6.93 (d, J = 8.4 Hz, 2 H), 7.31 (t, J = 8.4 Hz, 4 H), 7.65 (d, J = 8.4 Hz, 2 H), 8.13 (bs, 1 H), 9.75 (s, 1 H). |
| 5 | 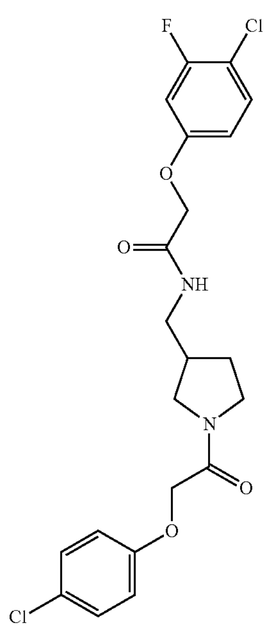 [SMILES: O=C(COc1ccc(Cl)c(F)c1)NCC1CCN(C(=O)COc2ccc(Cl)cc2)C1] | 2-(4-chloro-3-fluorophenoxy)-N-((1-(2-(4-chlorophenoxy)acetyl)pyrrolidin-3-yl)methyl)acetamide | 455.2 | 1.49-1.56 (m, 0.5 H), 1.59-1.64 (m, 0.5 H), 1.81-1.86 (m, 0.5 H), 1.91-1.96 (m, 0.5 H), 2.27-2.30 (m, 0.5 H), 2.39-2.42 (m, 0.5 H), 2.98-3.20 (m, 3.4 H), 3.42-3.51 (m, 2.6 H), 4.48-4.53 (m, 2 H), 4.60-4.69 (m, 2 H), 6.83 (d, J = 8.4 Hz, 1 H), 6.90 (d, J = 6.8 Hz, 2 H), 7.03-7.06 (m, 1 H), 7.28 (d, J = 8.4 Hz, 2 H), 7.47 (d, J = 8.8 Hz, 1 H), 8.23-8.24 (m, 1 H). |

TABLE 1-continued

| Cmpd # | Structure | Name | LCMS m/z [M + H]+ | $^1H$-NMR (400 MHz, DMSO-$d_6$) |
|---|---|---|---|---|
| 6 | 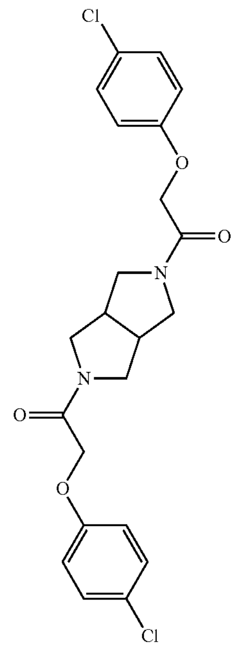 [SMILES: O=C(COc1ccc(Cl)cc1)N1CC2CN(C(=O)COc3ccc(Cl)cc3)CC2C1] | 1,1'-(tetrahydropyrrolo[3,4-c]pyrrole-2,5(1 H,3 H)-diyl)bis(2-(4-chlorophenoxy)ethanone) | 449.3 | 2.80 (bs, 0.5 H), 2.92 (bs, 1 H), 3.02 (bs, 0.5 H), 3.20-3.22 (m, 2 H), 3.38-3.40 (m, 2 H), 3.53-3.58 (m, 2 H), 3.65-3.75 (m, 2 H), 4.72 (s, 4 H), 6.92 (d, J = 9.2 Hz, 4 H), 7.28 (d, J = 8.8 Hz, 4 H). |
| 7 | 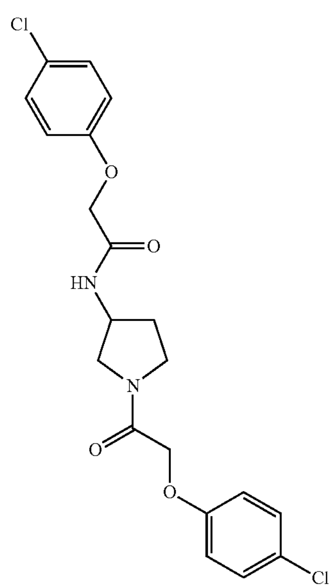 [SMILES: O=C(COc1ccc(Cl)cc1)NC1CCN(C(=O)COc2ccc(Cl)cc2)C1] | 2-(4-chlorophenoxy)-N-(1-(2-(4-chlorophenoxy)acetyl)pyrrolidin-3-yl)acetamide | 423.1 | 1.77-1.82 (m, 0.5 H), 1.87-1.92 (m, 0.5 H), 1.95-2.02 (m, 0.5 H), 2.08-2.13 (m, 0.5 H), 3.21-3.24 (m, 0.5 H), 3.46-3.48 (m, 1.5 H), 3.50-3.55 (m, 1.5 H), 3.68-3.73 (m, 0.5 H), 4.25-4.29 (m, 0.5 H), 4.34-4.39 (m, 0.5 H), 4.42-4.48 (m, 2 H), 4.67-4.71 (m, 2 H), 6.91-6.96 (m, 4 H), 7.28-7.33 (m, 4 H), 8.26-8.31 (m, 1 H). |

TABLE 1-continued

| Cmpd # | Structure | Name | LCMS m/z [M + H]+ | 1H-NMR (400 MHz, DMSO-d6) |
|---|---|---|---|---|
| 8 | 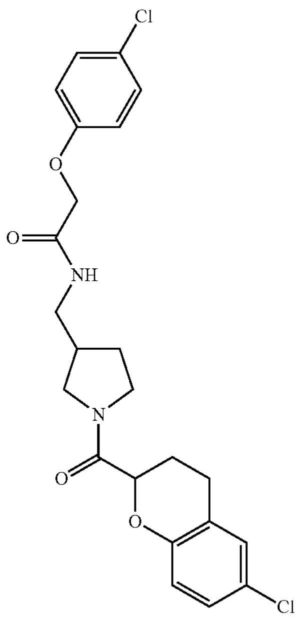 [SMILES: O=C(COc1ccc(Cl)cc1)NCC1CCN(C(=O)C2CCc3cc(Cl)ccc3O2)C1] | N-((1-(6-chlorochroman-2-carbonyl)pyrrolidin-3-yl)methyl)-2-(4-chlorophenoxy)acetamide | 463.3 | 1.51-1.58 (m, 0.5 H), 1.61-1.65 (m, 0.5 H), 1.82-1.86 (m, 0.5 H), 1.91-1.99 (m, 2.5 H), 2.30-2.37 (m, 0.5 H), 2.40-2.48 (m, 0.5 H), 2.73 (s, 2 H), 2.99-3.09 (m, 0.5 H), 3.13-3.23 (m, 2.5 H), 3.39-3.48 (m, 2 H), 3.51-3.67 (m, 1 H), 4.48 (s, 2 H), 4.79-4.85 (m, 1 H), 6.77 (d, J = 8.8 Hz, 1 H), 6.94-6.97 (m, 2 H), 7.06-7.11 (m, 2 H), 7.28-7.33 (m, 2 H), 8.22-8.23 (m, 1 H). |
| 9 | 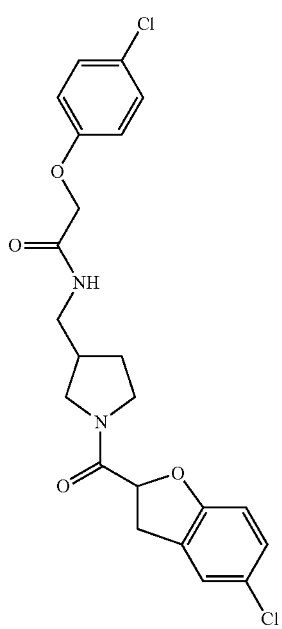 [SMILES: O=C(COc1ccc(Cl)cc1)NCC1CCN(C(=O)C2Cc3cc(Cl)ccc3O2)C1] | N-((1-(5-chloro-2,3-dihydrobenzofuran-2-carbonyl)pyrrolidin-3-yl)methyl)-2-(4-chlorophenoxy)acetamide | 449.2 | 1.51-1.54 (m, 0.5 H), 1.64-1.66 (m, 0.5 H), 1.85 (s, 0.5 H), 1.94 (s, 0.5 H), 2.30-2.48 (m, 1 H), 3.01-3.10 (m, 0.5 H), 3.20-3.27 (m, 2.5 H), 3.33-3.49 (m, 3 H), 3.51-3.68 (m, 2 H), 4.48 (s, 2 H), 5.37-5.49 (m, 1 H), 6.77 (d, J = 8.4 Hz, 1 H), 6.94-6.97 (m, 2 H), 7.10 (d, J = 8.4 Hz, 1 H), 7.24 (s, 1 H), 7.32 (d, J = 8.4 Hz, 2 H), 8.22-8.23 (m, 1 H). |

TABLE 1-continued

| Cmpd # | Structure | Name | LCMS m/z [M + H]+ | $^1H$-NMR (400 MHz, DMSO-$d_6$) |
|---|---|---|---|---|
| 10 | 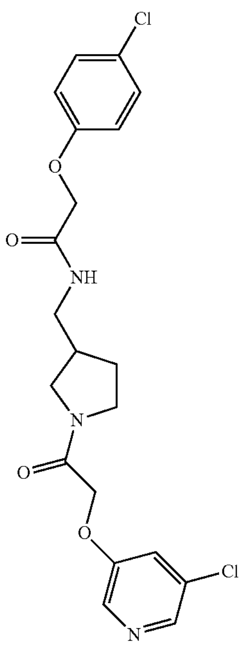 [SMILES: O=C(COc1ccc(Cl)cc1)NCC1CCN(C(=O)COc2cncc(Cl)c2)C1] | 2-(4-chlorophenoxy)-N-((1-(2-((5-chloropyridin-3-yl)oxy)acetyl)pyrrolidin-3-yl)methyl)acetamide | 438.1 | 1.49-1.54 (m, 0.5 H), 1.62-1.65 (m, 0.5 H), 1.82-1.84 (m, 0.5 H), 1.87-1.93 (m, 0.5 H), 2.29 (s, 0.5 H), 2.41-2.47 (m, 0.5 H), 2.98-3.02 (m, 0.5 H), 3.13-3.22 (m, 2.5 H), 3.41-3.49 (m, 3 H), 4.48 (s, 2 H), 4.75-4.89 (m, 2 H), 6.94-6.96 (m, 2 H), 7.31 (d, J = 8.4 Hz, 2 H), 7.53 (s, 1 H), 8.18-8.23 (m, 3 H). |
| 11 | Enantiomer - 1 | 2-(4-chlorophenoxy)-N-((1-(2-((6-chloropyridin-3-yl)oxy)acetyl)pyrrolidin-3-yl)methyl)acetamide | 438.1 | 1.56-1.59 (m, 0.5 H), 1.62-1.66 (m, 0.5 H), 1.82-1.87 (m, 0.5 H), 1.92-1.94 (m, 0.5 H), 2.29-2.32 (m, 0.5 H), 2.42-2.47 (m, 0.5 H), 2.97-3.00 (m, 0.5 H), 3.12-3.18 (m, 2 H), 3.20-3.22 (m, 0.5 H), 3.42-3.50 (m, 3 H), 4.49 (s, 2 H), 4.72-4.86 (m, 2 H), 6.94-6.97 (m, 2 H), 7.31 (d, J = 8.4 Hz, 2 H), 7.36-7.42 (m, 2 H), 8.06 (s, 1 H), 8.21-8.23 (m, 1 H). |

TABLE 1-continued
| Cmpd # | Structure | Name | LCMS m/z [M + H]+ | $^1H$-NMR (400 MHz, DMSO-$d_6$) |
|---|---|---|---|---|
| 12 | 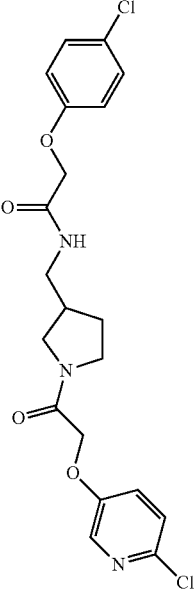<br>Enantiomer - 2 | 2-(4-chlorophenoxy)-N-((1-(2-((6-chloropyridin-3-yl)oxy)acetyl)pyrrolidin-3-yl)methyl)acetamide | 438.1 | 1.49-1.54 (m, 0.5 H), 1.62-1.66 (m, 0.5 H), 1.80-1.85 (m, 0.5 H), 1.91-1.94 (m, 0.5 H), 2.29-2.30 (m, 0.5 H), 2.41-2.42 (m, 0.5 H), 2.97-3.00 (m, 0.5 H), 3.12-3.18 (m, 2 H), 3.20-3.22 (m, 0.5 H), 3.39-3.50 (m, 3 H), 4.48 (s, 2 H), 4.72-4.86 (m, 2 H), 6.95-6.97 (m, 2 H), 7.31 (d, J = 8.4 Hz, 2 H), 7.36-7.42 (m, 2 H), 8.06 (s, 1 H), 8.21-8.23 (m, 1 H). |
| 13 | 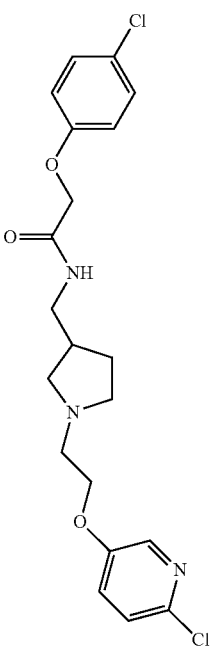 [SMILES: O=C(COc1ccc(Cl)cc1)NCC1CCN(CCOc2ccc(Cl)nc2)C1] | 2-(4-chlorophenoxy)-N-((1-(2-((6-chloropyridin-3-yl)oxy)ethyl)pyrrolidin-3-yl)methyl)acetamide | 424.2 | 1.32-1.38 (m, 1 H), 1.75-1.79 (m, 1 H), 2.27 (s, 2 H), 2.48-2.56 (m, 3 H), 2.74 (s, 2 H), 3.07 (t, J = 6.0 Hz, 2 H), 4.10 (t, J = 6.0 Hz, 2 H), 4.45 (s, 2 H), 6.92-6.96 (m, 2 H), 7.29-7.32 (m, 2 H), 7.38-7.40 (m, 1 H), 7.45-7.47 (m, 1 H), 8.09-8.12 (m, 2 H). |

TABLE 1-continued

| Cmpd # | Structure | Name | LCMS m/z [M + H]+ | $^1H$-NMR (400 MHz, DMSO-d$_6$) |
|---|---|---|---|---|
| 14 | 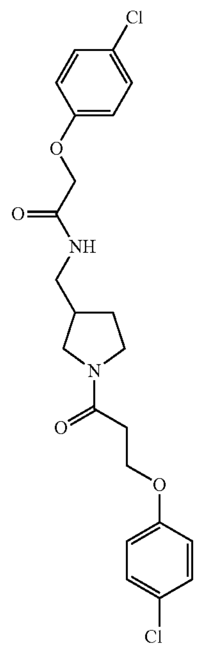 [SMILES: O=C(COc1ccc(Cl)cc1)NCC1CCN(C(=O)CCOc2ccc(Cl)cc2)C1] | 2-(4-chlorophenoxy)-N-((1-(3-(4-chlorophenoxy)propanoyl)pyrrolidin-3-yl)methyl)acetamide | 451.1 | 1.48-1.55 (m, 0.5 H), 1.57-1.64 (m, 0.5 H), 1.81-1.86 (m, 0.5 H), 1.90-1.91 (m, 0.5 H), 2.27-2.35 (m, 0.5 H), 2.38-2.40 (m, 0.5 H), 2.63-2.69 (m, 2 H), 2.95-3.00 (m, 0.5 H), 3.11-3.27 (m, 2.5 H), 3.37-3.50 (m, 3 H), 4.14-4.17 (m, 2 H), 4.48 (s, 2 H), 6.91-6.97 (m, 4 H), 7.27-7.33 (m, 4 H), 8.21 (s, 1 H). |
| 15 | 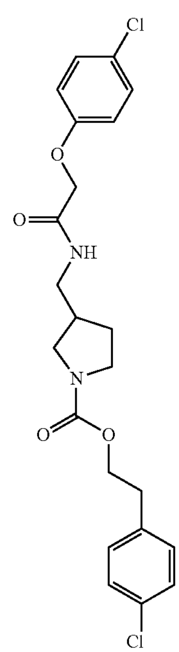 [SMILES: O=C(COc1ccc(Cl)cc1)NCC1CCN(C(=O)OCCc2ccc(Cl)cc2)C1] | 4-chlorophenethyl 3-((2-(4-chlorophenoxy)acetamido)methyl)pyrrolidine-1-carboxylate | 451.0 | 1.49-1.51 (m, 1 H), 1.81 (bs, 1 H), 2.28-2.29 (m, 1 H), 2.82-2.85 (m, 2 H), 2.82-2.94 (m, 1 H), 3.11-3.27 (m, 5 H), 4.10-4.13 (m, 2 H), 4.47 (s, 2 H), 6.95 (d, J = 8.4 Hz, 2 H), 7.23-7.25 (m, 2 H), 7.31 (s, 4 H), 8.18 (s, 1 H). |

TABLE 1-continued

| Cmpd # | Structure | Name | LCMS m/z [M + H]+ | $^1H$-NMR (400 MHz, DMSO-$d_6$) |
|---|---|---|---|---|
| 16 | 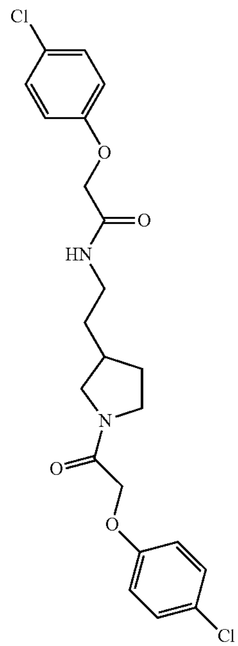 [SMILES: O=C(COc1ccc(Cl)cc1)NCCC1CCN(C(=O)COc2ccc(Cl)cc2)C1] | 2-(4-chlorophenoxy)-N-(2-(1-(2-(4-chlorophenoxy)acetyl)pyrrolidin-3-yl)ethyl)acetamide | 451.0 | 1.35-1.37 (m, 0.5 H), 1.42-1.50 (m, 2.5 H), 1.95-2.00 (m, 1.5 H), 2.09-2.11 (m, 0.5 H), 2.64-2.79 (m, 0.5 H), 2.98-3.02 (m, 0.5 H), 3.13-3.16 (m, 2.5 H), 3.35-3.41 (m, 0.5 H), 3.44-3.46 (m, 0.5 H), 3.54-3.56 (m, 1 H), 3.61-3.63 (m, 0.5 H), 4.45 (s, 2 H), 4.63-4.73 (m, 2 H), 6.89-6.97 (m, 4 H), 7.27-7.33 (m, 4 H), 8.09 (s, 1 H). |
| 17 | 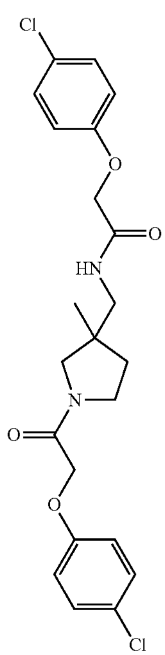 [SMILES: CC1(CNC(=O)COc2ccc(Cl)cc2)CCN(C(=O)COc2ccc(Cl)cc2)C1] | 2-(4-chlorophenoxy)-N-((1-(2-(4-chlorophenoxy)acetyl)-3-methylpyrrolidin-3-yl)methyl)acetamide | 451.0 | 0.93-0.95 (m, 3 H), 1.44-1.56 (m, 1 H), 1.65-1.75 (m, 0.5 H), 1.76-1.81 (m, 0.5 H), ), 3.00-3.11 (m, 2 H), 3.13-3.18 (m, 2 H), 3.33-3.39 (m, 1 H), 3.51 (s, 1 H), 4.53-4.58 (m, 2 H), 4.61-4.73 (m, 2 H), 6.89-6.96 (m, 4 H), 7.26-7.32 (m, 4 H), 8.15-8.18 (m, 1 H). |

TABLE 1-continued
| Cmpd # | Structure | Name | LCMS m/z [M + H]+ | $^1H$-NMR (400 MHz, DMSO-$d_6$) |
|---|---|---|---|---|
| 18 | 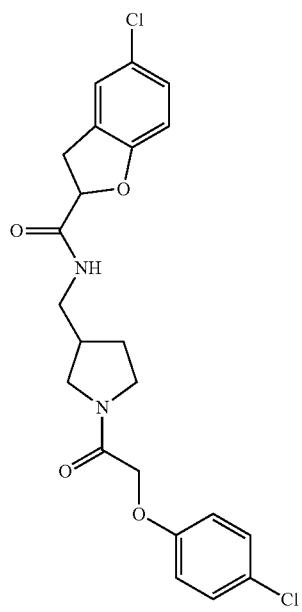 [SMILES: O=C(NCC1CCN(C(=O)COc2ccc(Cl)cc2)C1)C1Cc2cc(Cl)ccc2O1] | 5-chloro-N-((1-(2-(4-chlorophenoxy)acetyl)pyrrolidin-3-yl)methyl)-2,3-dihydrobenzofuran-2-carboxamide | 449.2 | 1.48-1.55 (m, 0.5 H), 1.58-1.65 (m, 0.5 H), 1.79-1.84 (m, 0.5 H), 1.91-1.93 (m, 0.5 H), 2.27-2.32 (m, 0.5 H), 2.41-2.48 (m, 0.5 H), 2.97-3.27 (m, 4 H), 3.38-3.49 (m, 4 H), 4.61-4.68 (m, 2 H), 5.18 (s, 1 H), 6.82 (d, J = 8.4 Hz, 1 H), 6.90 (d, J = 8.4 Hz, 2 H), 7.13 (d, J = 8.4 Hz, 1 H), 7.25-7.29 (m, 3 H), 8.31 (s, 1 H). |
| 19 | 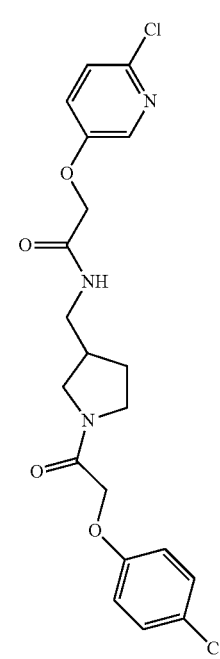 | N((1-(2-(4-chlorophenoxy)acetyl)pyrrolidin-3-yl)methyl)-2-((6-chloropyridin-3-yl)oxy)acetamide | 438.3 | 1.52-1.62 (m, 0.5 H), 1.64-1.82 (m, 0.5 H), 1.84-1.87 (m, 0.5 H), 1.93-1.97 (m, 0.5 H), 2.25-2.32 (m, 0.5 H), 2.40-2.42 (m, 0.5 H), 2.98-3.18 (m, 3 H), 3.32-3.42 (m, 2 H), 3.47-3.53 (m, 1 H), 4.58 (s, 2 H), 4.59-4.65 (m, 1 H), 4.69 (s., 1 H), 6.90 (d, J = 8.4 Hz, 2 H), 7.28 (d, J = 8.4 Hz, 2 H), 7.47-7.42 (m, 2 H), 8.11-8.12 (m, 1 H), 8.26-8.28 (m, 1 H). |

TABLE 1-continued

| Cmpd # | Structure | Name | LCMS m/z [M + H]+ | $^1H$-NMR (400 MHz, DMSO-$d_6$) |
|---|---|---|---|---|
| 20 | 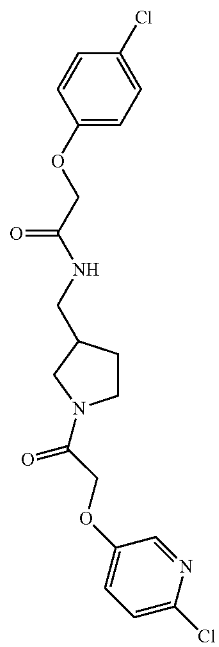 [SMILES: O=C(COc1ccc(Cl)cc1)NCC1CCN(C(=O)COc2ccc(Cl)nc2)C1] | 2-(4-chlorophenoxy)-N-((1-(2-((6-chloropyridin-3-yl)oxy)acetyl)pyrrolidin-3-yl)methyl)acetamide | 438.3 | 1.47-1.52 (m, 0.5 H), 1.54-1.67 (m, 0.5 H), 1.79-1.82 (m, 0.5 H), 1.87-1.98 (m, 0.5 H), 2.26-2.29 (m, 0.5 H), 2.33-2.43 (m, 0.5 H), 2.98-3.03 (m, 0.5 H), 3.08-3.22 (m, 2.5 H), 3.27-3.37 (m, 0.5 H), 3.41-3.54 (m, 2.5 H), 4.76 (s, 2 H), 4.78-4.82 (m, 1 H), 4.86 (s., 1 H), 6.94-6.97 (m, 2 H), 7.32 (d, J = 8 Hz, 2 H), 7.39-7.42 (m, 2 H), 8.07 (br. s, 1 H), 8.22-8.23 (m, 1 H). |
| 21 | 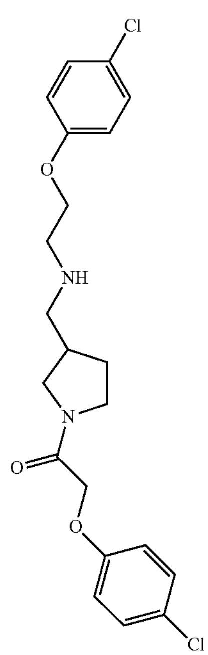 [SMILES: O=C(COc1ccc(Cl)cc1)N1CCC(CNCCOc2ccc(Cl)cc2)C1] | 2-(4-chlorophenoxy)-1-(3-(((2-(4-chlorophenoxy)ethyl)amino)methyl)pyrrolidin-1-yl)ethanone | 423.1 | 1.49-1.60 (m, 0.5 H), 1.65-1.88 (m, 0.5 H), 1.99-2.0 (m, 1 H), 2.17-2.20 (m, 1 H), 2.21-2.30 (m, 1 H), 2.35-3.37 (m, 1 H), 2.55-2.58 (m, 1 H), 2.84 (br. s, 2 H), 2.98-3.03 (m, 0.5 H), 3.12-3.16 (m, 0.5 H), 3.47-3.58 (m, 2.5 H), 3.60-3.62 (m, 0.5 H), 3.98 (s, 2 H), 4.63-4.72 (m, 2 H), 6.89-6.95 (m, 4 H), 7.27-7.29 (m, 4 H). |

TABLE 1-continued

| Cmpd # | Structure | Name | LCMS m/z [M + H]+ | $^1H$-NMR (400 MHz, DMSO-$d_6$) |
|---|---|---|---|---|
| 22 | 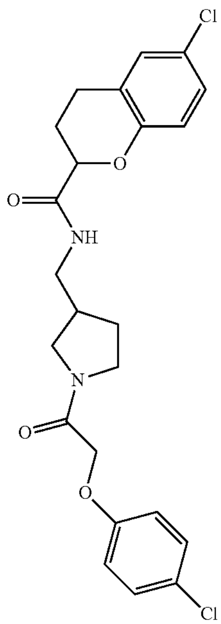 [SMILES: O=C(NCC1CCN(C(=O)COc2ccc(Cl)cc2)C1)C1CCc2cc(Cl)ccc2O1] | 6-chloro-N-((1-(2-(4-chlorophenoxy)acetyl)pyrrolidin-3-yl)methyl)chroman-2-carboxamide | 463.1 | 1.58-1.63 (m, 1 H), 1.81-1.88 (m, 2 H), 2.10 (br. s, 1 H), 2.28-2.48 (m, 1 H), 2.63-2.75 (m, 1 H), 2.77-2.97 (m, 1 H), 3.0-3.02 (m, 0.5 H), 3.13-3.16 (m, 2 H), 3.18-3.20 (m, 0.5 H), 3.39-3.49 (m, 3 H), 4.54-4.55 (m, 1 H), 4.64-4.67 (m, 1 H), 4.68 (s, 1 H), 6.85-6.87 (m, 1 H), 6.91 (d, J = 7.2 Hz, 2 H), 7.11-7.12 (m, 2 H), 7.29 (d, J = 8.4 Hz, 2 H), 8.14-8.15 (m, 1 H). |
| 23 | 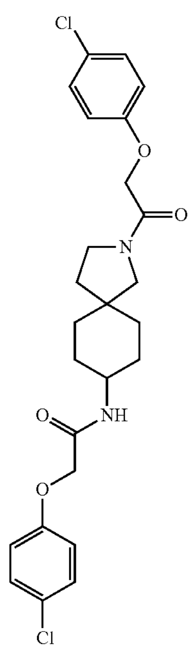 [SMILES: O=C(COc1ccc(Cl)cc1)NC1CCC2(CC1)CCN(C(=O)COc1ccc(Cl)cc1)C2] | 2-(4-chlorophenoxy)-N-(2-(2-(4-chlorophenoxy)acetyl)-2-azaspiro[4.5]decan-8-yl)acetamide | 491.1 | 1.39-1.42 (m, 4 H), 1.45-1.60 (m, 4 H), 1.68 (t, J = 7.0 Hz, 1 H), 1.79 (t, J = 7.0 Hz, 1 H), 3.08 (s, 1 H), 3.22 (s, 1 H), 3.36 (t, J = 6.8 Hz, 1 H), 3.52 (t, J = 7.0 Hz, 1 H), 3.63 (br. s., 1 H), 4.43 (s, 2 H), 4.68 (d, J = 10.8 Hz, 2 H), 6.90 (d, J = 8.4 Hz, 2 H), 6.95 (d, J = 8.4 Hz, 2 H), 7.27-7.33 (m, 4 H), 7.86 (t, J = 9.8 Hz, 1 H) |

TABLE 1-continued

| Cmpd # | Structure | Name | LCMS m/z [M + H]+ | $^1H$-NMR (400 MHz, DMSO-$d_6$) |
|---|---|---|---|---|
| 24 | 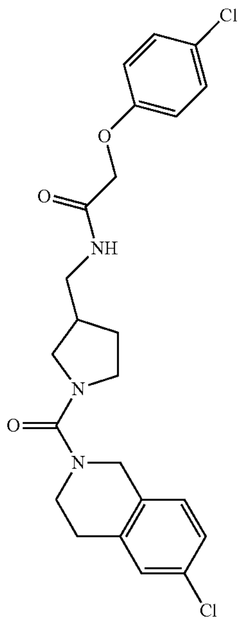 [SMILES: O=C(COc1ccc(Cl)cc1)NCC1CCN(C(=O)N2CCc3cc(Cl)ccc3C2)C1] | N-((1-(6-chloro-1,2,3,4-tetrahydroisoquinoline-2-carbonyl)pyrrolidin-3-yl)methyl)-2-(4-chlorophenoxy)acetamide | 462.1 | 1.21-1.30 (m, 1 H), 1.45-1.50 (m, 1 H), 1.78-1.96 (m, 1 H), 2.24-2.30 (m, 1 H), 2.77-2.83 (m, 2 H), 3.01-3.14 (m, 1 H), 3.16-3.19 (m, 2 H), 3.21-3.33 (m, 3 H), 3.40-3.43 (m, 1 H), 4.28 (s, 2 H), 4.47 (s, 2 H), 6.94 (d, J = 8.8 Hz, 2 H), 7.20-7.14 (m, 3 H), 7.30 (d, J = 9.2 Hz, 2 H), 8.19 (s, 1 H) |
| 25 | 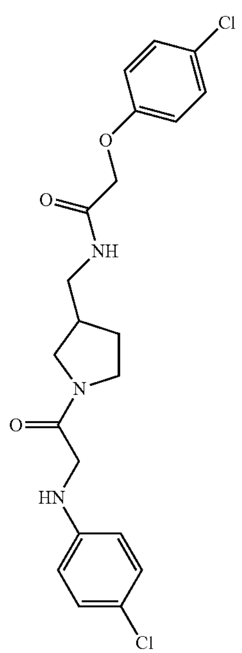 [SMILES: O=C(COc1ccc(Cl)cc1)NCC1CCN(C(=O)CNc2ccc(Cl)cc2)C1] | 2-(4-chlorophenoxy)-N-((1-(2-((4-chlorophenyl)amino)acetyl)pyrrolidin-3-yl)methyl)acetamide) | 436.1 | 1.53-1.57 (m, 0.5 H), 1.62-1.64 (m, 0.5 H), 1.82-1.84 (m, 0.5 H), 1.92-1.94 (m, 0.5 H), 2.30-2.40 (m, 0.5 H), 2.98-3.03 (m, 0.5 H), 3.14 (br. s., 3 H), 3.42-3.51 (m, 3 H), 3.74 (d, J = 13.2 Hz, 2 H), 4.48 (d, J = 4.4 Hz, 2 H), 5.74 (s, 1 H), 6.60 (s, 2 H), 6.96 (s, 2 H), 7.06 (d, J = 7.6 Hz, 2 H), 7.31 (s, 2 H), 8.22 (d, J = 5.2 Hz, 1 H). |

TABLE 1-continued

| Cmpd # | Structure | Name | LCMS m/z [M + H]+ | $^1H$-NMR (400 MHz, DMSO-$d_6$) |
|---|---|---|---|---|
| 26 | 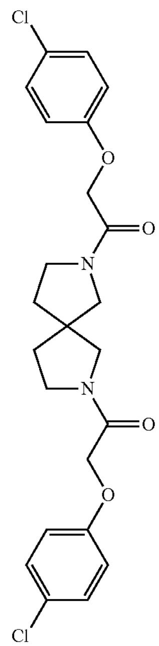 [SMILES: O=C(COc1ccc(Cl)cc1)N1CCC2(CCN(C(=O)COc3ccc(Cl)cc3)C2)C1] | 1,1'-(2,7-diazaspiro[4,4]nonane-2,7-diyl)bis(2-(4-chlorophenoxy)ethanone) | 463.0 | 1.78-1.81 (m, 2 H), 1.90-1.92 (m, 2 H), 3.22-3.35 (m, 2 H), 3.38-3.46 (m, 4 H), 3.56-3.58 (m, 2 H), 4.68-4.77 (m, 4 H), 6.92 (d, J = 8.8 Hz, 4 H), 7.28 (d, J = 8.8 Hz, 4 H). |
| 27 | 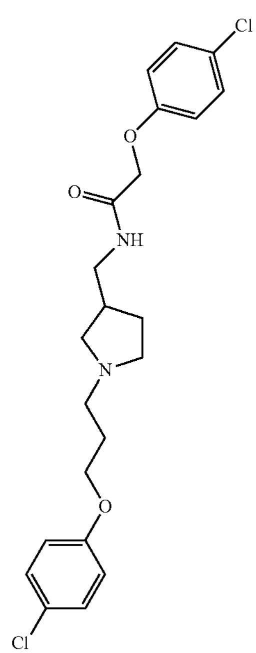 [SMILES: O=C(COc1ccc(Cl)cc1)NCC1CCN(CCCOc2ccc(Cl)cc2)C1] | 2-(4-chlorophenoxy)-N-((1-(3-(4-chlorophenoxy)propyl)pyrrolidin-3-yl)methyl)acetamide | 437.3 | 1.33-1.34 (m, 1 H), 1.78-1.83 (m, 3 H), 2.21-2.41 (m, 7 H), 3.06-3.07 (m, 2 H), 3.97 (t, J = 6.0 Hz, 2 H), 4.45 (s, 2 H), 6.93 (t, J = 9.6 Hz, 4 H), 7.27-7.33 (m, 4 H), 8.10 (bs, 1 H). |

TABLE 1-continued

| Cmpd # | Structure | Name | LCMS m/z [M + H]+ | 1H-NMR (400 MHz, DMSO-d6) |
|---|---|---|---|---|
| 28 | (structure shown) | 2-(4-chlorophenoxy)-N-((1R,5S,6s)-3-(3-(4-chlorophenoxy)propyl)-3-azabicyclo[3.1.0]hexan-6-yl)acetamide | 435.34 | 1.51 (s, 2 H), 1.78 (t, J = 6.4 Hz, 2 H), 2.26 (d, J = 8.0 Hz, 2 H), 2.48 (m, 2 H), 2.83 (s, 1 H), 3.00 (d, J = 8.4 Hz, 2 H), 3.94 (t, J = 6.2 Hz, 2 H), 4.40 (s, 2 H), 6.90-6.94 (m, 4 H), 7.26-7.32 (m, 4 H), 8.03 (d, J = 3.6 Hz, 1 H). |

Example 29

(S)-2-(4-chlorophenoxy)-N-((1-(2-(4-chlorophenoxy)acetyl)pyrrolidin-3-yl)methyl)acetamide

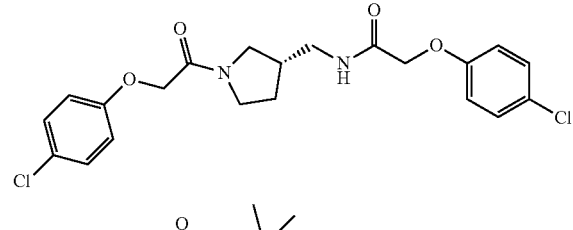

29

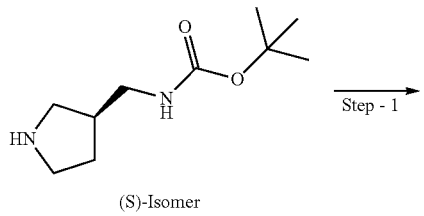

(S)-Isomer

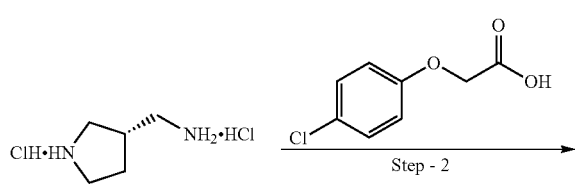
Step - 1

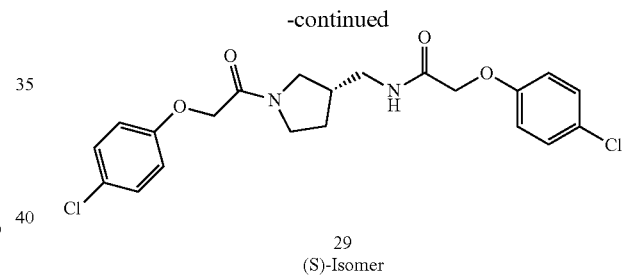

29
(S)-Isomer

Step 1:

To a stirred solution of compound tert-butyl (pyrrolidin-3-ylmethyl)carbamate (0.2 g, 0.99 mmol, 1 eqiuv) in dichloro methane (10 mL) at 0° C., was added 4M HCl in dioxane (10 mL) drop wise manner. After stirring for 5 minutes at 0° C. reaction mixture was allowed to stirred at room temperature for 12 hours. Solvent was evaporated from reaction mixture; obtained solid was washed with di ethyl ether (10 mL). Solid was filtered and dried to get (R)—N-chloro-1-(pyrrolidin-3-yl)methanamine compound with dihydrogen (1:2) hydrochloride (0.17 g, crude) taken for next step. 1H NMR (400 MHz, DMSO-d6): δ 1.63-1.72 (m, 1H), 2.01-2.10 (m, 1H), 2.48-2.58 (m, 1H), 2.86-2.95 (m, 3H), 3.09-3.12 (m, 1H), 3.19 (bs, 1H), 3.27-3.29 (m, 1H), 8.21 (bs, 3H), 9.39-9.46 (m, 2H).

Step 2:

To 2-(4-chlorophenoxy)acetic acid (0.46 g, 2.5 mmol, 2.5 equiv). in DCM (15 mL) at 0° C. was added triethylamine (0.72 mL, 5 mmol, 5 equiv) and was stirred for 5 minutes at 0° C., T3P (50 wt. % in ethyl acetate) (3 mL, 5 mmol, 5 equiv) was added and the reaction mixture stirred at 0° for 10 mins. After that (R)—N-chloro-1-(pyrrolidin-3-yl) methanamine compound with dihydrogen (1:2) hydrochloride (0.17 g, 1 mmol, 1 equiv) was added to the reaction mixture, reaction mixture was stirred at room temperature for 12 hours. The reaction mixture was then diluted with water (10 mL) and extracted with DCM (2×10 mL). Filtered and concentrated under reduced pressure to get crude, obtained Crude product was purified by silica gel chromatography using MeOH in DCM. Product was isolated at 5% MeOH in Dichloro methane as an eluent to give the title compound (S)-2-(4-chlorophenoxy)-N-((1-(2-(4-chlorophenoxy)acetyl)pyrrolidin-3-yl)methyl)acetamide (0.08 g, 18.34% yield) as a gummy solid. LCMS (ES) m/z=437.1 [M+H]$^+$, 1H NMR (400 MHz, DMSO-d$_6$): δ 1.48-1.53 (m, 0.5H), 1.59-1.64 (m, 0.5H), 1.80-1.84 (m, 0.5H), 1.90-1.93 (m, 0.5H), 2.27-2.30 (m, 0.5H), 2.38-2.42 (m, 0.5H), 2.98-3.02 (m, 0.5H), 3.18-3.25 (m, 3H), 3.40-3.51 (m, 2.5H), 4.48 (s, 2H), 4.60-4.69 (m, 2H), 6.89-6.97 (m, 4H), 7.27-7.33 (m, 4H), 8.21-8.23 (m, 1H).

The compound 30 was prepared generally according to the procedure described above for Example 29.

TABLE 2

| Cmpd # | Structure | Name | LCMS m/z [M + H]$^+$ | $^1H$-NMR (400 MHz, DMSO-d$_6$) |
|---|---|---|---|---|
| 29 | 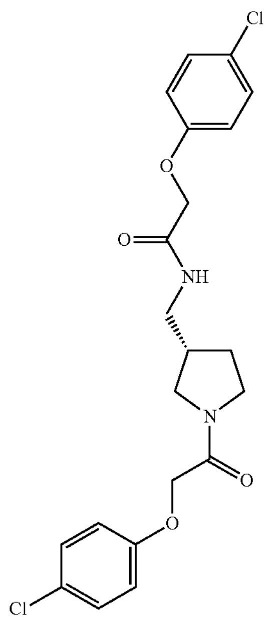 [SMILES: O=C(COc1ccc(Cl)cc1)NC[C@@H]1CCN(C(=O)COc2ccc(Cl)cc2)C1] | (S)-2-(4-chlorophenoxy)-N-((1-(2-(4-chlorophenoxy)acetyl)pyrrolidin-3-yl)methyl)acetamide | 437.1 | 1.48-1.53 (m, 0.5 H), 1.59-1.64 (m, 0.5 H), 1.80-1.84 (m, 0.5 H), 1.90-1.93 (m, 0.5 H), 2.27-2.30 (m, 0.5 H), 2.38-2.42 (m, 0.5 H), 2.98-3.02 (m, 0.5 H), 3.18-3.25 (m, 3 H), 3.40-3.51 (m, 2.5 H), 4.48 (s, 2 H), 4.60-4.69 (m, 2 H), 6.89-6.97 (m, 4 H), 7.27-7.33 (m, 4 H), 8.21-8.23 (m, 1 H). |
| 30 | 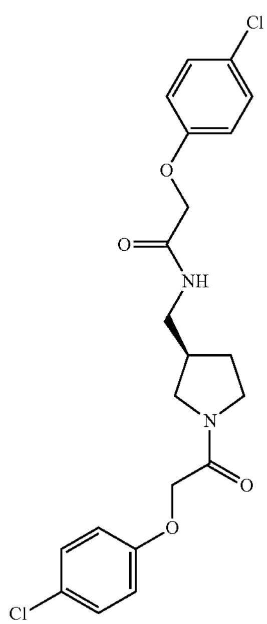 [SMILES: O=C(COc1ccc(Cl)cc1)NC[C@H]1CCN(C(=O)COc2ccc(Cl)cc2)C1] | ((R)-2-(4-chlorophenoxy)-N-((1-(2-(4-chlorophenoxy)acetyl)pyrrolidin-3-yl)methyl)acetamide | 437.1 | 1.48-1.53 (m, 0.5 H), 1.59-1.64 (m, 0.5 H), 1.80-1.85 (m, 0.5 H), 1.90-1.95 (m, 0.5 H), 2.25-2.30 (m, 0.5 H), 2.38-2.42 (m, 0.5 H), 3.01-3.09 (m, 0.5 H), 3.12-3.20 (m, 3 H), 3.40-3.55 (m, 2.5 H), 4.48 (s, 2 H), 4.60-4.69 (m, 2 H), 6.91 (d, J = 7.2 Hz, 2 H), 6.97 (d, J = 6.8 Hz, 2 H), 7.27-7.33 (m, 4 H), 8.21-8.23 (m, 1 H). |

Example 31

2-(4-chlorophenoxy)-N-((1R,5S,6s)-3-(2-(4-chlorophenoxy)acetyl)-3-azabicyclo[3.1.0]hexan-6-yl)acetamide

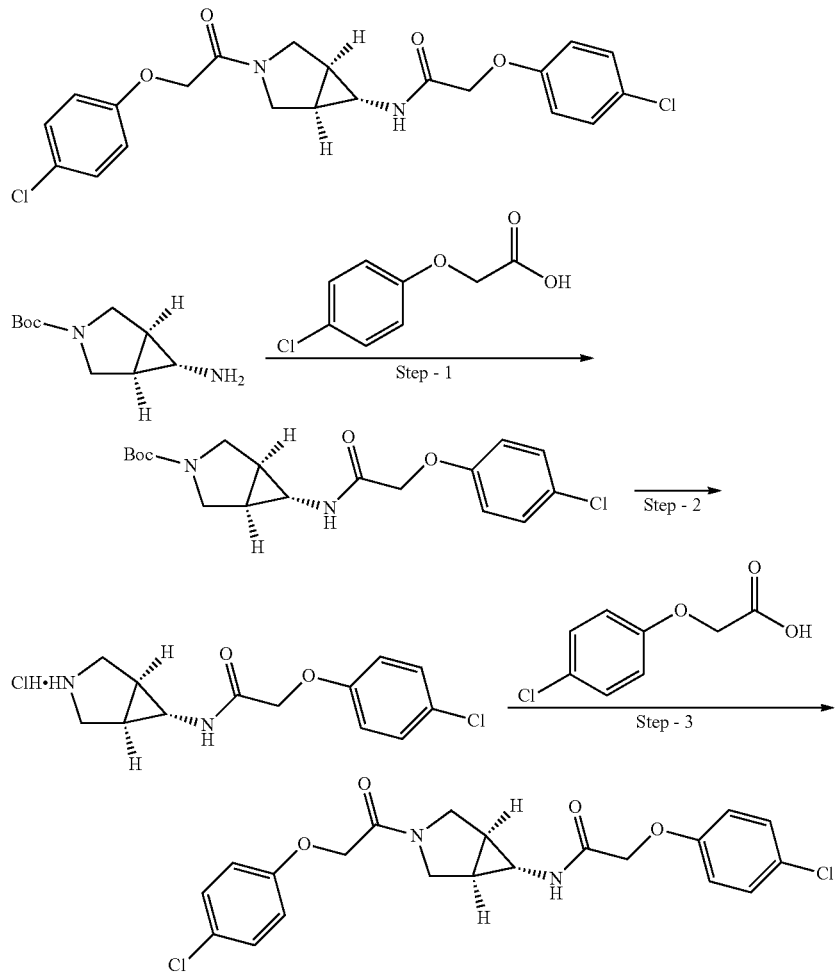

Step 1:
To a stirred solution of (1R,5S,6s)-tert-butyl 6-amino-3-azabicyclo[3.1.0]hexane-3-carboxylate (0.25 g, 1.26 mmol, 1.0 equiv.) in DCM (50 mL) was added triethyl amine (0.89 mL, 6.30 mmol, 5.0 equiv.) dropwise at 0° C. After stirring for 2 minutes compound 2-(4-chlorophenoxy)acetic acid (0.28 g, 1.51 mmol, 1.2 equiv.) and T₃P (50% wt. in ethyl acetate) (1.89 mL, 3.15 mmol, 2.5 equiv.) was added. Then reaction mixture was stirred at room temperature for 16 h. After consumption of the starting material (TLC, 5% MeOH in DCM), reaction mixture was diluted with water (20 mL), extracted with (2×70 mL) DCM. Combined organic layer was washed with sodium bicarbonate solution (2×20 mL), dried over anhydrous sodium sulphate, filtered and concentrated under reduced pressure. Crude was purified by flash column chromatography using 2-4% methanol in dichloromethane to give (1R,5S,6s)-tert-butyl 6-(2-(4-chlorophenoxy)acetamido)-3-azabicyclo[3.1.0]hexane-3-carboxylate (0.38 g, 82.2% yield) as off white solid. LCMS (ES) m/z=366.8 [M+H]⁺ (t-butyl group cleaved mass) ¹H NMR (400 MHz, DMSO-d₆) δ ppm 1.36 (s, 9H), 1.68 (s, 2H), 2.31 (s, 1H), 3.28 (s, 2H), 3.45 (d, J=10.4 Hz, 2H), 4.43 (s, 2H), 6.94 (d, J=9.2 Hz, 2H), 7.32 (d, J=8.8 Hz, 2H), 8.22 (d, J=4.0 Hz, 1H).

Step 2:
To a stirred solution of (1R,5S,6S)-tert-butyl 6-(2-(4-chlorophenoxy)acetamido)-3-azabicyclo[3.1.0]hexane-3-carboxylate (0.38 g, 1.03 mmol, 1.0 equiv.) in DCM (10 mL) was added 4M HCl in dioxane (3.8 mL) dropwise at 0° C. Then reaction mixture was stirred at room temperature for 3 h. After consumption of the starting material (TLC, 10% MeOH in DCM), reaction mixture was concentrated under reduced pressure and the solid obtained was washed with diethyl ether (2×10 mL) and n-pentane (2×10 mL), dried under high vacuum to give N-((1R,5S,6s)-3-azabicyclo[3.1.0]hexan-6-yl)-2-(4-chlorophenoxy)acetamide hydrochloride (0.28 g, crude) as off white solid. LCMS (ES) m/z=267.0 [M+H]⁺ (free amine mass). ¹H NMR (400 MHz, DMSO-d₆) δ ppm 1.89 (s, 2H), 2.83 (d, J=2.4 Hz, 1H), 3.31-3.37 (m, 2H), 3.81 (s, 2H), 4.45 (s, 2H), 6.94 (d, J=8.8 Hz, 2H), 7.32 (d, J=8.8 Hz, 2H), 8.32 (d, J=3.6 Hz, 1H), 8.98 (s, 1H), 9.56 (s, 1H).

Step 3:
To a stirred solution of N-((1R,5S,6S)-3-azabicyclo[3.1.0]hexan-6-yl)-2-(4-chlorophenoxy)acetamide hydrochloride (0.1 g, 0.32 mmol, 1.0 equiv.) in DCM (25 mL) was added triethyl amine (0.23 mL, 1.64 mmol, 5.0 equiv.) dropwise at 0° C. After stirring for 2 minutes compound 2-((6-chloropyridin-3-yl)oxy)acetic acid (0.074 g, 0.39 mmol, 1.2 equiv.) and T₃P (50% wt. in ethyl acetate) (0.49 mL, 0.82 mmol, 2.5 equiv.) was added. Then reaction mixture was stirred at room temperature for 16 h. After consumption of the starting material (TLC, 5% MeOH in DCM), reaction mixture was diluted with water (10 mL), extracted with (2×50 mL) DCM. Combined organic layer was washed with sodium bicarbonate solution (2×10 mL), dried over anhydrous sodium sulphate. Organic layer was filtered and concentrated under reduced pressure. Crude was purified by flash column chromatography using 2-4% methanol in dichloromethane to give 2-(4-chlorophenoxy)-N-((1R,5S,6S)-3-(2-(4-chlorophenoxy)acetyl)-3-azabicyclo[3.1.0]hexan-6-yl)acetamide (0.08 g, 55.9% yield) as off white solid. LCMS (ES) m/z=435.0 [M+H]⁺. ¹H NMR (400 MHz, DMSO-d₆) δ ppm 1.72 (s, 1H), 1.84 (s, 1H), 2.41 (s, 1H), 3.32-3.36 (m, 1H), 3.56-3.58 (m, 1H), 3.59-3.69 (m, 2H), 4.44 (s, 2H), 4.62 (d, J=15.6 Hz, 1H) 4.72 (d, J=15.2 Hz, 1H), 6.89-6.96 (m, 4H), 7.26-7.33 (m, 4H), 8.24 (d, J=3.6 Hz, 1H).

The compounds 32 to 40 were prepared generally according to the procedures described above for Example 31.

TABLE 3

| Cmpd # | Structure | Name | LCMS m/z [M + H]⁺ | $^1H$-NMR (400 MHz, DMSO-$d_6$) |
|---|---|---|---|---|
| 31 | 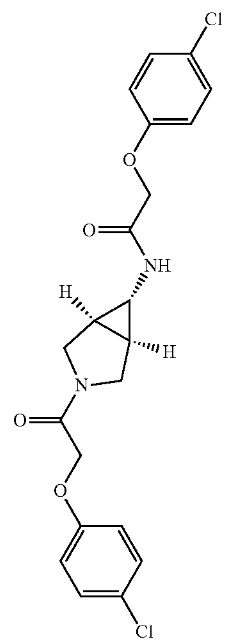 [SMILES: O=C(COc1ccc(Cl)cc1)N[C@H]1[C@@H]2CN(C(=O)COc3ccc(Cl)cc3)C[C@@H]21] | 2-(4-chlorophenoxy)-N-((1R,5S,6s)-3-(2-(4-chlorophenoxy)acetyl)-3-azabicyclo[3.1.0]hexan-6-yl)acetamide | 435.0 | 1.72 (s, 1 H), 1.84 (s, 1 H), 2.41 (s, 1 H), 3.32-3.36 (m, 1 H), 3.56-3.58 (m, 1 H), 3.59-3.69 (m, 2 H), 4.44 (s, 2 H), 4.62 (d, J = 15.6 Hz, 1 H) 4.72 (d, J = 15.2 Hz, 1 H), 6.89-6.96 (m, 4 H), 7.26-7.33 (m, 4 H), 8.24 (d, J = 3.6 Hz, 1 H). |
| 32 | 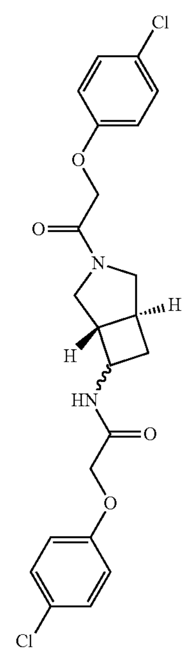 [SMILES: O=C(COc1ccc(Cl)cc1)NC1C[C@@H]2CN(C(=O)COc3ccc(Cl)cc3)C[C@@H]12] | 2-(4-chlorophenoxy)-N-((1S,5R)-3-(2-(4-chlorophenoxy)acetyl)-3-azabicyclo[3.2.0]heptan-6-yl)acetamide | 449.1 | 1.89-1.91 (m, 2 H), 2.07 (bs, 1 H), 2.48-2.53 (m, 2 H), 2.65 (bs, 1 H), 2.80 (d, J = 8.0 Hz, 1 H), 2.86 (d, J = 8.0 Hz, 1 H), 3.94 (m, 1 H), 4.04-4.07 (m, 2 H), 4.42 (s, 2 H), 6.94-6.97 (m, 4 H), 7.28-7.33 (m, 4 H), 8.29-8.30 (m, 1 H). |

TABLE 3-continued
| Cmpd # | Structure | Name | LCMS m/z [M + H]+ | $^1H$-NMR (400 MHz, DMSO-$d_6$) |
|---|---|---|---|---|
| 33 | 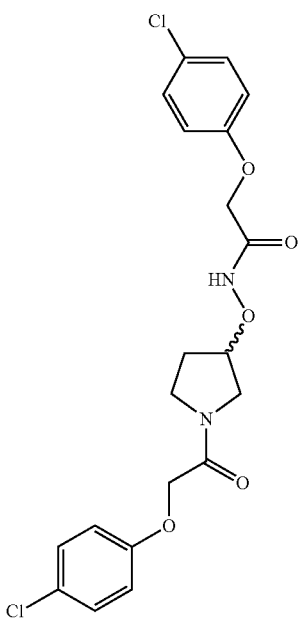 [SMILES: O=C(COc1ccc(Cl)cc1)NOC1CCN(C(=O)COc2ccc(Cl)cc2)C1] | 2-(4-chlorophenoxy)-N-((1-(2-(4-chlorophenoxy)acetyl)pyrrolidin-3-yl)oxy)acetamide | 439.1 | 1.86-2.13 (m, 2 H), 3.31-3.41 (m, 1 H), 3.45-3.56 (m, 2 H), 3.60-3.67 (m, 1 H), 4.51-4.59 (m, 3 H), 4.68-4.78 (m, 2 H), 6.91-6.97 (m, 4 H), 7.27-7.33 (m, 4 H), 11.39 (s, 1 H). |
| 34 | 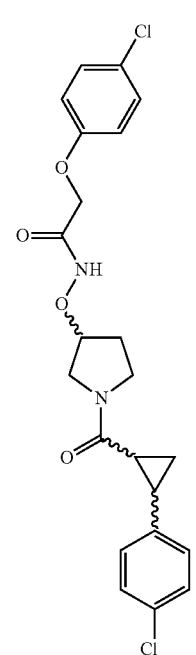 [SMILES: O=C(COc1ccc(Cl)cc1)NOC1CCN(C(=O)C2CC2c2ccc(Cl)cc2)C1] | 2-(4-chlorophenoxy)-N-((1-(2-(4-chlorophenyl)cyclopropane-1-carbonyl)pyrrolidin-3-yl)oxy)acetamide | 449.0 | 1.20-1.25 (m, 1 H), 1.37-1.38 (m, 1 H), 1.88-1.98 (m, 0.5 H), 2.01-2.04 (m, 1.3 H), 2.06-2.09 (m, 1.2 H), 2.30 (bs, 1 H), 3.32-3.37 (m, 0.5 H), 3.49-3.68 (m, 3 H), 3.79-3.82 (m, 0.5 H), 4.50-4.57 (m, 3 H), 6.90-6.97 (m, 2 H), 7.18-7.21 (m, 2 H), 7.28-7.33 (m, 4 H), 11.36-11.41 (m, 1 H). |

TABLE 3-continued

| Cmpd # | Structure | Name | LCMS m/z [M + H]+ | $^1H$-NMR (400 MHz, DMSO-$d_6$) |
|---|---|---|---|---|
| 35 | 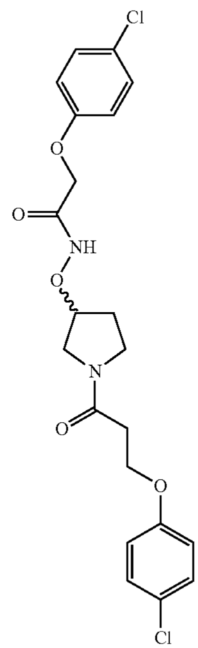 [SMILES: O=C(COc1ccc(Cl)cc1)NOC1CCN(C(=O)CCOc2ccc(Cl)cc2)C1] | 2-(4-chlorophenoxy)-N-((1-(3-(4-chlorophenoxy)propanoyl)pyrrolidin-3-yl)oxy)acetamide | 453.0 | 1.90-2.10 (m, 2 H), 2.65-2.77 (m, 2 H), 3.36-3.45 (m, 1 H), 3.48-3.67 (m, 3 H), 4.17 (s, 2 H), 4.50-4.74 (m, 3 H), 6.92-6.97 (m, 4 H), 7.28-7.34 (m, 4 H), 11.40 (s, 1 H). |
| 36 | 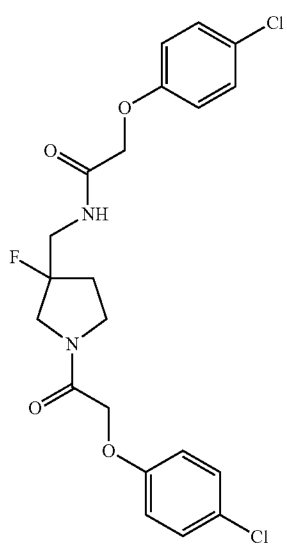 [SMILES: O=C(COc1ccc(Cl)cc1)NCC1(F)CCN(C(=O)COc2ccc(Cl)cc2)C1] | 2-(4-chlorophenoxy)-N-((1-(2-(4-chlorophenoxy)acetyl)-3-fluoropyrrolidin-3-yl)methyl)acetamide | 455.1 | 1.93-2.16 (m, 2 H), 3.32-3.72 (m, 6 H), 4.55 (s, 2 H), 4.59-4.76 (m, 2 H), 6.91-6.97 (m, 4 H), 7.31 (t, J = 9.2 Hz, 4 H), 8.39 (bs, 1 H). |

TABLE 3-continued
| Cmpd # | Structure | Name | LCMS m/z [M + H]+ | $^1H$-NMR (400 MHz, DMSO-$d_6$) |
|---|---|---|---|---|
| 37 | 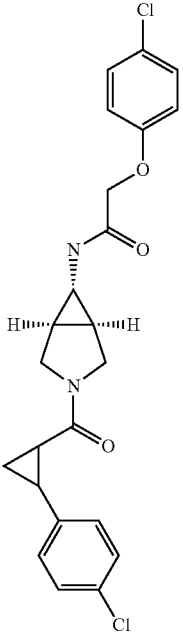 [SMILES: O=C(COc1ccc(Cl)cc1)N[C@H]1[C@@H]2CN(C(=O)C3CC3c3ccc(Cl)cc3)C[C@@H]21] | 2-(4-chlorophenoxy)-N-((1R,5S,6s)-3-(2-(4-chlorophenyl)cyclopropane-1-carbonyl)-3-azabicyclo[3.1.0]hexan-6-yl)acetamide | 445.1 | 1.13-1.22 (m, 1 H), 1.31-1.39 (m, 1 H), 1.73-1.79 (m, 2 H), 2.00-2.06 (m, 1 H), 2.23-2.31 (m, 1 H), 2.36 (bs, 1 H), 3.31-3.35 (m, 1 H), 3.58-3.91 (m, 3 H), 4.43 (d, J = 6.0 Hz, 2 H), 6.92-6.96 (m, 2 H), 7.19 (d, J = 7.2 Hz, 2 H), 7.28-7.33 (m, 4 H), 8.22-8.25 (m, 1 H). |
| 38 | 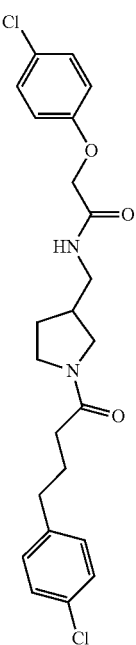 [SMILES: O=C(COc1ccc(Cl)cc1)NCC1CCN(C(=O)CCCc2ccc(Cl)cc2)C1] | 2-(4-chlorophenoxy)-N-((1-(4-(4-chlorophenyl)butanoyl)pyrrolidin-3-yl)methyl)acetamide | 449.2 | 1.45-1.61 (m, 1 H), 1.72-1.87 (m, 3 H), 2.05-2.23 (m, 2 H), 2.25-2.39 (m, 1 H), 2.48-2.56 (m, 2 H), 2.93-3.02 (m, 1 H), 3.05-3.21 (m, 2.5 H), 3.30-3.42 (m, 2.5 H), 4.48 (d, J = 3.6 Hz, 2 H), 6.96 (d, J = 8.8 Hz, 2 H), 7.19 (d, J = 8.4 Hz, 2 H), 7.29-7.33 (m, 4 H), 8.19 (t, J = 5.6 Hz, 1 H). |

TABLE 3-continued

| Cmpd # | Structure | Name | LCMS m/z [M + H]+ | $^1H$-NMR (400 MHz, DMSO-$d_6$) |
|---|---|---|---|---|
| 39 | 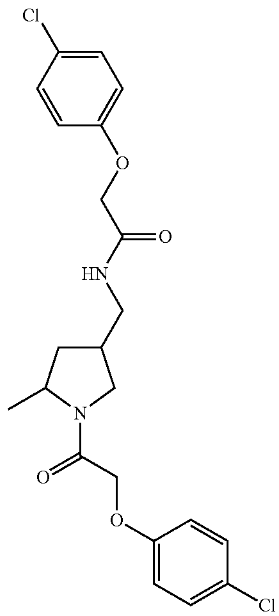 [SMILES: CC1CC(CNC(=O)COc2ccc(Cl)cc2)CN1C(=O)COc1ccc(Cl)cc1] | 2-(4-chlorophenoxy)-N-((1-(2-(4-chlorophenoxy)acetyl)-5-methylpyrrolidin-3-yl)methyl)acetamide | 451.4 | 1.05-1.07 (m, 1.5 H), 1.12-1.14 (m, 1.5 H), 1.21 (bs, 0.5 H), 1.49-1.52 (m, 0.5 H), 1.65-1.68 (m, 1 H), 2.08-2.13 (m, 0.5 H), 2.25 (bs, 0.5 H), 3.02-3.04 (m, 0.5 H), 3.10-3.17 (m, 2.5 H), 3.47-3.50 (m, 0.5 H), 3.58-3.62 (m, 0.5 H), 3.84-3.86 (m, 0.4 H), 3.88-4.01 (m, 0.4 H), 4.15-4.22 (m, 0.2 H), 4.48 (s, 2 H), 4.57-4.82 (m, 2 H), 6.89 (d, J = 8.8 Hz, 2 H), 6.96 (d, J = 7.6 Hz, 2 H), 7.27-7.33 (m, 4 H), 8.18-8.21 (m, 1 H). |
| 40 | 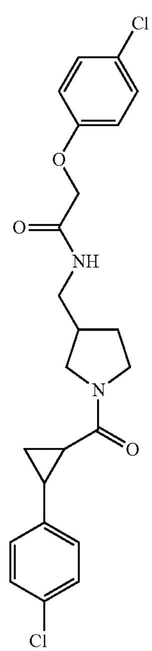 [SMILES: O=C(COc1ccc(Cl)cc1)NCC1CCN(C(=O)C2CC2c2ccc(Cl)cc2)C1] | 2-(4-chlorophenoxy)-N-((1-(2-(4-chlorophenyl)cyclopropanecarbonyl)pyrrolidin-3-yl)methyl)acetamide | 447.1 | 1.18-1.21 (m, 1 H), 1.35-1.38 (m, 1 H), 1.43-1.50 (m, 0.5 H), 1.51-1.59 (m, 0.5 H), 1.81-1.82 (m, 0.5 H), 1.90-1.94 (m, 1 H), 2.03 (s, 0.5 H), 2.30-2.38 (m, 1.5 H), 2.40-2.48 (m, 0.5 H), 2.96-3.03 (m, 0.5 H), 3.10-3.14 (m, 2 H), 3.19-3.27 (m, 0.5 H), 3.39-3.44 (m, 1.5 H), 3.53-3.57 (m, 1 H), 3.62-3.67 (m, 0.5 H), 4.45 (d, J = 10.0 Hz, 2 H), 6.91-6.95 (m, 2 H), 7.18 (d, J = 8.0 Hz, 2 H), 7.28-7.32 (m, 4 H), 8.18 (s, 1 H). |

Example 41

2-(4-chlorophenoxy)-N-((1-(2-(4-chlorophenoxy)ethyl)-5-methylpyrrolidin-3-yl)methyl)acetamide

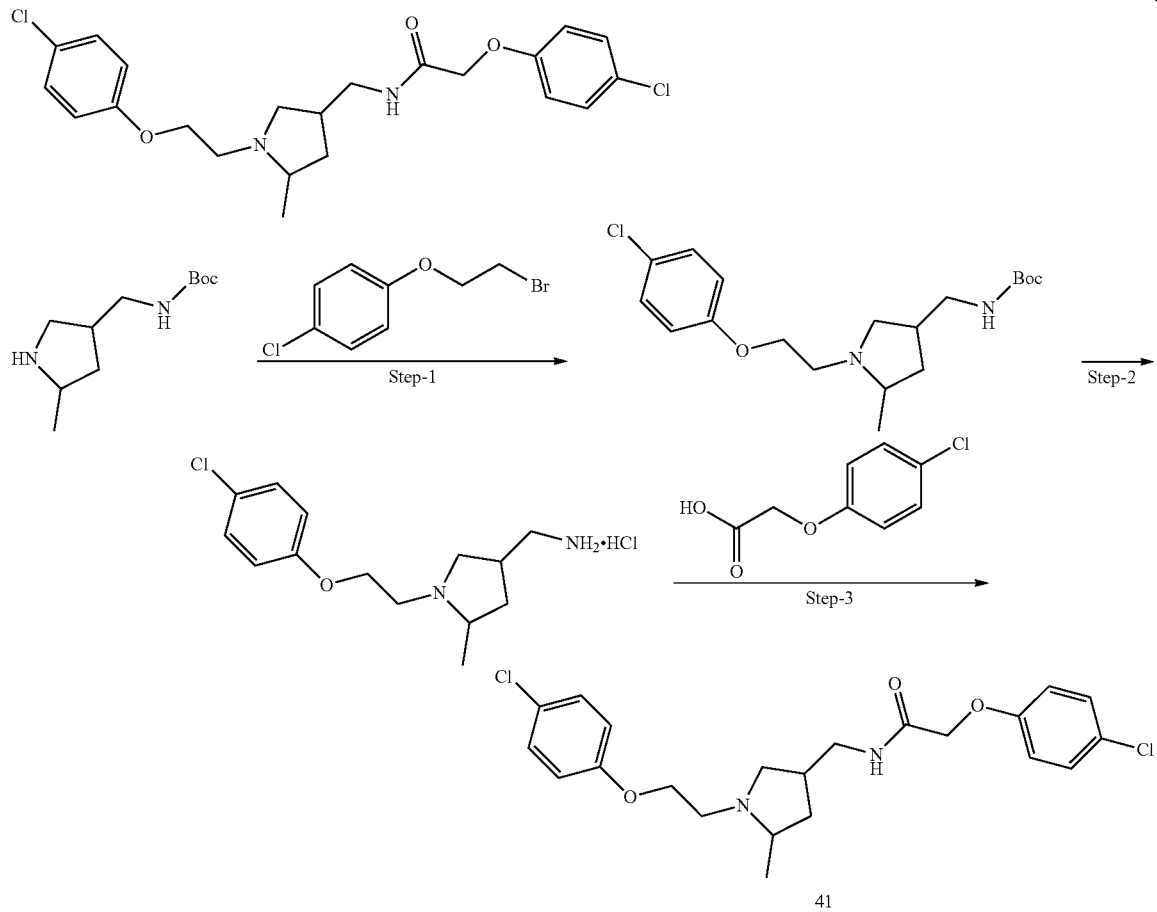

Step 1:

To a stirred solution of tert-butyl ((5-methylpyrrolidin-3-yl)methyl)carbamate (0.2 g, 0.93 mmol, 1.0 equiv.) in ACN (10.0 mL) was added potassium carbonate (0.193 g, 1.39 mmol, 1.5 equiv.), sodium iodide (0.028 g, 0.18 mmol, 0.2 equiv.) and then 1-(2-bromoethoxy)-4-chlorobenzene (0.26 g, 1.12 mmol, 1.2 equiv.) was added dropwise. Then reaction was stirred at 80° C. for 16 h. After consumption of the starting material (TLC, 50% EtOAc in hexane), reaction mixture was cooled to room temperature and the solvent was concentrated under reduced pressure and to the residue was added DCM (100 mL), and was washed with water (2×20 mL). Combined organic layer was dried over anhydrous sodium sulfate, filtered and concentrated to give (0.3 g, crude) as pale yellow liquid. LCMS (ES) m/z=369.2 [M+H]+. 1H NMR (400 MHz, DMSO-d6) δ ppm—crude.

Step 2:

To a stirred solution of tert-butyl ((1-(2-(4-chlorophenoxy)ethyl)-5-methylpyrrolidin-3-yl)methyl)carbamate (0.3 g, 0.81 mmol, 1.0 equiv.) in DCM (8.0 mL) was added 4M HCl in dioxane (3.0 mL) dropwise at 0° C. Then reaction mixture was stirred at room temperature for 4 h. After consumption of the starting material (TLC, 5% MeOH in DCM), reaction mixture was concentrated under reduced pressure to give (1-(2-(4-chlorophenoxy)ethyl)-5-methylpyrrolidin-3-yl)methanamine hydrochloride (0.27 g, crude) as sticky solid. LCMS (ES) m/z=269.1 [M+H]+(free amine mass). 1H NMR (400 MHz, DMSO-d6) δ ppm—crude.

Step 3:

To a stirred solution of (1-(2-(4-chlorophenoxy)ethyl)-5-methylpyrrolidin-3-yl)methanamine hydrochloride (0.27 g, 0.88 mmol, 1.0 equiv.) in DCM (20.0 mL) was added triethyl amine (0.37 mL, 2.64 mmol, 3.0 equiv.) and compound 2-(4-chlorophenoxy)acetic acid (0.19 g, 1.06 mmol, 1.2 equiv.) and T3P (50% wt. in ethyl acetate) (1.32 mL, 2.20 mmol, 2.5 equiv.) was added dropwise at 0° C. The reaction was stirred at room temperature for 16 h. The reaction mixture was diluted with DCM (100 mL), and was washed with saturated sodium bicarbonate solution (2×20 mL) and water (2×20 mL). Combined organic layer was dried over anhydrous sodium sulfate, filtered and concentrated to get the crude. Crude was purified by flash column chromatography using 2-3% methanol in dichloromethane 2-(4-chlorophenoxy)-N-((1-(2-(4-chlorophenoxy)ethyl)-5-methylpyrrolidin-3-yl)methyl)acetamide (0.24 g, 62.2% yield) as gummy liquid. LCMS (ES) m/z=437.3 [M+H]+. 1H NMR (400 MHz, DMSO-d6) δ ppm 1.00-0.96 (m, 3H), 1.37-1.29 (m, 0.6H), 1.52-1.58 (m, 0.6H), 1.86-1.91 (m, 0.6H), 1.94-1.99 (m, 0.4H), 2.21-2.25 (m, 2H), 2.30-2.41 (m, 1.3H), 2.86

(d, J=8.0 Hz, 0.5H), 2.99-3.12 (m, 4H), 3.98 (t, J=5.4 Hz, 2H), 4.44 (d, J=6.0 Hz, 2H), 6.89-6.95 (m, 4H), 7.29 (t, J=9.2 Hz, 4H), 8.04-8.14 (m, 1H).

The compounds 42 and 43 were prepared generally according to the procedures described above for Example 41.

TABLE 4

| Cmpd # | Structure | Name | LCMS m/z [M + H]+ | $^1$H-NMR (400 MHz, DMSO-d$_6$) |
|---|---|---|---|---|
| 41 | 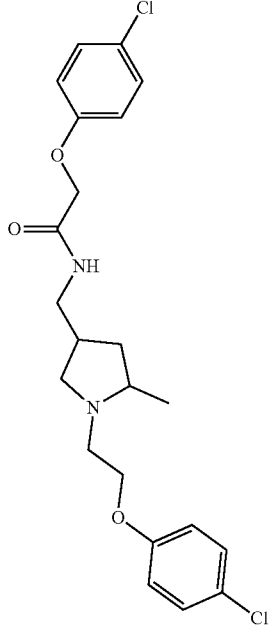 [SMILES: CC1CC(CNC(=O)COc2ccc(Cl)cc2)CN1CCOc1ccc(Cl)cc1] | 2-(4-chlorophenoxy)-N-((1-(2-(4-chlorophenoxy)ethyl)-5-methylpyrrolidin-3-yl)methyl)acetamide | 437.3 | 1.00-0.96 (m, 3H), 1.37-1.29 (m, 0.6H), 1.52-1.58 (m, 0.6 H), 1.86-1.91 (m, 0.6 H), 1.94-1.99 (m, 0.4 H), 2.21-2.25 (m, 2 H), 2.30-2.41 (m, 1.3 H), 2.86 (d, J = 8.0 Hz, 0.5 H), 2.99-3.12 (m, 4 H), 3.98 (t, J = 5.4 Hz, 2 H), 4.44 (d, J = 6.0 Hz, 2 H), 6.89-6.95 (m, 4 H), 7.29 (t, J = 9.2 Hz, 4 H), 8.04-8.14 (m, 1 H). |
| 42 | 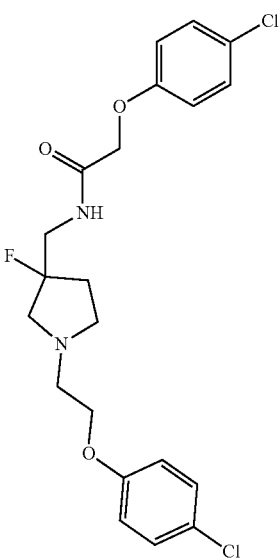 [SMILES: O=C(COc1ccc(Cl)cc1)NCC1(F)CCN(CCOc2ccc(Cl)cc2)C1] | 2-(4-chlorophenoxy)-N-((1-(2-(4-chlorophenoxy)ethyl)-3-fluoropyrrolidin-3-yl)methyl)acetamide | 441.0 | 1.81-2.01 (m, 2 H), 2.48-2.78 (m, 6 H), 3.42-3.49 (m, 2 H), 4.01 (t, J = 5.2 Hz, 2 H), 4.53 (s, 2 H), 6.94 (dd, J = 3.2, 8.8 Hz, 4 H), 7.30 (t, J = 8.8 Hz, 4 H), 8.27 (bs, 1 H). |

TABLE 4-continued
| Cmpd # | Structure | Name | LCMS m/z [M + H]+ | 1H-NMR (400 MHz, DMSO-d6) |
|---|---|---|---|---|
| 43 | 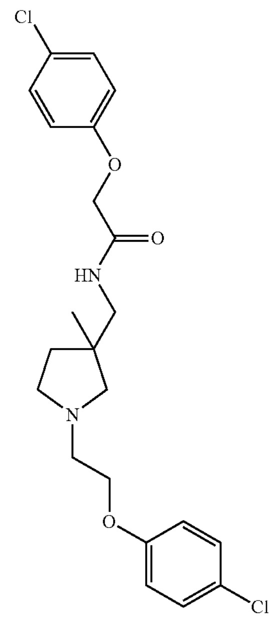 [SMILES: CC1(CNC(=O)COc2ccc(Cl)cc2)CCN(CCOc2ccc(Cl)cc2)C1] | 2-(4-chlorophenoxy)-N-((1-(2-(4-chlorophenoxy)ethyl)-3-methylpyrrolidin-3-yl)methyl)acetamide | 437.0 | 0.95 (s, 3 H), 1.33 (s, 1 H), 1.59 (s, 1 H), 2.10-2.12 (m, 1 H), 2.48-2.65 (m, 5 H), 3.06-3.07 (m, 2 H), 3.98 (s, 2 H), 4.49 (s, 2 H), 6.90-6.94 (m, 4 H), 7.27-7.30 (m, 4 H), 8.08 (s, 1 H). |
Example 44
N-((1-(3-(4-chlorophenoxy)propyl)pyrrolidin-3-yl)methyl)-2-(3,4-dichlorophenoxy)acetamide
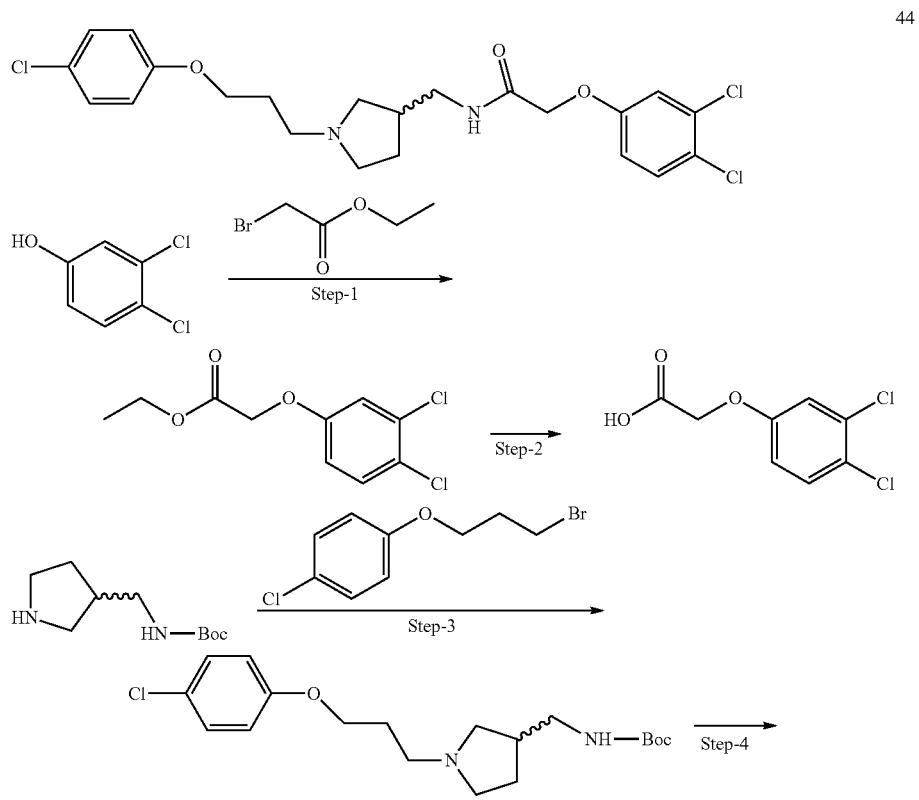

-continued

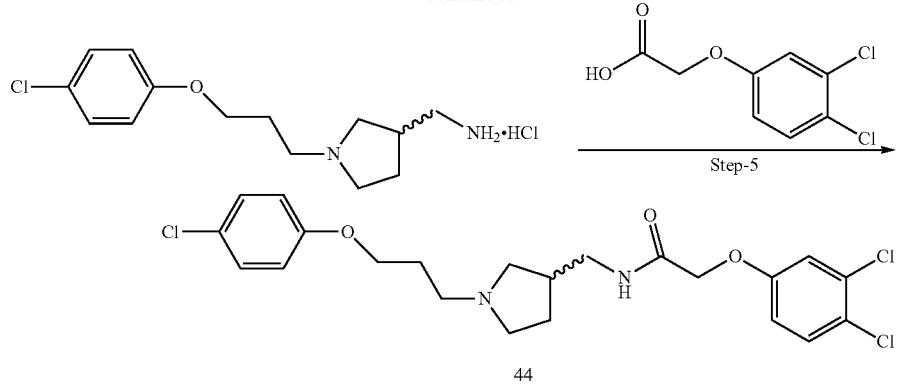

44

Step 1:

To a solution of 3,4-dichlorophenol (1.0 g, 6.13 mmol, 1 equiv), DMF (15 mL) at room temperature was added anhydrous potassium carbonate (1.26 g, 9.2 mmol, 1.5 equiv) portion wise. After stirring for 2 minutes, ethyl bromo acetate (0.81 mL, 7.35 mmol, 1.2 equiv) was added. The reaction mixture was heated at 80° C. for 4 h. After consumption of the starting material (TLC, 5% EtOAc in hexane), the reaction mixture was cooled to room temperature, diluted with water (100 mL) and extracted with EtOAc (2×100 mL). The combined organic layer was washed with brine solution (50 mL), dried over anhydrous sodium sulphate, filtered and concentrated en vacuum to give the crude product. The crude product was purified by flash column chromatography (Combiflash) using a silica gel column and the product was eluted at 15% ethyl acetate in hexane. Fractions containing product were concentrated to give ethyl 2-(3,4-dichlorophenoxy)acetate. (1.5 g, 65% yield) as pale yellow liquid. LCMS (ES) m/z=248.0 [M+H]$^+$. $^1$H NMR (400 MHz, CDCl$_3$): δ ppm 1.28-1.31 (m, 3H), 4.24-4.29 (m, 2H), 4.58 (s, 2H), 6.75-6.78 (m, 1H), 7.01 (m, 1H), 7.33 (d, J=8.0 Hz, 1H).

Step 2:

To a solution of ethyl 2-(3, 4-dichlorophenoxy) acetate (1.5 g 6.04 mmol, 1 equiv) in THF (15 mL), water (5 mL) at 0° C. was added LiOH.H2O (0.62 g, 15.1 mmol 2.5 equiv) and the reaction mixture was stirred at room temperature for 1 h. After consumption of the starting material (TLC, 5% Methanol in DCM), THF was removed under vacuum and the reaction mixture was diluted with water (10 mL) followed by extraction with Et$_2$O (20 mL). The aqueous layer was acidified with 1 N HCl upto pH 3 and the precipitated product was filtered through a cintered funnel, washed with ice-cold water (10 mL) and dried under high vacuum to give 2-(3,4-dichlorophenoxy)acetic acid (1 g, 75% yield) as white solid. LCMS (ES) m/z=220.0 [M+H]$^+$. $^1$H NMR (400 MHz, DMSO-d$_6$) δ ppm 4.72 (s, 2H), 6.92-6.95 (m, 1H), 7.21 (d, J=8.8 Hz, 1H), 7.51 (d, J=9.6 Hz, 1H), 13.05 (bs, 1H).

Step 1:

To a stirred solution of tert-butyl (pyrrolidin-3-ylmethyl) carbamate (3.0 g, 14.9 mmol 1 equiv) in DMF (25 mL) at room temperature ware added anhydrous potassium carbonate (4.41 g, 29.8 mmol, 2 equiv), Potassium iodide (0.24 g, 1.49 mmol, 0.1 equiv) and 1-(3-bromopropoxy)-4-chlorobenzene (5.54 g, 22.3 mmol, 1.5 equiv) The reaction mixture was heated at 80° C. for 3 h. After consumption of the starting material (TLC, 50 EtOAc in hexane), the reaction mixture was cooled to room temperature, diluted with water (100 mL) and extracted with EtOAc (2×100 mL). The combined organic layer was washed with brine solution (50 mL), dried over anhydrous sodium sulphate, filtered and concentrated en vacuum to give the product. (1.5 g, 65% yield) as pale yellow liquid. LCMS (ES) m/z=369.0 [M+H]$^+$. $^1$H NMR (400 MHz, DMSO-d$_6$): δ 1.35 (m, 9H), 1.84-1.87 (m, 3H), 2.22 (bs, 1H), 2.30-2.35 (m, 1H) 2.48-2.60 (m, 3H), 2.86-2.89 (m, 2H), 3.96-3.99 (m, 2H), 6.85 (bs, 1H), 6.92 (d, J=8.8 Hz, 2H), 7.28 (d, J=8.4 Hz, 2H).

Step 2:

To a solution tert-butyl ((1-(3-(4-chlorophenoxy)propyl) pyrrolidin-3-yl)methyl)carbamate (2.5 g, 6.77 mmol, 1 equiv) 1-4 dioxane (15 mL) was added fallowed by 4.0 M Dioxane.HCl (10 mL) was added and stirred at for room temperature 12 h. After consumption of the starting material (TLC, 5% Methanol in DCM), 1,4-dioxane was evaporated under reduced pressure. The solid obtained was triturated with n-pentane (50 mL) dried under high vacuum to give (1-(3-(4-chlorophenoxy)propyl)pyrrolidin-3-yl)methanamine hydrochloride. (2.01 g, 97% yield) as off white solid. LCMS (ES) m/z=269.1 [M+H]$^+$.

Step 3:

To (1-(3-(4-chlorophenoxy)propyl)pyrrolidin-3-yl)methanamine hydrochloride (0.20 g, 0.65 mmol, 1 equiv) taken in DCM (10 mL) at 0° C. was added triethylamine (0.36 mL, 2.68 mmol, 4 equiv) and 2-(3,4-dichlorophenoxy)acetic acid (0.17 g, 0.78 mmol, 1.2 equiv). After stirring for 5 minutes at 0° C., T3P (50 wt. % in ethyl acetate) (0.58 mL, 0.97 mmol, 1.5 equiv) was added and the reaction mixture was stirred at room temperature for 16 h. After consumption of the starting material (TLC, 5% Methanol in DCM), the reaction mixture was diluted with water (5 mL) and extracted with DCM (2×10 mL). The combined organic extract was washed with saturated aqueous NaHCO$_3$ solution (8 mL) and water (10 mL). The organic phase was dried over anhydrous sodium sulphate, filtered and concentrated under reduced pressure to give the crude product. The crude material was purified by flash column chromatography using a silica gel column where the product was eluted at 4-5% methanol in DCM. Fractions containing product were concentrated under reduced pressure to give N-((1-(3-(4-chlorophenoxy)propyl)pyrrolidin-3-yl)methyl)-2-(3,4-dichlorophenoxy)acetamide (0.057 g, 18% yield) as brownish sticky solid. LCMS (ES) m/z=473.1 [M+H]$^+$. $^1$H NMR (400 MHz, DMSO-d$_6$) δ ppm 1.34 (bs, 1H), 1.79-1.83 (m, 3H), 2.22-2.30 (m, 2H), 2.48 (m, 5H), 3.05-3.08 (m, 2H), 3.95-3.98

(m, 2H), 4.51 (s, 2H), 6.90-6.93 (m, 1H), 6.94-6.96 (m, 1H), 7.20-7.21 (m, 1H), 7.27 (d, J=12.0 Hz, 2H), 7.51 (d, J=12.0 Hz, 1H), 8.13 (bs, 1H).

The Compounds of Examples 45 to 74 were prepared generally according to the procedures described above for Example 44.

TABLE 5

| Cmpd # | Structure | Name | LCMS m/z [M + H]+ | 1H-NMR (400 MHz, DMSO-d6) |
|---|---|---|---|---|
| 44 | 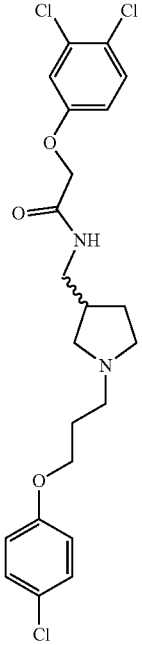 | N-((1-(3-(4-chlorophenoxy)propyl)pyrrolidin-3-yl)methyl)-2-(3,4-dichlorophenoxy)acetamide | 473.1 | 1.34 (bs, 1 H), 1.79-1.83 (m, 3 H), 2.22-2.30 (m, 2 H), 2.48 (m, 5 H), 3.05-3.08 (m, 2 H), 3.95-3.98 (m, 2 H), 4.51 (s, 2 H), 6.90-6.93 (m, 1 H), 6.94-6.96 (m, 1 H), 7.20-7.21 (m, 1 H), 7.27 (d, J = 12.0 Hz, 2 H), 7.51 (d, J = 12.0 Hz, 1 H), 8.13 (bs, 1 H). |
| 45 | 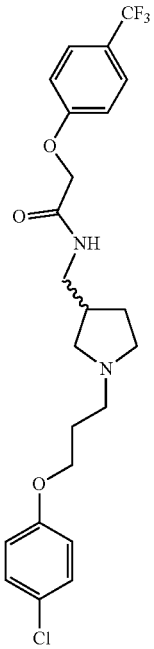 [SMILES: O=C(COc1ccc(C(F)(F)F)cc1)NCC1CCN(CCCOc2ccc(Cl)cc2)C1] | N-((1-(3-(4-chlorophenoxy)propyl)pyrrolidin-3-yl)methyl)-2-(4-(trifluoromethyl)phenoxy)acetamide | 471.1 | 1.34 (m, 1 H), 1.79-1.82 (m, 3 H), 2.22-2.30 (m, 2 H), 2.48 (m, 5 H), 3.06-3.07 (m, 2 H), 3.95-3.98 (m, 2 H), 4.56 (s, 2 H), 6.91 (d, J = 8.0 Hz, 2 H), 7.09 (d, J = 8.0 Hz, 2 H), 7.27 (d, J = 12.0 Hz, 2 H), 7.64 (d, J = 8.0 Hz, 2 H), 8.16 (bs, 1 H). |

TABLE 5-continued

| Cmpd # | Structure | Name | LCMS m/z [M + H]+ | 1H-NMR (400 MHz, DMSO-d6) |
|---|---|---|---|---|
| 46 | 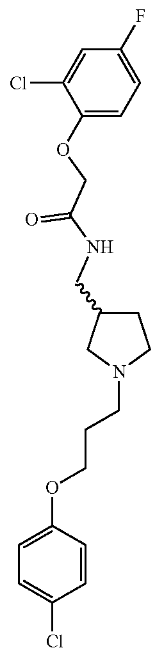 [SMILES: O=C(COc1ccc(F)cc1Cl)NCC1CCN(CCCOc2ccc(Cl)cc2)C1] | 2-(2-chloro-4-fluorophenoxy)-N-((1-(3-(4-chlorophenoxy)propyl)pyrrolidin-3-yl)methyl)acetamide | 455.1 | 1.32-1.34 (m, 1 H), 1.79-1.82 (m, 3 H), 2.30 (bs, 2 H), 2.48 (bs, 5 H), 3.05-3.08 (m, 2 H), 3.94-3.98 (m, 2 H), 4.55 (s, 2 H), 6.94 (d, J = 8.0 Hz, 2 H), 7.04 (d, J = 8.0 Hz, 1 H), 7.17 (d, J = 8.0 Hz, 1 H), 7.27 (d, J = 8.0 Hz, 2 H), 7.41 (d, J = 8.0 Hz, 1 H), 8.09 (bs, 1 H). |
| 47 | 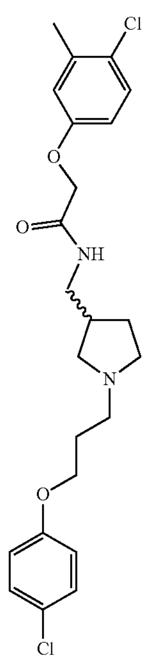 [SMILES: Cc1cc(OCC(=O)NCC2CCN(CCCOc3ccc(Cl)cc3)C2)ccc1Cl] | 2-(4-chloro-3-methylphenoxy)-N-((1-(3-(4-chlorophenoxy)propyl)pyrrolidin-3-yl)methyl)acetamide | 452.1 | 1.31-1.35 (m, 1 H), 1.74-1.84 (m, 3 H), 2.30 (bs, 5 H), 2.48 (bs, 5 H), 3.05-3.08 (m, 2 H), 3.95-3.98 (m, 2 H), 4.43 (s, 2 H), 6.76-6.79 (m, 1 H), 6.90-6.93 (m, 3 H), 7.27 (d, J = 12.0 Hz, 3 H), 8.09 (bs, 1 H). |

TABLE 5-continued

| Cmpd # | Structure | Name | LCMS m/z [M + H]+ | 1H-NMR (400 MHz, DMSO-d6) |
|---|---|---|---|---|
| 48 | 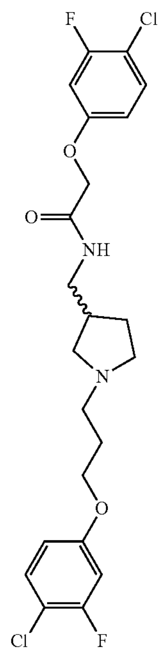 [SMILES: O=C(COc1ccc(Cl)c(F)c1)NCC1CCN(CCCOc2ccc(Cl)c(F)c2)C1] | 2-(4-chloro-3-fluorophenoxy)-N-((1-(3-(4-chloro-3-fluorophenoxy)propyl)pyrrolidin-3-yl)methyl)acetamide | 473.0 | 1.35 (bs, 1 H), 1.80-1.81 (m, 3 H), 2.23 (bs, 2 H), 2.48 (bs, 5 H), 3.07 (bs, 2 H), 3.98-4.01 (m, 2 H), 4.50 (s, 2 H), 6.78-6.82 (m, 2 H), 6.99-7.03 (m, 2 H), 7.39-7.48 (m, 2 H), 8.13 (bs, 1 H). |
| 49 | 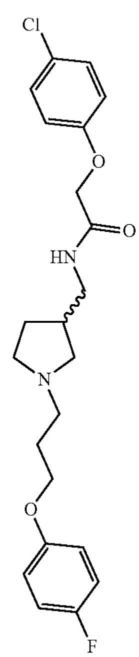 [SMILES: O=C(COc1ccc(Cl)cc1)NCC1CCN(CCCOc2ccc(F)cc2)C1] | 2-(4-chlorophenoxy)-N-((1-(3-(4-fluorophenoxy)propyl)pyrrolidin-3-yl)methyl)acetamide | 421.1 | 1.35 (bs, 1 H), 1.80-1.81 (m, 3 H), 2.25-2.30 (m, 2 H), 2.48 (bs, 5 H), 3.07 (bs, 2 H), 3.93-3.96 (m, 2 H), 4.45 (s, 2 H), 6.88-6.95 (m, 4 H), 7.05-7.09 (m, 2 H), 7.31 (d, J = 8.3 Hz, 2 H), 8.11 (bs, 1 H). |

TABLE 5-continued

| Cmpd # | Structure | Name | LCMS m/z [M + H]+ | 1H-NMR (400 MHz, DMSO-d6) |
|---|---|---|---|---|
| 50 | 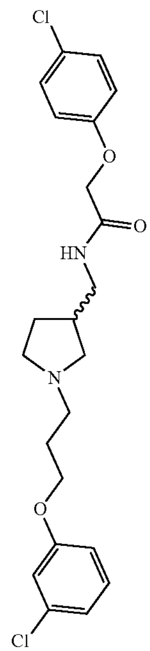 [SMILES: O=C(COc1ccc(Cl)cc1)NCC1CCN(CCCOc2cccc(Cl)c2)C1] | 2-(4-chlorophenoxy)-N-((1-(3-(3-chlorophenoxy)propyl)pyrrolidin-3-yl)methyl)acetamide | 439.1 | 1.32-1.34 (m, 1 H), 1.80-1.89 (m, 3 H), 2.24-2.30 (m, 2 H), 2.48 (bs, 5 H), 3.07 (bs, 2 H), 3.98-4.01 (m, 2 H), 4.45 (s, 2 H), 6.86-6.89 (m, 1 H), 6.95-6.97 (m, 4 H), 7.24-7.28 (m, 2 H), 7.30-7.32 (m, 2 H), 8.11 (bs, 1 H). |
| 51 | 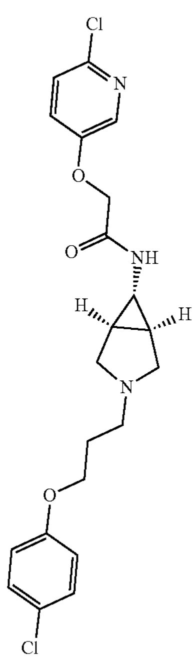 [SMILES: O=C(COc1ccc(Cl)nc1)N[C@H]1[C@@H]2CN(CCCOc3ccc(Cl)cc3)C[C@@H]21] | N-((1R,5S,6s)-3-(3-(4-chlorophenoxy)propyl)-3-azabicyclo[3.1.0]hexan-6-yl)-2-((6-chloropyridin-3-yl)oxy)acetamide | 436.1 | 1.50 (s, 2 H), 1.78 (t, J = 6.6 Hz, 2 H), 2.26 (d, J = 7.6 Hz, 2 H), 2.38-2.48 (m, 2 H), 2.83 (s, 1 H), 3.00 (d, J = 8.8 Hz, 2 H), 3.93 (t, J = 6.2 Hz, 2 H), 4.51 (s, 2 H), 6.91 (d, J = 8.8 Hz, 2 H), 7.28 (d, J = 8.8 Hz, 2 H), 7.42 (s, 2 H), 8.09 (s, 2 H). |

TABLE 5-continued

| Cmpd # | Structure | Name | LCMS m/z [M + H]+ | 1H-NMR (400 MHz, DMSO-d6) |
|---|---|---|---|---|
| 52 | 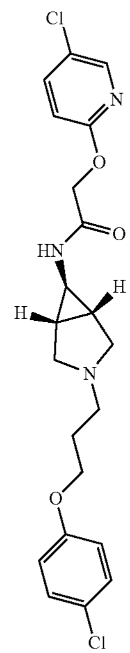 | N-((1R,5S,6s)-3-(3-(4-chlorophenoxy)propyl)-3-azabicyclo[3.1.0]hexan-6-yl)-2-((5-chloropyridin-2-yl)oxy)acetamide | 436.1 | 1.46-1.59 (m, 2 H), 1.76-1.81 (m, 2 H), 2.23-2.30 (m, 2 H), 2.43-2.48 (m, 2 H), 2.79-2.90 (m, 1 H), 2.97-2.99 (m, 2 H), 3.91-3.94 (m, 2 H), 4.61 (s, 2 H), 6.90-6.93 (m, 3 H), 7.28 (d, J = 8.8 Hz, 2 H), 7.79-7.82 (m, 1 H), 7.96-7.97 (m, 1 H), 8.14-8.15 (m, 1 H). |
| 53 | 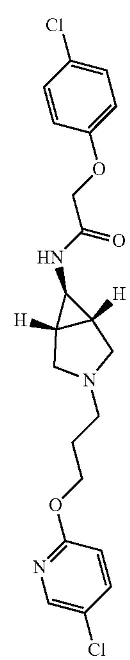 | 2-(4-chlorophenoxy)-N-((1R,5S,6s)-3-(3-((5-chloropyridin-2-yl)oxy)propyl)-3-azabicyclo[3.1.0]hexan-6-yl)acetamide | 436.0 | 1.51-1.52 (m, 2 H), 1.77-1.80 (m, 2 H), 2.23-2.30 (m, 2 H), 2.43-2.48 (m, 2 H), 2.82-2.86 (m, 1 H), 2.98-3.01 (m, 2 H), 4.19-4.22 (m, 2 H), 4.39 (s, 2 H), 6.83 (d, J = 8.8, 1 H), 6.94 (d, J = 8.8 Hz, 2 H), 7.32 (d, J = 8.8 Hz, 2 H), 7.73-7.76 (m, 1 H), 8.02-8.03 (m, 1 H), 8.16-8.17 (m, 1 H). |

TABLE 5-continued

| Cmpd # | Structure | Name | LCMS m/z [M + H]⁺ | ¹H-NMR (400 MHz, DMSO-d₆) |
|---|---|---|---|---|
| 54 | 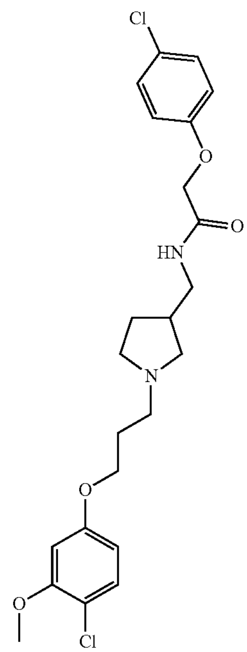 [SMILES: COc1cc(OCCCN2CCC(CNC(=O)COc3ccc(Cl)cc3)C2)ccc1Cl] | N-((1-(3-(4-chloro-3-methoxyphenoxy)propyl)pyrrolidin-3-yl)methyl)-2-(4-chlorophenoxy)acetamide | 467.1 | 1.37-1.48 (m, 1 H), 1.49-1.69 (m, 3 H), 1.70-1.84 (m, 3 H), 2.18-2.30 (m, 2 H), 2.47-2.48 (m, 4 H), 2.60-2.65 (m, 1 H), 3.08-3.23 (m, 2 H), 3.80 (s, 3 H), 3.99 (t, J = 6 Hz, 2 H), 4.45 (s, 2 H), 6.48-6.51 (m, 1 H), 6.55-6.64 (m, 1 H), 6.95 (d, J = 8.8 Hz, 2 H), 7.26 (d, J = 8.8 Hz, 1 H), 7.33 (d, J = 8.8 Hz, 2 H), 8.12 (bs, 1 H). |
| 55 | 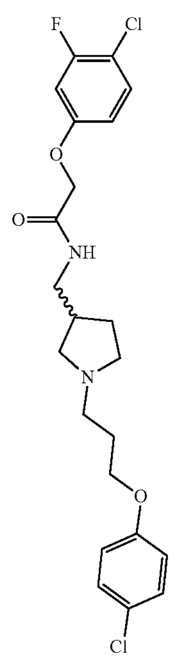 [SMILES: O=C(COc1ccc(Cl)c(F)c1)NCC1CCN(CCCOc2ccc(Cl)cc2)C1] | 2-(4-chloro-3-fluorophenoxy)-N-((1-(3-(4-chlorophenoxy)propyl)pyrrolidin-3-yl)methyl)acetamide | 455.1 | 1.32-1.35 (m, 1 H), 1.79-1.82 (m, 3 H), 2.23-2.20 (m, 2 H), 2.34-2.46 (m, 5 H), 3.07 (t, J = 6.0 Hz, 2 H), 3.96 (t, J = 6.2 Hz, 2 H), 4.50 (s, 2 H), 6.82 (d, J = 8.8 Hz, 1 H), 6.91 (d, J = 8.8 Hz, 2 H), 7.02 (dd, J = 11.6, 2.8 Hz, 1 H), 7.27 (d, J = 8.8 Hz, 2 H), 7.46 (t, J = 8.8 Hz, 1 H), 8.12 (bs, 1 H). |

TABLE 5-continued
| Cmpd # | Structure | Name | LCMS m/z [M + H]+ | 1H-NMR (400 MHz, DMSO-d6) |
|---|---|---|---|---|
| 56 | 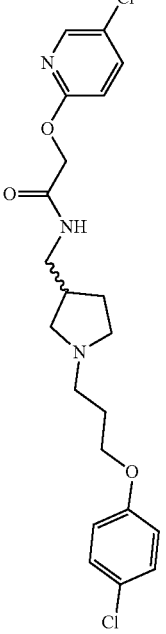 | N-((1-(3-(4-chlorophenoxy)propyl)pyrrolidin-3-yl)methyl)-2-((5-chloropyridin-2-yl)oxy)acetamide | 438.1 | 1.31 (bs, 1 H), 1.81-1.88 (m, 3 H), 2.21-2.30 (m, 2 H), 2.40-2.47 (m, 5 H), 3.04 (bs, 2 H), 3.97 (t, J = 12.4 Hz, 2 H), 4.66 (s, 2 H), 6.91-6.94 (m, 3 H), 7.28 (d, J = 8.8 Hz, 2 H), 7.81 (dd, J = 8.8, 2.8 Hz, 1 H), 8.01 (bs, 1 H), 8.14 (d, J = 2.0 Hz, 1 H). |
| 57 | 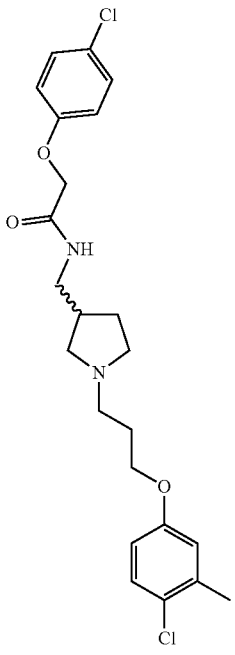 [SMILES: Cc1cc(OCCCN2CCC(CNC(=O)COc3ccc(Cl)cc3)C2)ccc1Cl] | N-((1-(3-(4-chloro-3-methylphenoxy)propyl)pyrrolidin-3-yl)methyl)-2-(4-chlorophenoxy)acetamide | 451.1 | 1.31-1.34 (m, 1 H), 1.80-1.82 (m, 3 H), 2.22-2.25 (m, 5 H), 2.30-2.36 (m, 5 H), 3.07 (t, J = 6.4 Hz, 2 H), 3.95 (t, J = 6.0 Hz, 2 H), 4.45 (s, 2 H), 6.75 (dd, J = 8.8, 2.8 Hz, 1 H), 6.90-6.94 (m, 3 H), 7.24 (d, J = 8.4 Hz, 1 H), 7.31 (d, J = 8.8 Hz, 2 H), 8.10 (bs, 1 H). |

| Cmpd # | Structure | Name | LCMS m/z [M + H]+ | 1H-NMR (400 MHz, DMSO-d6) |
|---|---|---|---|---|
| 58 | 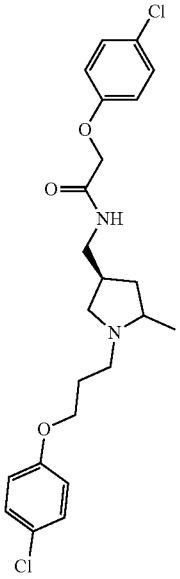<br>Isomer pair 2 | 2-(4-chlorophenoxy)-N-(((3R)-1-(3-(4-chlorophenoxy)propyl)-5-methylpyrrolidin-3-yl)methyl)acetamide | 451.2 | 0.95 (s, 3 H), 1.79 (bs, 2 H), 1.91-2.10 (m, 3 H), 2.19 (bs, 3 H), 2.80-2.90 (m, 2 H), 3.04-3.08 (m, 2 H), 3.94-4.00 (m, 2 H), 4.44 (s, 2 H), 6.89-6.95 (m, 4 H), 7.26-7.32 (m, 4 H), 8.12 (bs, 1 H). |
| 59 | 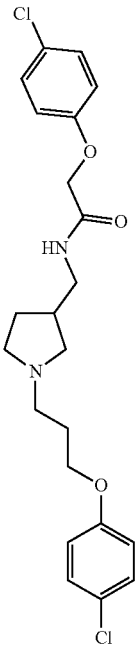 [SMILES: O=C(COc1ccc(Cl)cc1)NCC1CCN(CCCOc2ccc(Cl)cc2)C1] | 2-(4-chlorophenoxy)-N-((1-(3-(4-chlorophenoxy)propyl)pyrrolidin-3-yl)methyl)acetamide | 437.3 | 1.33-1.34 (m, 1 H), 1.78-1.83 (m, 3 H), 2.21-2.41 (m, 7 H), 3.06-3.07 (m, 2 H), 3.97 (t, J = 6.0 Hz, 2 H), 4.45 (s, 2 H), 6.93 (t, J = 9.6 Hz, 4 H), 7.27-7.33 (m, 4 H), 8.10 (bs, 1 H). |

TABLE 5-continued
| Cmpd # | Structure | Name | LCMS m/z [M + H]+ | 1H-NMR (400 MHz, DMSO-d6) |
|---|---|---|---|---|
| 60 | 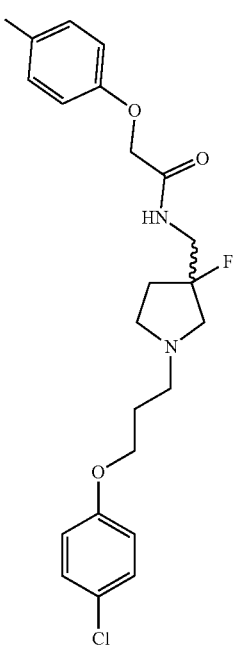 | 2-(4-chlorophenoxy)-N-((1-(3-(4-chlorophenoxy)propyl)-3-fluoropyrrolidin-3-yl)methyl)acetamide | 455.1 | 1.78-2.00 (m, 5 H), 2.30-2.37 (m, 1 H), 2.48-2.69 (m, 4 H), 3.42 (d, J = 6.4 Hz, 1 H), 3.47 (d, J = 5.2 Hz, 1 H), 3.97 (t, J = 6.4 Hz, 2 H), 4.53 (s, 2 H), 6.93 (t, J = 9.6 Hz, 4 H), 7.30 (dd, J = 9.2 Hz, J = 13.2 Hz, 4 H), 8.25 (bs, 1 H). |
| 61 | 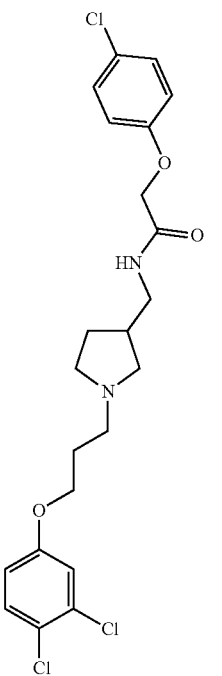 [SMILES: O=C(COc1ccc(Cl)cc1)NCC1CCN(CCCOc2ccc(Cl)c(Cl)c2)C1] | 2-(4-chlorophenoxy)-N-((1-(3-(3,4-dichlorophenoxy)propyl)pyrrolidin-3-yl)methyl)acetamide | 471.0 | 1.32-1.35 (m, 1 H), 1.80-1.83 (m, 3 H), 2.24 (s, 2 H), 2.45 (bs, 5 H), 3.07 (bs, 2 H), 4.01 (t, J = 5.6 Hz, 2 H), 4.45 (s, 2 H), 6.92-6.95 (m, 3 H), 7.19 (s, 1 H), 7.31 (d, J = 8.8 Hz, 2 H), 7.48 (d, J = 8.8 Hz, 1H), 8.11 (bs, 1 H). |

TABLE 5-continued
| Cmpd # | Structure | Name | LCMS m/z [M + H]+ | 1H-NMR (400 MHz, DMSO-d6) |
|---|---|---|---|---|
| 62 | 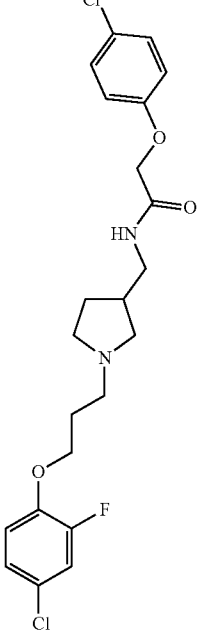 | N-((1-(3-(4-chloro-2-fluorophenoxy)propyl)pyrrolidin-3-yl)methyl)-2-(4-chlorophenoxy)acetamide | 455.0 | 1.32-1.34 (m, 1 H), 1.78-1.85 (m, 3 H), 2.24 (bs, 2 H), 2.48 (bs, 5 H), 3.07 (t, J = 5.6 Hz, 2 H), 4.06 (t, J = 5.6 Hz, 2 H), 4.45 (s, 2 H), 6.94 (d, J = 8.8 Hz, 2 H), 7.17 (s, 2 H), 7.31 (d, J = 8.8 Hz, 2 H), 7.38 (d, J = 11.6 Hz, 1 H), 8.10 (bs, 1 H). |
| 63 | 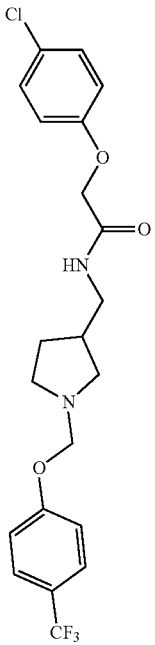 | 2-(4-chlorophenoxy)-N-((1-(3-(4-(trifluoromethyl)phenoxy)propyl)pyrrolidin-3-yl)methyl)acetamide | 471.0 | 1.32-1.36 (m, 1 H), 1.79 (bs, 1 H), 1.86 (bs, 2 H), 2.26 (bs, 2 H), 2.48 (bs, 5 H), 3.08 (bs, 2 H), 4.07 (t, J = 6.4 Hz, 2 H), 4.46 (s, 2 H), 6.95 (d, J = 8.8 Hz, 2H), 7.08 (d, J = 8.4 Hz, 2 H), 7.32 (d, J = 8.8 Hz, 2 H), 7.61 (d, J = 8.4 Hz, 2 H), 8.12 (bs, 1 H). |

TABLE 5-continued

| Cmpd # | Structure | Name | LCMS m/z [M + H]+ | 1H-NMR (400 MHz, DMSO-d6) |
|---|---|---|---|---|
| 64 | 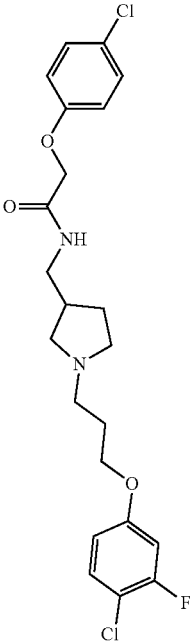 [SMILES: O=C(COc1ccc(Cl)cc1)NCC1CCN(CCCOc2ccc(Cl)c(F)c2)C1] | N-((1-(3-(4-chloro-3-fluorophenoxy)propyl)pyrrolidin-3-yl)methyl)-2-(4-chlorophenoxy)acetamidee | 455.1 | 1.32-1.35 (m, 1 H), 1.78-1.83 (m, 3 H), 2.23 (bs, 2 H), 2.48 (bs, 5 H), 3.07 (t, J = 6.4 Hz, 2 H), 4.00 (t, J = 6.4 Hz, 2 H), 4.45 (s, 2 H), 6.79 (dd, J = 2.4, 8.8 Hz, 1 H), 6.94 (d, J = 8.8 Hz, 2 H), 7.02 (dd, J = 2.4, 11.6 Hz, 1 H), 7.31 (d, J = 8.8 Hz, 2 H), 7.42 (t, J = 8.8 Hz, 1 H), 8.11 (bs, 1 H). |
| 65 | 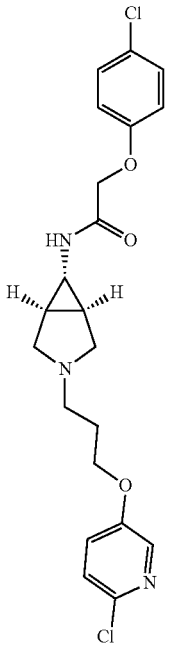 [SMILES: O=C(COc1ccc(Cl)cc1)N[C@H]1[C@@H]2CN(CCCOc3ccc(Cl)nc3)C[C@@H]21] | 2-(4-chlorophenoxy)-N-((1R,5S,6s)-3-(3-((6-chloropyridin-3-yl)oxy)propyl)-3-azabicyclo[3.1.0]hexan-6-yl)acetamide | 436.1 | 1.51 (s, 2 H), 1.79-1.82 (m, 2 H), 2.26 (d, J = 7.6 Hz, 2 H), 2.48 (bs, 2 H), 2.83 (bs, 1 H), 3.00 (d, J = 8.4 Hz, 2 H), 4.03 (t, J = 6.4 Hz, 2 H), 4.40 (s, 2 H), 6.93 (d, J = 8.4 Hz, 2 H), 7.31 (d, J = 8.8 Hz, 2 H), 7.37-7.46 (m, 2 H), 8.03 (d, J = 3.6 Hz, 1 H), 8.07 (d, J = 2.0 Hz, 1 H). |

TABLE 5-continued

| Cmpd # | Structure | Name | LCMS m/z [M + H]+ | 1H-NMR (400 MHz, DMSO-d6) |
|---|---|---|---|---|
| 66 | 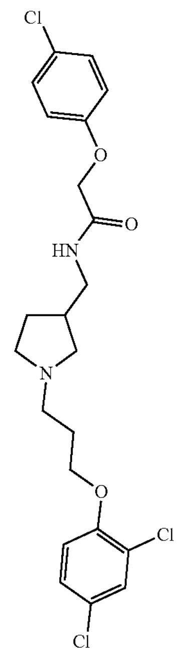 [SMILES: O=C(COc1ccc(Cl)cc1)NCC1CCN(CCCOc2ccc(Cl)cc2Cl)C1] | 2-(4-chlorophenoxy)-N-((1-(3-(2,4-dichlorophenoxy)propyl)pyrrolidin-3-yl)methyl)acetamide | 471.0 | 1.32-1.35 (m, 1 H), 1.77-1.88 (m, 3 H), 2.26 (bs, 2 H), 2.30 (bs, 3 H), 2.48 (bs, 2 H), 3.07 (t, J = 6.0 Hz, 2 H), 4.08 (t, J = 6.0 Hz, 2 H), 4.45 (s, 2 H), 6.94 (d, J = 9.2 Hz, 2 H), 7.13 (d, J = 8.0 Hz, 1 H), 7.30-7.34 (m, 3 H), 7.52 (t, J = 2.4 Hz, 1 H), 8.11 (bs, 1 H). |
| 67 | 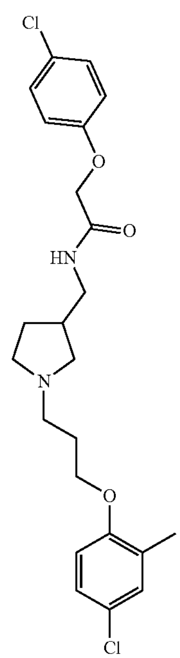 [SMILES: Cc1cc(Cl)ccc1OCCCN1CCC(CNC(=O)COc2ccc(Cl)cc2)C1] | N-((1-(3-(4-chloro-2-methylphenoxy)propyl)pyrrolidin-3-yl)methyl)-2-(4-chlorophenoxy)acetamide | 451.1 | 1.37 (bs, 1 H), 1.85 (bs, 3 H), 2.12 (s, 3 H), 2.28-2.31 (m, 2 H), 2.40-2.65 (m, 5 H), 3.08 (bs, 2 H), 3.98 (t, J = 6.0 Hz, 2 H), 4.46 (s, 2 H), 6.89 (d, J = 8.4 Hz, 1 H), 6.94 (d, J = 8.8 Hz, 2 H), 7.13-7.17 (m, 2 H), 7.32 (d, J = 8.8 Hz, 2 H), 8.13 (bs, 1 H). |

TABLE 5-continued

| Cmpd # | Structure | Name | LCMS m/z [M + H]+ | 1H-NMR (400 MHz, DMSO-d6) |
|---|---|---|---|---|
| 68 | 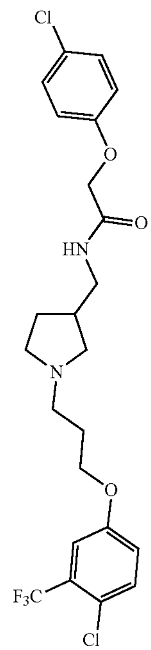 [SMILES: O=C(COc1ccc(Cl)cc1)NCC1CCN(CCCOc2ccc(Cl)c(C(F)(F)F)c2)C1] | N-((1-(3-(4-chloro-3-(trifluoromethyl)phenoxy)propyl)pyrrolidin-3-yl)methyl)-2-(4-chlorophenoxy)acetamide | 505.1 | 1.37 (bs, 1 H), 1.84 (bs, 3 H), 2.26 (bs, 2 H), 2.48 (bs, 5 H), 3.08 (bs, 2 H), 4.08 (t, J = 6.0 Hz, 2 H), 4.45 (s, 2 H), 6.94 (d, J = 8.8 Hz, 2 H), 7.24 (d, J = 8.8 Hz, 1 H), 7.30-7.32 (m, 3 H), 7.58 (d, J = 8.4 Hz, 1 H), 8.11 (bs, 1 H). |
| 69 | 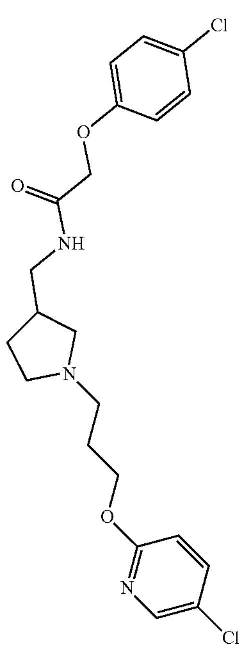 [SMILES: O=C(COc1ccc(Cl)cc1)NCC1CCN(CCCOc2ccc(Cl)cn2)C1] | 2-(4-chlorophenoxy)-N-((1-(3-((5-chloropyridin-2-yl)oxy)propyl)pyrrolidin-3-yl)methyl)acetamide | 438.1 | 1.40 (bs, 1 H), 1.86 (bs, 3 H), 2.31 (bs, 2 H), 2.40 (bs, 3 H), 2.60 (bs, 2 H), 3.10 (bs, 2 H), 4.25 (t, J = 6.0 Hz, 2 H), 4.46 (s, 2 H), 6.83 (d, J = 8.8 Hz, 1 H), 6.95 (d, J = 8.8 Hz, 2 H), 7.32 (d, J = 8.8 Hz, 2 H), 7.77 (dd, J = 2.0, 8.8 Hz, 1 H), 8.16 (bs, 2 H). |

TABLE 5-continued

| Cmpd # | Structure | Name | LCMS m/z [M + H]+ | 1H-NMR (400 MHz, DMSO-d6) |
|---|---|---|---|---|
| 70 | 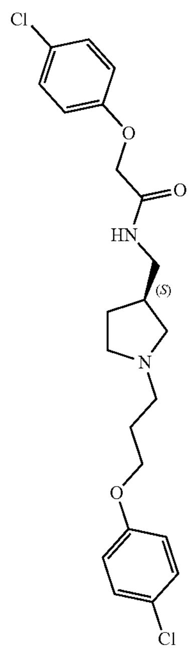 | (S)-2-(4-chlorophenoxy)-N-((1-(3-(4-chlorophenoxy)propyl)pyrrolidin-3-yl)methyl)acetamide | 437.1 | 1.31-1.36 (m, 1 H), 1.74-1.84 (m, 3 H), 2.20-2.25 (m, 2 H), 2.31-2.48 (m, 5 H), 3.07 (t, J = 6.0 Hz, 2 H), 3.97 (d, J = 6.0 Hz, 2 H), 4.45 (s, 2 H), 6.93 (t, J = 10.0 Hz, 4 H), 7.30 (dd, J = 8.8, 14.4 Hz, 4 H), 8.10 (t, J = 5.6 Hz, 1 H). |
| 71 | 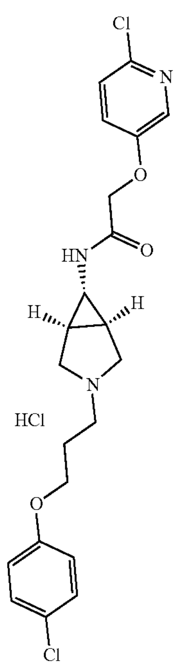 [SMILES: O=C(COc1ccc(Cl)nc1)N[C@H]1[C@@H]2CN(CCCOc3ccc(Cl)cc3)C[C@@H]21 ; Cl] | N-((1R,5S,6s)-3-(3-(4-chlorophenoxy)propyl)-3-azabicyclo[3.1.0]hexan-6-yl)-2-((6-chloropyridin-3-yl)oxy)acetamide hydrochloride | 436.1 | 1.94-2.08 (m, 4 H), 2.81-2.86 (m, 0.5 H), 3.11-3.36 (m, 5 H), 3.68-3.72 (m, 1.5 H), 4.01 (t, J = 5.6 Hz, 2 H), 4.57 (s, 2 H), 6.94 (d, J = 8.8 Hz, 2 H), 7.32 (d, J = 8.8 Hz, 2 H), 7.41-7.46 (m, 2 H), 8.01 (s, 1 H), 8.32 (d, J = 3.2 Hz, 0.8 H), 8.37 (d, J = 4.0 Hz, 0.24 H), 10.07 (bs, 0.8 H), 10.62 (bs, 0.23 H). |

TABLE 5-continued

| Cmpd # | Structure | Name | LCMS m/z [M + H]+ | 1H-NMR (400 MHz, DMSO-d6) |
|---|---|---|---|---|
| 72 | 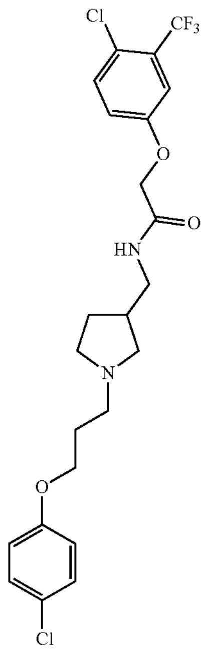 [SMILES: O=C(COc1ccc(Cl)c(C(F)(F)F)c1)NCC1CCN(CCCOc2ccc(Cl)cc2)C1] | 2-(4-chloro-3-(trifluoromethyl)phenoxy)-N-((1-(3-(4-chlorophenoxy)propyl)pyrrolidin-3-yl)methyl)acetamide | 505.0 | 1.33-1.34 (m, 1 H), 1.79-1.82 (m, 3 H), 2.24 (s, 2 H), 2.30-2.48 (m, 5 H), 3.07 (s, 2 H), 3.96 (t, J = 6.4 Hz, 2 H), 4.58 (s, 2 H), 6.91 (d, J = 8.4 Hz, 2 H), 7.23-7.28 (m, 3 H), 7.36 (s, 1 H), 7.62 (d, J = 8.8 Hz, 1 H), 8.18 (s, 1 H). |
| 73 | 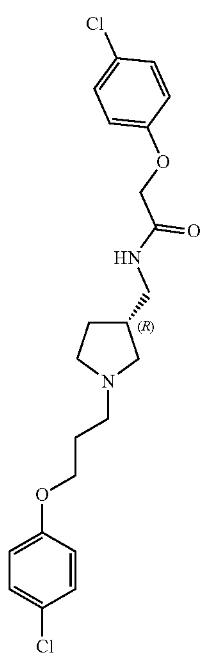 | (R)-2-(4-chlorophenoxy)-N-((1-(3-(4-chlorophenoxy)propyl)pyrrolidin-3-yl)methyl)acetamide | 437.1 | 1H NMR (400 MHz, CDCl3) δ ppm: 1.28-1.33 (m, 1 H), 2.00 (bs, 3 H), 2.49-2.80 (m, 7 H), 3.33-3.41 (m, 2 H), 3.97 (t, J = 6.4 Hz, 2 H), 4.45 (s, 2 H), 6.79 (d, J = 9.2 Hz, 2 H), 6.84 (d, J = 8.8 Hz, 2 H), 7.20-7.34 (m, 5 H). |

TABLE 5-continued
| Cmpd # | Structure | Name | LCMS m/z [M + H]+ | 1H-NMR (400 MHz, DMSO-d6) |
|---|---|---|---|---|
| 74 | ![structure] | 2-(4-chlorophenoxy)-N-((1-(3-(4-chlorophenoxy)propyl)-3-hydroxypyrrolidin-3-yl)methyl)acetamide | 454.31 | 1.65-1.97 (m, 4 H), 2.38-2.4 (m, 2 H), 2.6-2.65 (m, 3 H), 2.91-2.96 (m, 2 H), 3.43-3.59 (m, 2 H), 3.97 (t, J = 6.4 Hz, 2 H), 4.49 (s, 2 H), 6.8 (d, J = 8.8 Hz, 2 H), 6.86 (d, J = 8.4 Hz, 2 H), 7.04 (bs, 1 H), 7.21 (d, J = 8.4 Hz, 2 H), 7.26 (d, J = 8.8 Hz, 2 H). |
Example 75
2-(4-chlorophenoxy)-N-((1-(3-(4-chlorophenoxy)propyl)-2-oxopyrrolidin-3-yl)methyl)acetamide
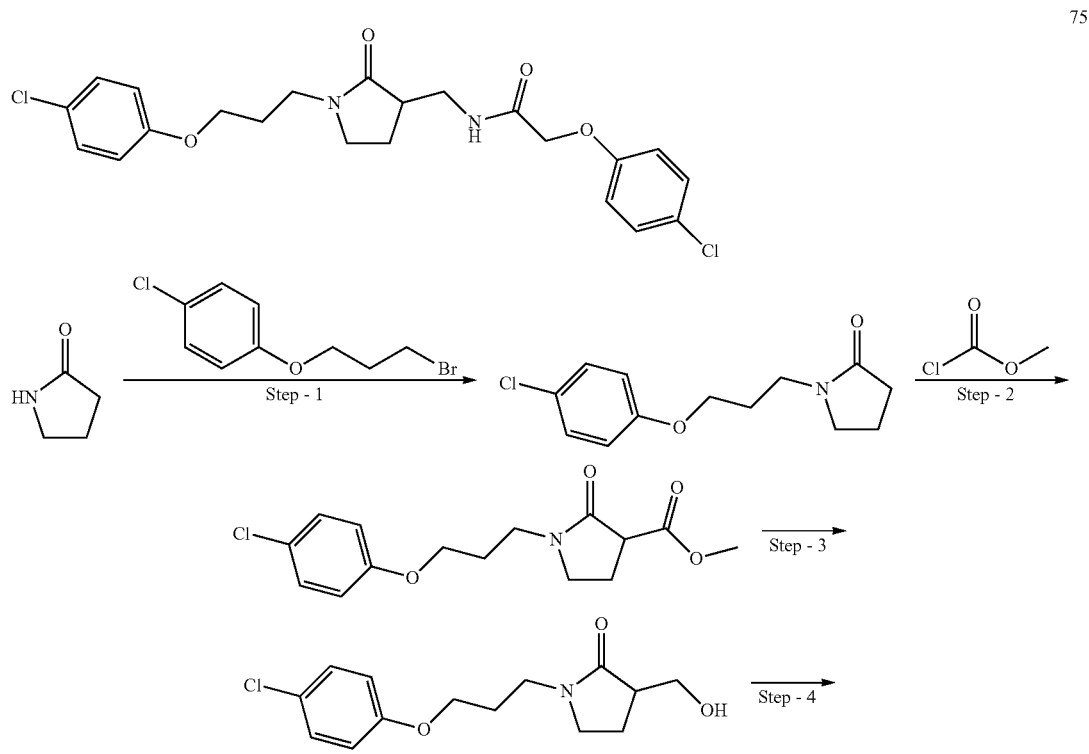

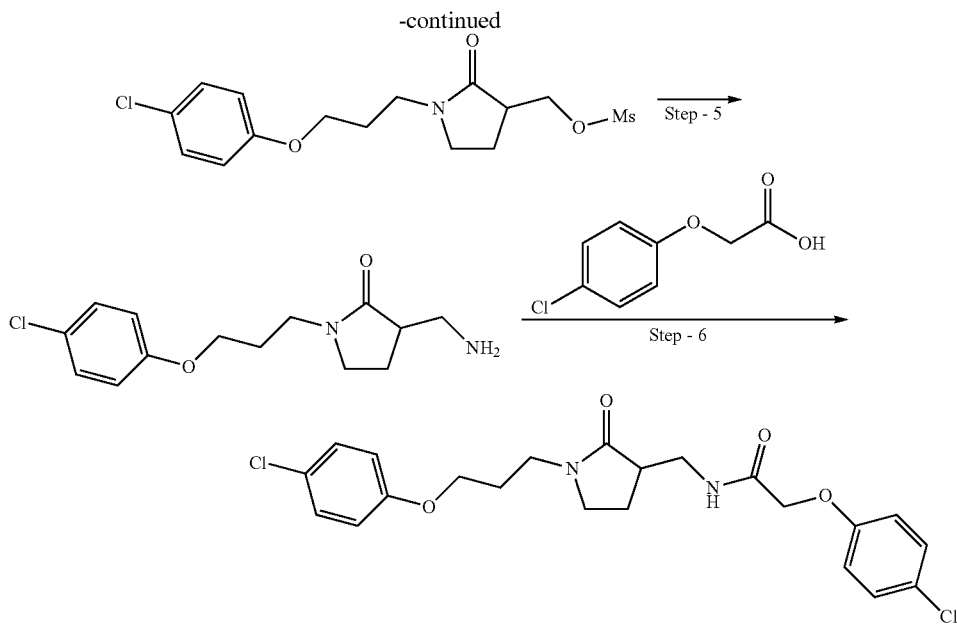

75

Step 1:

To a solution of pyrrolidin-2-one (1.0 g, 11.76 mmol, 1 equiv) in DMF (5 mL) was added sodium hydride 60% dispersion in mineral oil (0.51 g, 12.93 mmol, 1.1 equiv) portionwise at 0° C. This reaction mixture was stirred at room temperature for 30 minutes, after this time, 1-(3-bromopropoxy)-4-chlorobenzene (3.22 g, 12.93 mmol, 1.1 equiv) with DMF (2 mL) was added to the reaction mixture. Finally this reaction mixture was stirred at room temperature for 16 h at which time the staring materials were completely consumed. The reaction mixture was qunched with ice cold water (5 mL) and extracted with EtOAc (2×25 mL). The combined organic extract was washed with water (4×10 mL), brine (5.0 mL), dried over anhydrous sodium sulphate, filtered and concentrated under vacuum to give the crude product. The crude product was purified by flash column chromatography using a silica gel column and the product was eluted at 2.5% methanol in dichloromethane. Fractions containing the product were concentrated to give 1-(3-(4-chlorophenoxy)propyl)pyrrolidin-2-one (1.0 g, 33.67% yield) as colorless oil. LCMS (ES) m/z=254.0 [M+H]$^+$.

Step 2:

To a solution of 1-(3-(4-chlorophenoxy)propyl)pyrrolidin-2-one (0.7 g, 2.76 mmol, 1 equiv) in THF (10 mL) was added LiHMDS 1.0 M THF (6.07 mL, 6.07 mmol, 2.2 equiv) at −78° C. This reaction mixture was stirred at −78° C. for 5 minutes, after this time, methyl carbonochloridate (0.26 g, 2.76 mmol, 1.0 equiv) was added. After 10 minutes at −78° C., reaction mixture was qunched with saturated NH$_4$Cl solution (2 mL) and then product was extracted with EtOAc (15 mL). Organic layer was washed with brine (5.0 mL), dried over anhydrous sodium sulphate, filtered and concentrated under vacuum to give the crude product. The crude product was purified by flash column chromatography using a silica gel column and the product was eluted at 2.5% methanol in dichloromethane. Fractions containing the product were concentrated to give methyl 1-(3-(4-chlorophenoxy)propyl)-2-oxopyrrolidine-3-carboxylate (0.15 g, 17.44% yield) as colorless oil. LCMS (ES) m/z=312.1 [M+H]$^+$. $^1$H NMR (400 MHz, CDCl$_3$) δ ppm 2.00-2.06 (m, 2H), 2.24-2.28 (m, 1H), 2.38-2.43 (m, 1H), 3.36-3.57 (m, 5H), 3.75 (s, 3H), 3.95 (t, J=6.0 Hz, 2H), 6.80 (d, J=8.8 Hz, 2H), 7.22 (d, J=9.2 Hz, 2H).

Step 3:

To a solution of methyl 1-(3-(4-chlorophenoxy)propyl)-2-oxopyrrolidine-3-carboxylate (0.15 g, 0.48 mmol, 1 equiv) in methanol (5.0 mL) was added sodium borohydride (0.11 g, 2.89 mmol, 6.0 equiv) portionwise at 0° C. The reaction mixture was stirred at room temperature for 48 h at which time the starting materials were completely consumed. After this time, volatile portions were evaporated under vacuum and obtained crude was diluted with water (3 mL) and extracted with EtOAc (2×15 mL). The combined organic layers was dried over anhydrous sodium sulphate, filtered and concentrated under vacuum to give 1-(3-(4-chlorophenoxy)propyl)-3-(hydroxymethyl)pyrrolidin-2-one (0.14 g, 100% yield). LCMS (ES) m/z=284.2 [M+H]$^+$. $^1$H NMR (400 MHz, DMSO-d$_6$) δ ppm 1.85-1.92 (m, 3H), 1.96-2.04 (m, 1H), 2.30-2.38 (m, 2H), 3.28-3.31 (m, 2H), 3.52 (bs, 2H), 3.91 (t, J=6.4 Hz, 2H), 4.60 (s, 1H), 6.91 (d, J=8.8 Hz, 2H), 7.29 (d, J=8.8 Hz, 2H).

Step 4:

To a solution of 1-(3-(4-chlorophenoxy)propyl)-3-(hydroxymethyl)pyrrolidin-2-one (0.14 g, 0.49 mmol, 1 equiv) in DCM (7.0 mL) was added triethylamine (0.07 g, 0.73 mmol, 1.5 equiv) and mesyl chloride (0.07 g, 0.58 mmol, 1.2 equiv) at 0° C. The reaction mixture was stirred at room temperature for 7 h at which time the starting materials were completely consumed. After this time, volatile portions were evaporated under vacuum and obtained crude was diluted with water (7 mL) and the product was extracted with EtOAc (2×15 mL). The combined organic extract was washed with water (2×10 mL), brine (5.0 mL), dried over anhydrous sodium sulphate, filtered and concentrated under vacuum to give (1-(3-(4-chlorophenoxy)propyl)-2-oxopyrrolidin-3-yl)methyl methanesulfonate (0.18 g, 100% yield). LCMS (ES) m/z=362.1 [M+H]$^+$. $^1$H NMR (400 MHz, CDCl$_3$) δ ppm 2.03-2.09 (m, 2H), 2.23-2.30 (m, 1H), 2.77-2.82 (m, 1H), 2.98 (s, 3H), 3.38-3.56 (m, 5H), 3.94-3.95 (m, 2H), 4.40-4.47 (m, 2H), 6.81 (d, J=8.8 Hz, 2H), 7.22 (d, J=9.2 Hz, 2H).

Step 5:

To a solution of (1-(3-(4-chlorophenoxy)propyl)-2-oxopyrrolidin-3-yl)methyl methanesulfonate (0.18 g, 0.49 mmol, 1 equiv) in methanol (5.0 mL) was added saturated solution of ammonia in methanol (10 mL). The reaction mixture was stirred at 65° C. for 9 h at which time the starting materials were completely consumed. After this time, volatile portions were evaporated under vacuum to get 3-(aminomethyl)-1-(3-(4-chlorophenoxy)propyl)pyrrolidin-2-one (0.11 g, crude product). This crude product was carried to next step without any further purification. LCMS (ES) m/z=283.1 [M+H]$^+$.

Step 6:

To a solution of 2-(cyclohexyloxy)acetic acid (0.05 g, 0.28 mmol, 0.8 equiv) in DCM (7.0 mL) at 0° C. was added triethylamine (0.1 g, 1.05 mmol, 3 equiv) and T$_3$P 50 wt. % in ethyl acetate (0.16 g, 0.52 mmol, 1.5 equiv). After stirring for 5 minutes at 0° C., 3-(aminomethyl)-1-(3-(4-chlorophenoxy)propyl)pyrrolidin-2-one (0.1 g, 0.35 mmol, 1.0 equiv) was added and the reaction mixture was stirred at room temperature for 16 h at which time the starting materials were completely consumed. The reaction mixture was diluted with water (5 mL) and extracted with DCM (2×10 mL). The combined organic extract was washed with a saturated solution of aqueous NaHCO$_3$ (6.0 mL), water (5.0 mL), brine (5.0 mL) and dried over anhydrous sodium sulphate. The organic layer was filtered and concentrated under vacuum to give the crude product. The crude product was purified by flash column chromatography using a silica gel column and the product was eluted at 3% methanol in dichloromethane. Fractions containing the product were concentrated to give 2-(4-chlorophenoxy)-N-((1-(3-(4-chlorophenoxy)propyl)-2-oxopyrrolidin-3-yl)methyl)acetamide (15 mg, 12.5% yield) as white solid. LCMS (ES) m/z=451.1 [M+H]$^+$. $^1$H NMR (400 MHz, DMSO-d$_6$) δ ppm 1.65-1.67 (m, 1H), 1.85-1.88 (m, 2H), 2.00 (bs, 1H), 2.50-2.60 (m, 1H), 3.16-3.26 (m, 2H), 3.29-3.38 (m, 4H), 3.90-3.93 (m, 2H), 4.47 (s, 2H), 6.90-6.95 (m, 4H), 7.27-7.33 (m, 4H), 8.09 (bs, 1H).

TABLE 6

| Cmpd # | Structure | Name | LCMS m/z [M + H]$^+$ | $^1$H-NMR (400 MHz, DMSO-d$_6$) |
|---|---|---|---|---|
| 75 | 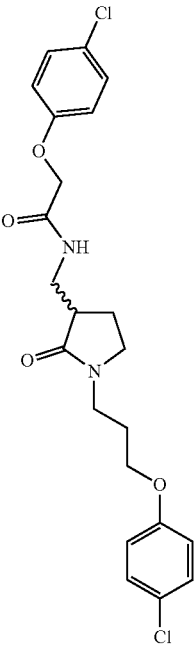 [SMILES: O=C(COc1ccc(Cl)cc1)NCC1CCN(CCCOc2ccc(Cl)cc2)C1=O] | 2-(4-chlorophenoxy)-N-((1-(3-(4-chlorophenoxy)propyl)-2-oxopyrrolidin-3-yl)methyl)acetamide | 451.1 | 1.65-1.67 (m, 1 H), 1.85-1.88 (m, 2 H), 2.00 (bs, 1 H), 2.50-2.60 (m, 1 H), 3.16-3.26 (m, 2 H), 3.29-3.38 (m, 4 H), 3.90-3.93 (m, 2 H), 4.47 (s, 2 H), 6.90-6.95 (m, 4 H), 7.27-7.33 (m, 4 H), 8.09 (bs, 1 H). |

Examples 76

2-(4-chlorophenoxy)-N-((1R,5S,6s)-3-(3-(4-chlorophenoxy)-2-hydroxypropyl)-3-azabicyclo[3.1.0]hexan-6-yl)acetamide

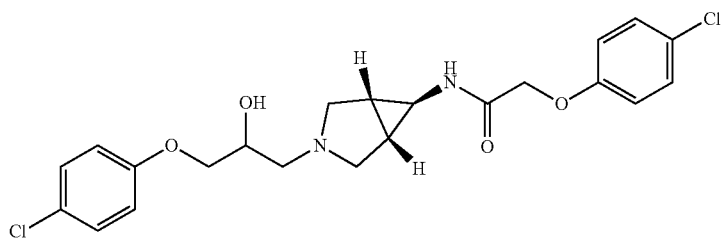

76

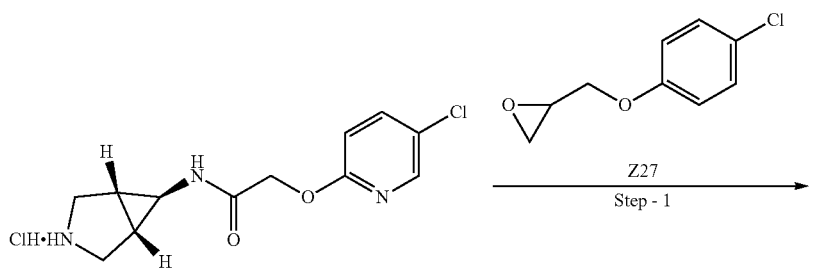

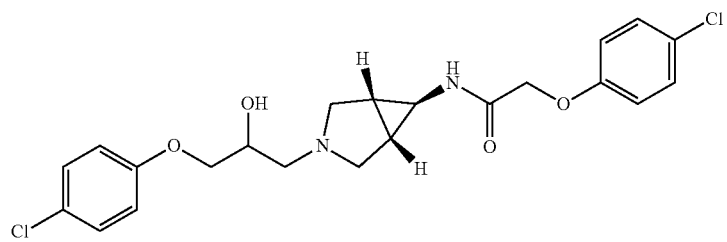

76

Step 1:—

To a stirred solution of N-((1R,5S,6S)-3-azabicyclo[3.1.0]hexan-6-yl)-2-(4-chlorophenoxy)acetamide hydrochloride (0.5 g, 1.65 mmol, 1 equiv) in ethanol (20 mL) was added (0.7 mL, 4.95 mmol, 3 equiv), 2-((4-chlorophenoxy)methyl)oxirane (0.36 g, 1.98 mmol, 1.2 equiv) drop wise added under cooling condition, it was stirred at room temperature for 16 hours, after completion of the reaction, reaction mixture was concentrated under reduced pressure to get the residue, residue was diluted with ethyl acetate (10 mL), water (5 mL), separated the organic layer, organic layer was dried over anhydrous $Na_2SO_4$, filtered and concentrated under reduced pressure to get the crude product. Crude was purified by flash column chromatography with silica-gel column using methanol in dichloromethane. Product was isolated at 2-3% methanol in dichloromethane to give the 2-(4-chlorophenoxy)-N-((1R,5S,6s)-3-(3-(4-chlorophenoxy)-2-hydroxypropyl)-3-azabicyclo[3.1.0]hexan-6-yl)acetamide (0.18 g, 24.59%) as an off-white solid. LCMS (ES) m/z=451.1 [M+H]$^+$. 1H NMR (400 MHz, DMSO-$d_6$): δ 1.49 (s, 2H), 2.31-2.40 (m, 3H), 2.48-2.52 (m, 1H), 2.80-2.84 (m, 1H), 3.01-3.05 (m, 2H), 3.77-3.80 (m, 2H), 3.88-3.91 (m, 1H), 4.39 (s, 2H), 4.81-4.82 (m, 1H), 6.94 (d, J=8.4 Hz, 4H), 7.32 (t, J=9.2 Hz, 4H), 8.02-8.03 (m, 1H).

The compound 77 was prepared generally according to the procedures described above for Example 76.

TABLE 7

| Cmpd # | Structure | Name | LCMS m/z [M + H]+ | 1H-NMR (400 MHz, DMSO-d6) |
|---|---|---|---|---|
| 76 | 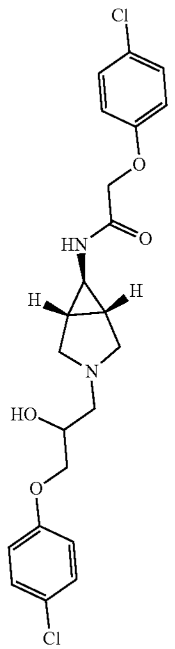 [SMILES: O=C(COc1ccc(Cl)cc1)N[C@H]1[C@@H]2CN(CC(O)COc3ccc(Cl)cc3)C[C@@H]21] | 2-(4-chlorophenoxy)-N-((1R,5S,6s)-3-(3-(4-chlorophenoxy)-2-hydroxypropyl)-3-azabicyclo[3.1.0]hexan-6-yl)acetamide | 451.1 | 1.49 (s, 2 H), 2.31-2.40 (m, 3 H), 2.48-2.52 (m, 1 H), 2.80-2.84 (m, 1 H), 3.01-3.05 (m, 2 H), 3.77-3.80 (m, 2 H), 3.88-3.91 (m, 1 H), 4.39 (s, 2 H), 4.81-4.82 (m, 1 H), 6.94 (d, J = 8.4 Hz, 4 H), 7.32 (t, J = 9.2 Hz, 4 H), 8.02-8.03 (m, 1 H). |
| 77 | 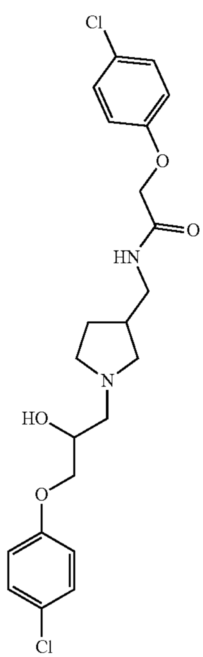 [SMILES: O=C(COc1ccc(Cl)cc1)NCC1CCN(CC(O)COc2ccc(Cl)cc2)C1] | 2-(4-chlorophenoxy)-N-((1-(3-(4-chlorophenoxy)-2-hydroxypropyl)pyrrolidin-3-yl)methyl)acetamide | 453.1 | 1.29-1.37 (m, 1 H), 1.77-1.89 (m, 1 H), 2.20-2.30 (m, 2 H), 2.50-2.65 (m, 5 H), 3.08-3.20 (m, 2 H), 3.83-3.85 (m, 2 H), 3.93-3.95 (m, 1 H), 4.45 (s, 2 H), 4.90-4.70 (m, 1 H), 6.92-6.95 (m, 4 H), 7.27-7.32 (m, 4 H), 8.11-8.2 (m, 1 H). |

Example 78

2-(4-chlorophenoxy)-N-((1R,5S,6s)-3-(3-(4-chlorophenoxy)-2-fluoropropyl)-3-azabicyclo[3.1.0]hexan-6-yl)acetamide

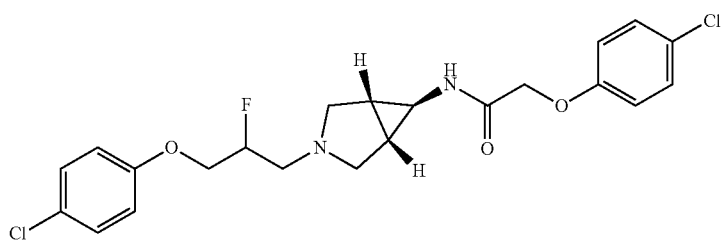

78

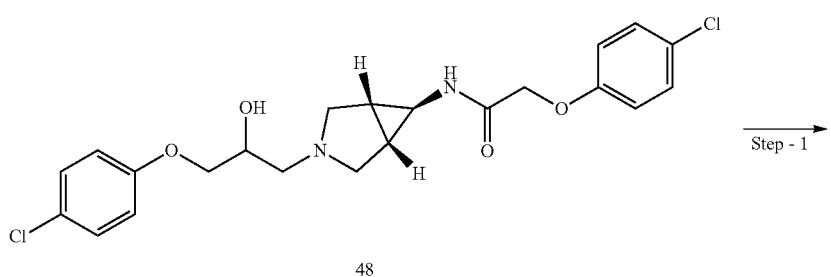

48

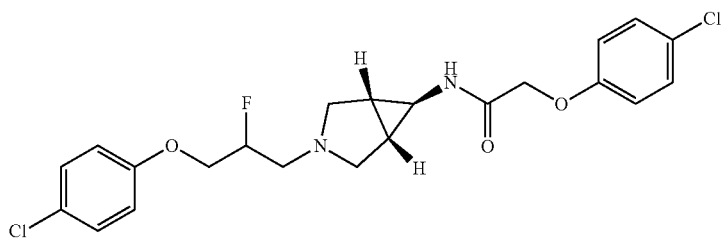

78

Step 1:—

To a stirred solution of 2-(4-chlorophenoxy)-N-((1R,5S,6S)-3-(3-(4-chlorophenoxy)-2-hydroxypropyl)-3-azabicyclo[3.1.0]hexan-6-yl)acetamide (0.12 g, 0.26 mmol, 1 equiv) in DCM, DAST (0.07 mL, 0.53 mmol, 2 equiv) was added at 0° C. and followed by ethanol 0.1 mL was added and stirred the reaction mixture was stirred at) rt (29° for 16 h. After completion of the reaction, reaction mixture was quenched with DCM 5 mL, and diluted with water 50 mL and extracted with DCM 50 mL×2, the combined organic layer was washed with sodium bicarbonate solution and dried over anhydrous Na2SO4, filtered and concentrated under reduced pressure and the crude product was purified by prep.TLC by using 30% Ethyl acetate:Hexane as an eluent to get the 2-(4-chlorophenoxy)-N-((1R,5S,6s)-3-(3-(4-chlorophenoxy)-2-fluoropropyl)-3-azabicyclo[3.1.0] hexan-6-yl)acetamide 0.007 g (5.8%) as a white solid. LCMS (ES) m/z=453.1 [M+H]$^+$. 1H NMR (400 MHz, DMSO-d$_6$): δ 1.52 (s, 2H), 2.39-2.48 (m, 2H), 2.69-2.70 (m, 1H), 2.74-2.76 (m, 1H), 2.80-2.82 (m, 1H), 3.03-3.06 (m, 2H), 4.03-4.19 (m, 2H), 4.40 (s, 2H), 4.80-4.81 (m, 0.5H), 4.92-4.93 (m, 0.5H), 6.92-6.97 (m, 4H), 7.32 (d, J=8.4 Hz, 4H), 8.04-8.05 (m, 1H).

TABLE 8
| Cmpd # | Structure | Name | LCMS m/z [M + H]+ | 1H-NMR (400 MHz, DMSO-d6) |
|---|---|---|---|---|
| 78 | 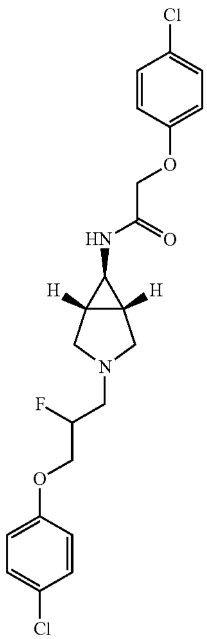 [SMILES: O=C(COc1ccc(Cl)cc1)N[C@H]1[C@@H]2CN(CC(F)COc3ccc(Cl)cc3)C[C@@H]21] | 2-(4-chlorophenoxy)-N-((1R,5S,6s)-3-(3-(4-chlorophenoxy)-2-fluoropropyl)-3-azabicyclo[3.1.0]hexan-6-yl)acetamide | 453.1 | 1.52 (s, 2 H), 2.39-2.48 (m, 2 H), 2.69-2.70 (m, 1 H), 2.74-2.76 (m, 1 H), 2.80-2.82 (m, 1 H), 3.03-3.06 (m, 2 H), 4.03-4.19 (m, 2 H), 4.40 (s, 2 H), 4.80-4.81 (m, 0.5 H), 4.92-4.93 (m, 0.5 H), 6.92-6.97 (m, 4 H), 7.32 (d, J = 8.4 Hz, 4 H), 8.04-8.05 (m, 1 H). |
Example 79
N-(4-chlorobenzyl)-3-((2-(4-chlorophenoxy)acetamido)methyl)-N-methylpyrrolidine-1-carboxamide
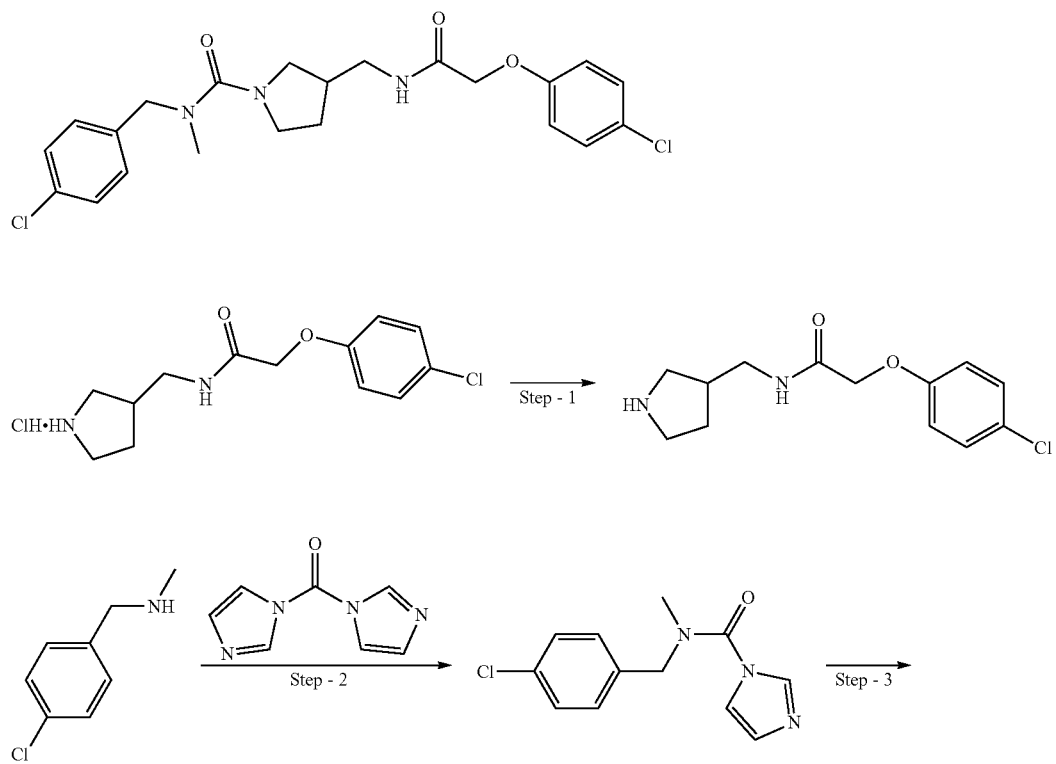

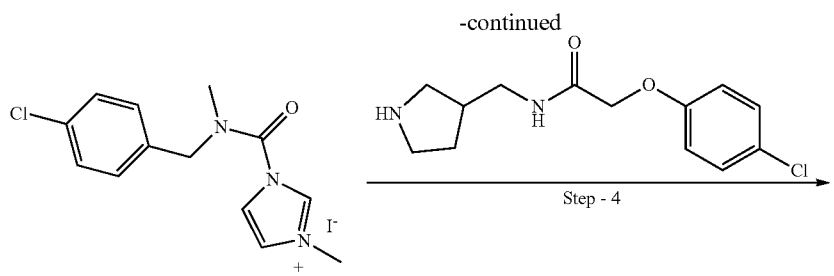

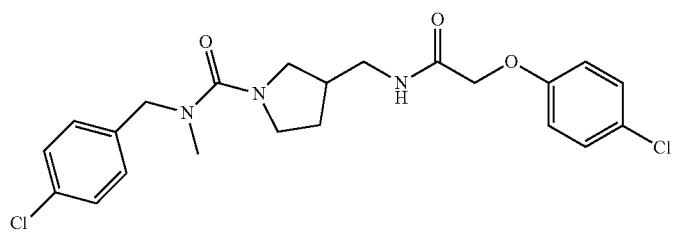

79

Step 1:

To a stirred solution of 2-(4-chlorophenoxy)-N-(pyrrolidin-3-ylmethyl)acetamide hydrochloride (1 g, 3.28 mmol, 1 equiv) in DCM (50 mL) was added aqueous NaHCO$_3$ solution (15 mL), it was stirred for 2 h at room temperature, after that the reaction mass was extracted with 5% MeOH in DCM (2×150 mL), combined organic layer over anhydrous sodium sulphate, filtered and concentrated to obtain 2-(4-chlorophenoxy)-N-(pyrrolidin-3-ylmethyl)acetamide (0.7 g, crude) as pale brown sticky solid. LCMS (ES) m/z=250.0 [M+H]$^+$. $^1$H NMR NMR (400 MHz, DMSO-d$_6$) δ ppm—crude.

Step 2:

To a solution of 1-(4-chlorophenyl)-N-methylmethanamine (0.5 g, 3.2 mmol, 1 equiv) in THF was added 1,1'-carbonyl diimidazole (0.573 g, 3.5 mmol, 1.1 equiv) at room temperature. The reaction mixture was maintained at 70° C. for 18 h, cooled to room temperature diluted with ethyl acetate (100 mL) washed with water (2×50 mL), organic layer was dried over anhydrous sodium sulphate, filtered and concentrated to obtain N-(4-chlorobenzyl)-N-methyl-1H-imidazole-1-carboxamide (0.75 g, crude, 94.93% yield) as yellow liquid. LCMS (ES) m/z=250.0 [M+H]$^+$. $^1$H NMR (400 MHz, DMSO-d$_6$) δ ppm—crude.

Step 3:

To a solution of N-(4-chlorobenzyl)-N-methyl-1H-imidazole-1-carboxamide (0.75 g 3.0 mmol, 1 equiv) in acetonitrile (10 mL) was added iodomethane (0.747 mL, 12 mmol, 4 equiv) at 0° C. The reaction mixture was maintained for 18 h at room temperature, the reaction mixture was concentrated to give crude product and washed with pentane (2×50 mL) and dried to obtain N-(4-chlorobenzyl)-N-methyl-1H-imidazole-1-carboxamide (1.1 g, crude, 94.01% yield) as yellow viscous liquid. LCMS (ES) m/z=264.1 [M+H]$^+$. (free amine mass was observed).

$^1$H NMR (400 MHz, DMSO-d$_6$) δ ppm—crude.

Step 4:

To a solution of 2-(4-chlorophenoxy)-N-(pyrrolidin-3-ylmethyl)acetamide (0.1 g, 3.7 mmol, 1 equiv) in DCM (30.0 mL) were added triethylamine (0.103 mL, 0.74 mmol, 2 equiv), N-(4-chlorobenzyl)-N-methyl-1H-imidazole-1-carboxamide (0.291 g, 0.74 mmol, 2 equiv) at 0° C. The reaction mixture was stirred at room temperature for 36 h, after completion of the starting material, reaction mixture was diluted with DCM (100 mL) and washed with cold water (2×50 mL), organic layer was dried over anhydrous sodium sulphate, filtered and concentrated to give crude, it was purified by flash chromatography using 0.5% to 5% methanol in DCM as an eluent to obtain N-(4-chlorobenzyl)-3-((2-(4-chlorophenoxy)acetamido)methyl)-N-methylpyrrolidine-1-carboxamide (0.05 g, 29.94% yield) as off white sticky solid. LCMS (ES) m/z=450.1 [M+H]$^+$. $^1$H NMR (400 MHz, DMSO-d$_6$) δ ppm 1.45-1.50 (m, 1H), 1.77-1.82 (m, 1H), 2.22-2.29 (m, 1H), 2.63 (s, 3H), 2.95-3.03 (m, 1H), 3.12 (t, J=6.0 Hz, 2H), 3.23-3.25 (m, 1H), 3.27-3.31 (m, 2H), 4.28 (s, 2H), 4.47 (s, 2H), 6.95 (d, J=8.8 Hz, 2H), 7.27 (d, J=8.0 Hz, 2H), 7.31 (d, J=8.8 Hz, 2H), 7.36 (d, J=8.4 Hz, 2H), 8.17 (bs, 1H).

TABLE 9
| Cmpd # | Structure | Name | LCMS m/z [M + H]+ | 1H-NMR (400 MHz, DMSO-d6) |
|---|---|---|---|---|
| 79 | 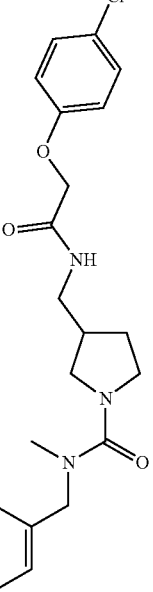 | N-(4-chlorobenzyl)-3-((2-(4-chlorophenoxy)acetamido)methyl)-N-methylpyrrolidine-1-carboxamide | 450.1 | 1.45-1.50 (m, 1 H), 1.77-1.82 (m, 1 H), 2.22-2.29 (m, 1 H), 2.63 (s, 3 H), 2.95-3.03 (m, 1 H), 3.12 (t, J = 6.0 Hz, 2 H), 3.23-3.25 (m, 1 H), 3.27-3.31 (m, 2 H), 4.28 (s, 2 H), 4.47 (s, 2 H), 6.95 (d, J = 8.8 Hz, 2 H), 7.27 (d, J = 8.0 Hz, 2 H), 7.31 (d, J = 8.8 Hz, 2 H), 7.36 (d, J = 8.4 Hz, 2 H), 8.17 (bs, 1 H). |
Example 80
2-(4-chlorophenoxy)-N-((1-(3-(4-chlorophenoxy)propyl)-4-hydroxypyrrolidin-3-yl)methyl)acetamide
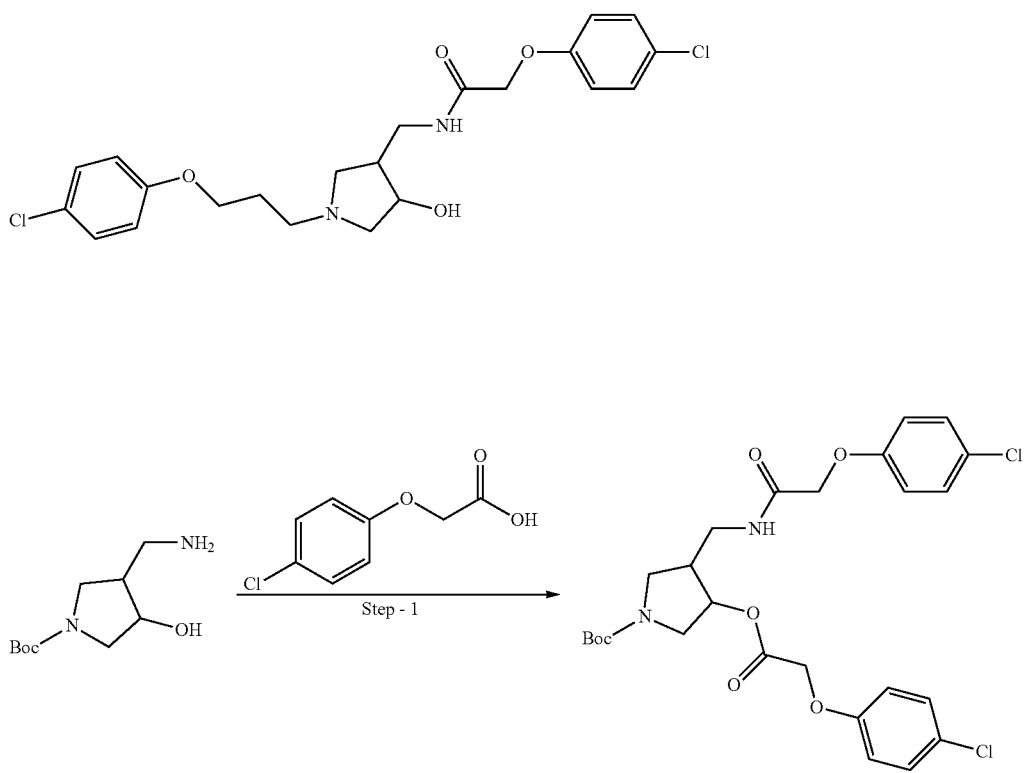

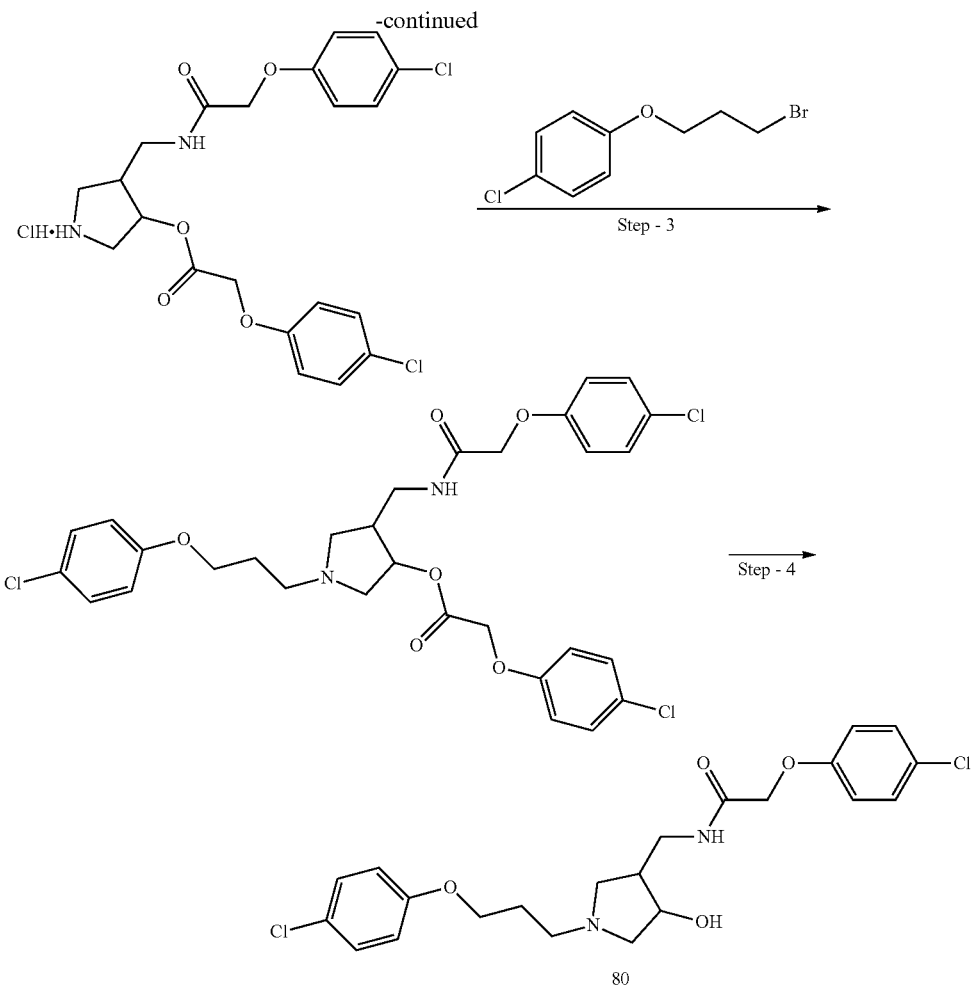

Step 1:

To a solution of tert-butyl 3-(aminomethyl)-4-hydroxypyrrolidine-1-carboxylate (0.25 g, 1.1 mmol, 1 equiv) in DCM (50.0 mL) were added diisopropyl ethylamine (0.76 mL, 4.4 mmol, 4 equiv), 2-(4-chlorophenoxy)acetic acid (0.474 g, 2.5 mmol, 2.2 equiv), EDC.HCl (0.479 g, 2.5 mmol, 2.2 equiv) and HOBT (0.33 g, 2.5 mmol, 2.2 equiv) at 0° C. The reaction mixture was stirred at room temperature for 6 h, after completion of the starting material, reaction mixture was diluted with DCM (150 mL) and washed with cold water (50 mL), 10% aqueous NaHCO$_3$ solution (2×50 mL), water (50 mL) and dried over anhydrous sodium sulphate. The organic layer was filtered and concentrated at rotavapor to give crude product. It was purified by flash chromatography using 5% to 50% ethyl acetate in hexane as an eluent to to obtain tert-butyl 3-((2-(4-chlorophenoxy)acetamido) methyl)-4-(2-(4-chlorophenoxy)acetoxy)pyrrolidine-1-carboxylate (0.34 g, 53.20% yield) as viscous liquid. LCMS (ES) m/z=497.1 [M+H]$^+$. (loss of t-butyl mass). $^1$H NMR (400 MHz, DMSO-d$_6$) δ ppm 1.42 (s, 9H), 2.30-2.48 (m, 1H), 3.09-3.13 (m, 3H), 3.20-3.27 (m, 2H), 3.57-3.60 (m, 1H), 4.47 (s, 2H), 4.79 (s, 2H), 5.03 (bs, 1H), 6.94 (d, J=8.4 Hz, 4H), 7.29 (d, J=9.2 Hz, 4H), 8.30 (bs, 1H).

Step 2:

To a solution of tert-butyl 3-((2-(4-chlorophenoxy)acetamido)methyl)-4-(2-(4-chlorophenoxy)acetoxy)pyrrolidine-1-carboxylate (0.35 g, 0.63 mmol, 1 equiv) in DCM (7.0 mL) was added 4M HCl in 1,4-dioxane (3.5 mL) at 0° C. The reaction mixture was stirred at room temperature for 16 h. After completion of starting material, the reaction mixture was concentrated to obtain 4-((2-(4-chlorophenoxy)acetamido)methyl)pyrrolidin-3-yl 2-(4-chlorophenoxy)acetate hydrochloride (0.25 g, crude, 80.90% yield) as sticky solid. LCMS (ES) m/z=453.1 [M+H]$^+$ (free amine mass was observed). $^1$H NMR (400 MHz, DMSO-d$_6$) δ ppm—crude.

Step 3:

To a solution of 4-((2-(4-chlorophenoxy)acetamido)methyl)pyrrolidin-3-yl 2-(4-chlorophenoxy)acetate hydrochloride (0.22 g, 0.44 mmol, 1 equiv) in DMF (4.4 mL) was added triethyl amine (2.20 mL) at 0° C. and maintained for 30 minutes at same temperature. After that 1-(3-bromopropoxy)-4-chlorobenzene (0.134 g, 0.53 mmol, 1.2 equiv) was added and maintained for 16 h at room temperature. After completion of starting material, the reaction mixture was diluted with crushed ice and extracted with ethyl acetate (2×50 mL). The combined organic extracts was washed with cold water (25 mL), dried over anhydrous sodium sulphate. The organic layer was filtered and concentrated at rotavapor to give crude product, It was purified by flash chromatography using 5% to 70% ethyl acetate in hexane as an eluent to afford 4-((2-(4-chlorophenoxy)acetamido)methyl)-1-(3-(4-chlorophenoxy)propyl)pyrrolidin-3-yl 2-(4-chlorophenoxy)acetate (0.10 g, 39.52% yield) as off white sticky solid. LCMS (ES) m/z=621.1 [M+H]$^+$. $^1$H NMR (400 MHz, DMSO-d$_6$) δ ppm 0.86-0.99 (m, 4H), 1.40-1.44 (m, 1H), 2.31-2.95 (m, 4H), 3.45-3.59 (m, 2H), 3.99 (t, J=5.6 Hz, 2H), 4.44 (s, 2H), 4.63 (s, 2H), 5.06 (bs, 1H), 6.79-6.81 (m, 4H), 6.82-6.86 (m, 2H), 7.21-7.25 (m, 6H), 7.51-7.53 (m, 0.5H), 7.69-7.71 (m, 0.5H).

Step 4:

To a stirred solution of 4-((2-(4-chlorophenoxy)acetamido)methyl)-1-(3-(4-chlorophenoxy)propyl)pyrrolidin-3-yl 2-(4-chlorophenoxy)acetate (0.10 g, 0.16 mmol, 1.0 equiv) in methanol (5 mL), was added 2N aqueous sodium hydroxide solution (0.5 mL) and stirred for 2 h at room temperature. Reaction mixture was evaporated, diluted with water (20 mL) and extracted with DCM (2×50 mL), the combined organic extracts was washed with cold water (20 mL), dried over anhydrous sodium sulphate. The organic layer was filtered and concentrated at rotavapor to give crude product, It was purified by flash chromatography using 1% to 5% methanol in DCM as an eluent to afford 2-(4-chlorophenoxy)-N-((1-(3-(4-chlorophenoxy)propyl)-4-hydroxypyrrolidin-3-yl)methyl)acetamide (0.06 g, 83.33% yield) as white solid. LCMS (ES) m/z=453.1 [M+H]$^+$. $^1$H NMR (400 MHz, DMSO-d$_6$) δ ppm 1.75-1.81 (m, 2H), 2.03-2.19 (m, 1H), 2.26-2.29 (m, 1H), 2.30-2.37 (m, 1H), 2.38-2.44 (m, 1H), 2.48-2.56 (m, 2H), 2.65 (t, J=7.8 Hz, 1H), 3.06-3.22 (m, 2H), 3.77-3.79 (m, 1H), 3.96 (t, J=6.4 Hz, 2H), 4.45 (s, 2H), 4.76 (d, J=5.2 Hz, 1H), 6.90-6.95 (m, 4H), 7.26-7.32 (m, 4H), 8.08 (t, J=5.4 Hz, 1H).

TABLE 10

| Cmpd # | Structure | Name | LCMS m/z [M + H]$^+$ | $^1$H-NMR (400 MHz, DMSO-d$_6$) |
|---|---|---|---|---|
| 80 | 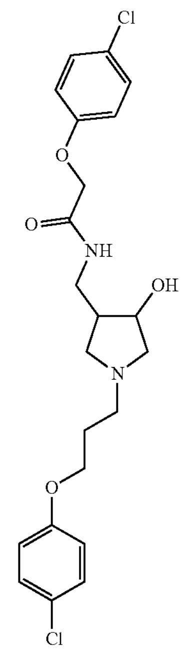 [SMILES: O=C(COc1ccc(Cl)cc1)NCC1CN(CCCOc2ccc(Cl)cc2)CC1O] | 2-(4-chlorophenoxy)-N-((1-(3-(4-chlorophenoxy)propyl)-4-hydroxypyrrolidin-3-yl)methyl)acetamide | 453.1 | 1.75-1.81 (m, 2 H), 2.03-2.19 (m, 1 H), 2.26-2.29 (m, 1 H), 2.30-2.37 (m, 1 H), 2.38-2.44 (m, 1 H), 2.48-2.56 (m, 2 H), 2.65 (t, J = 7.8 Hz, 1 H), 3.06-3.22 (m, 2 H), 3.77-3.79 (m, 1 H), 3.96 (t, J = 6.4 Hz, 2 H), 4.45 (s, 2 H), 4.76 (d, J = 5.2 Hz, 1 H), 6.90-6.95 (m, 4 H), 7.26-7.32 (m, 4 H), 8.08 (t, J = 5.4 Hz, 1 H). |

Example 81

2-(4-chlorophenoxy)-N-((1-(3-(4-chlorophenoxy)propyl)-5-oxopyrrolidin-3-yl)methyl)acetamide

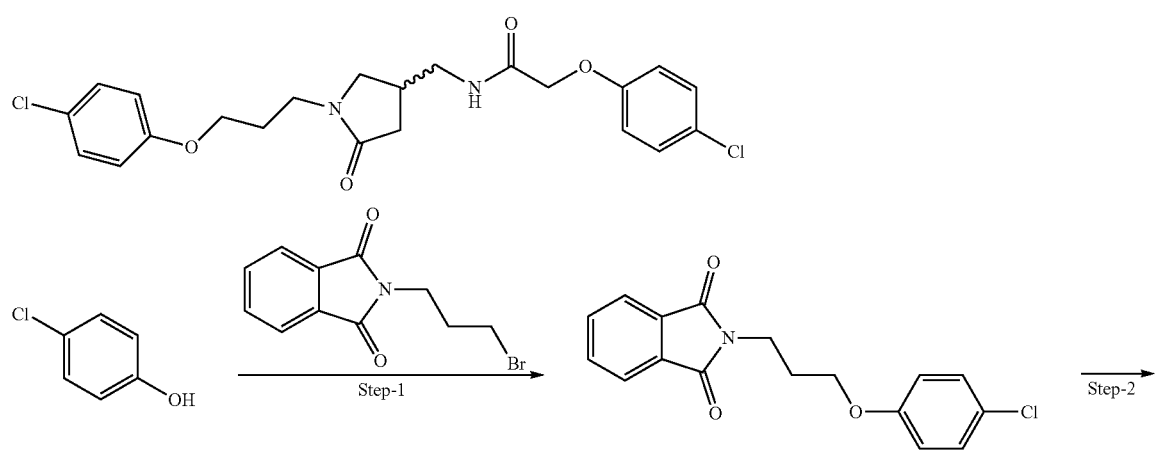

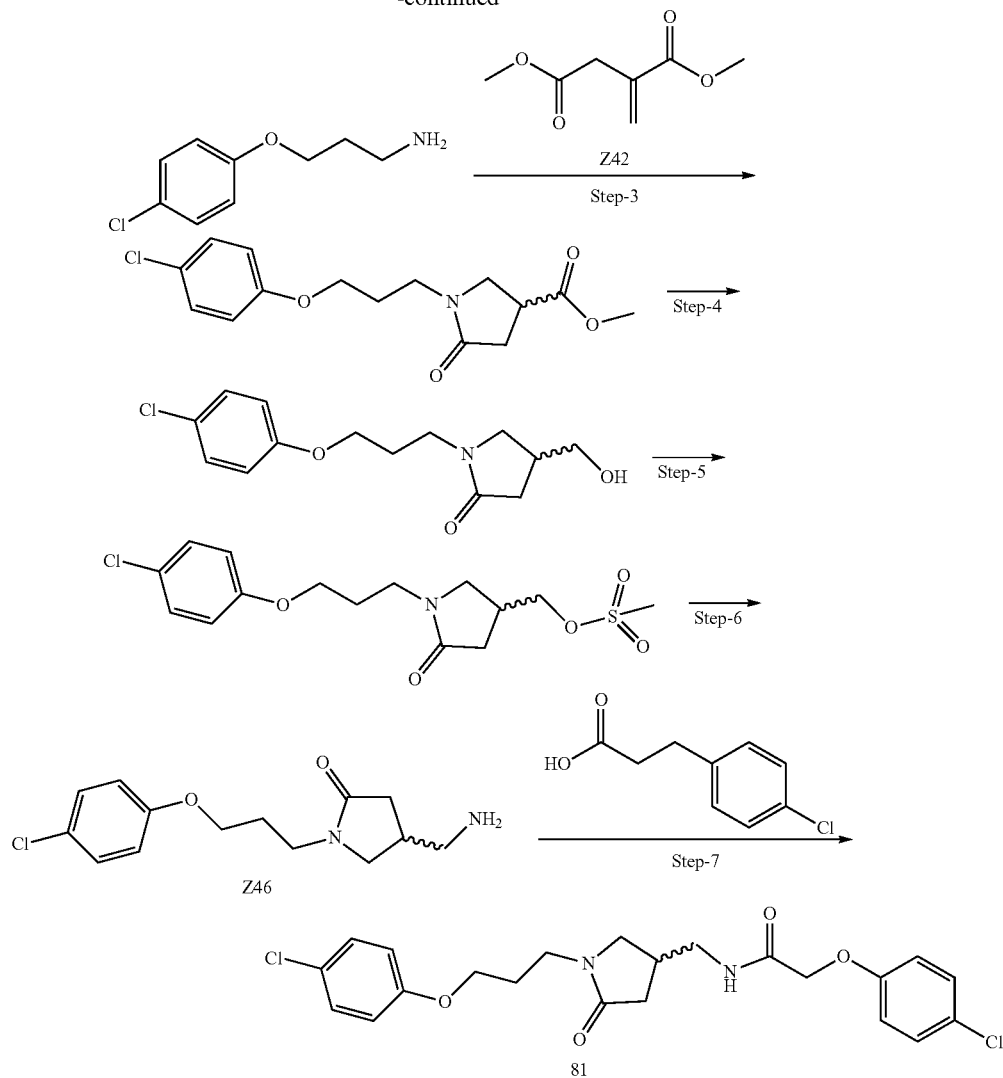

Step 1:

To a stirred solution of 4-chlorophenol (2.0 g, 15.55 mmol, 1.0 equiv.) in THF (50 mL) was added 2-(3-bromopropyl) isoindoline-1,3-dione (4.59 g, 17.112 mmol, 1.1 equiv), and TBAI (1.15 g, 3.11 mmol, 0.2 equiv). Finally cesium carbonate (9.1 g, 28.0 mmol, 1.8 eq.) was added at rt (29° C.) and heated the reaction at 50° C. for 16 h. After completion of the reaction, reaction mixture was quenched with water and extracted ethyl acetate (50 mL×3); the combined organic layer was washed with brine solution and dried over anhydrous sodium sulphate, filtered and concentrated to get the crude product. The crude product was carried to next step without any further purification. Weight: 4.9 g crude (Off-white solid). LC-MS: 316.1 [M+H]$^+$. 1H NMR (400 MHz, DMSO-d6): δ ppm—2.0-2.06 (m, 2H), 3.74 (t, J=6.4 Hz, 2H), 3.98 (t, J=5.6 Hz, 2H), 6.79 (d, J=8.8 Hz, 2H), 7.24 (d, J=8.8 Hz, 2H), 7.79-7.85 (m, 4H).

Step 2:

To a stirred solution of 2-(3-(4-chlorophenoxy)propyl) isoindoline-1,3-dione (1.0 g, 3.17 mmol, 1.0 equiv.) in ethanol (20 mL) was added hydrazine monohydrate (5 mL) and heated the reaction at 60° C. for 16 h. After completion of the reaction, reaction mixture was cooled to room temperature (29° C.) and diluted with diethyl ether and stirred for 10 min. The resulting precipitate was filtered through the sintered funnel and washed with ether. The filtrate was concentrated under reduced pressure to get the crude product; the crude product was carried to next step without any further purification. Weight=0.58 g crude, as pale yellow liquid. LC-MS: 186.1 [M+H]$^+$.

Step 3:

To a stirred solution of compounds 3-(4-chlorophenoxy) propan-1-amine (0.38 g, 2.05 mmol) in methanol, dimethyl 2-methylenesuccinate (0.43 mL g, 3.08 mmol) was added and heated the reaction mixture in a sealed tube at 65° C. for 16 h. after completion of the reaction, reaction mixture was concentrated under vacuum, obtained crude product was purified by using silica gel column chromatography by using 3% MeOH: DCM. Yield: 0.65 g (100%). LC-MS: 312.1 [M+H]$^+$. 1H NMR (400 MHz, DMSO-d$_6$): δ ppm—1.84-1.9 (m, 2H), 2.38-2.54 (m, 2H), 3.23-3.35 (m, 3H), 3.46-3.6 (m, 2H), 3.62 (s, 3H), 3.92 (t, J=5.6 Hz, 2H), 6.91 (d, J=8.8 Hz, 2H), 7.29 (d, J=8.8 Hz, 2H).

Step 4:

To a solution of methyl 1-(3-(4-chlorophenoxy)propyl)-5-oxopyrrolidine-3-carboxylate (0.65 g, 2.08 mmol) in MeOH was added Sodium borohydride (0.63 g, 16.68 mmol) was added portion wise at 0° C., this reaction mixture was stirred at room temperature for 5 h. After completion of the reaction, reaction mixture was quenched with methanol and concentrated under vacuum and obtained crude was diluted with water (50 mL) and extracted with ethyl acetate (2×100 mL), the combined organic layer was washed with 50 mL of brine solution and dried over anhydrous $Na_2SO_4$, filtered and concentrated under vacuum. Crude weight: 0.65 g. LC-MS: 284.1 [M+H]+. $^1$H NMR (400 MHz, DMSO-$d_6$): δ ppm—1.83-1.89 (m, 2H), 1.95-2.01 (m, 1H), 2.24-2.4 (m, 2H), 3.09-3.41 (m, 6H), 3.92 (t, J=6 Hz, 2H), 4.72 (t, J=5.2 Hz, 1H), 6.92 (d, J=8.8 Hz, 2H), 7.29 (d, J=9.2 Hz, 2H).

Step 5:

To a stirred solution of 1-(3-(4-chlorophenoxy)propyl)-4-(hydroxymethyl)pyrrolidin-2-one (0.61 g, 2.15 mmol) in DCM (20 mL), was added triethylamine (0.45 mL, 3.23 mmol) followed by methanesulfonyl chloride (0.2 mL, 2.58 mmol). The reaction mixture was stirred at room temperature for 16 hours, after completion of the reaction, reaction mixture was diluted with ice water 30 mL and extracted with DCM 50λ2 mL, the combined organic layer was separated and was washed with brine solution and dried over anhydrous $Na_2SO_4$, filtered and evaporated under vacuum to get the crude product and the crude product was carried to next step without nay purification to next step. Crude weight: 0.77 g. LC-MS: 362 [M+H]$^+$.

Step 6:

To a solution of (1-(3-(4-chlorophenoxy)propyl)-5-oxopyrrolidin-3-yl)methyl methanesulfonate (0.7 g, 2.13 mmol) in MeOH was added methanolic ammonia (10 mL) at room temperature and heated the reaction mixture at 65° C. in auto cleave for 16 hours. After completion of the reaction, reaction mixture was concentrated under vacuum to get the crude product and the crude product was carried to next step without any purification.

Yield: 0.77 g (crude). LC-MS: 283.1 [M+H]$^+$

Step 7:

To a stirred solution of 4-(aminomethyl)-1-(3-(4-chlorophenoxy)propyl)pyrrolidin-2-one (0.3 g, 1.06 mmol, 1.0 equiv) in DCM (10 mL), triethyl amine (0.44 mL, 3.18 mmol, 3.0 equiv) and 2-(4-chlorophenoxy)acetic acid (0.12 g, 1.06 mmol, 1.0 equiv.) were added. Finally T3P (50 wt. % in ethyl acetate) (0.95 mL, 1.59 mmol, 1.5 equiv.) was added. Then reaction mixture was stirred at room temperature (29° C.) for 16h. After completion of the reaction, reaction mixture was diluted with water (20 mL), extracted with DCM (2×50 mL), the combined organic layer was dried over anhydrous sodium sulphate, filtered and concentrated under reduced pressure to get the crude product. The crude product was purified by silica gel column chromatography by using 4% MeOH in DCM.

Yield: 0.047 g (9.8%) as gummy liquid. LC-MS (ES) m/z: 451.3 [M+H]+. $^1$H NMR (400 MHz, DMSO-$d_6$): δ ppm— 1.96-2.02 (m, 2H), 2.11-2.16 (m, 1H), 2.48-2.55 (m, 1H), 2.59-2.66 (m, 1H), 3.13-3.17 (m, 1H), 3.28-3.35 (m, 1H), 3.42-3.53 (m, 4H), 3.94 (t, J=5.6 Hz, 2H), 4.45 (s, 2H), 6.65 (bs, 1H), 6.79-6.85 (m, 4H), 7.21 (d, J=8.8 Hz, 2H), 7.27 (d, J=8.8 Hz, 2H).

TABLE 11

| Cmpd # | Structure | Name | LCMS m/z [M + H]$^+$ | $^1$H-NMR (400 MHz, DMSO-$d_6$) |
|---|---|---|---|---|
| 81 | 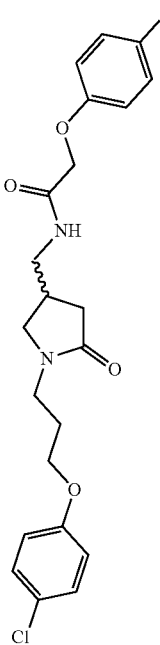 | 2-(4-chlorophenoxy)-N-((1-(3-(4-chlorophenoxy)propyl)-5-oxopyrrolidin-3-yl)methyl)acetamide | 421.1 | 1.96-2.02 (m, 2 H), 2.11-2.16 (m, 1 H), 2.48-2.55 (m, 1 H), 2.59-2.66 (m, 1 H), 3.13-3.17 (m, 1 H), 3.28-3.35 (m, 1 H), 3.42-3.53 (m, 4 H), 3.94 (t, J = 5.6 Hz, 2 H), 4.45 (s, 2 H), 6.65 (bs, 1 H), 6.79-6.85 (m, 4 H), 7.21 (d, J = 8.8 Hz, 2 H), 7.27 (d, J = 8.8 Hz, 2 H). |

Example 82

4-(4-chlorophenoxy)-2-((1R,5S)-6-(2-(4-chlorophenoxy)acetamido)-3-azabicyclo[3.1.0]hexan-3-yl)butanoic acid hydrochloride

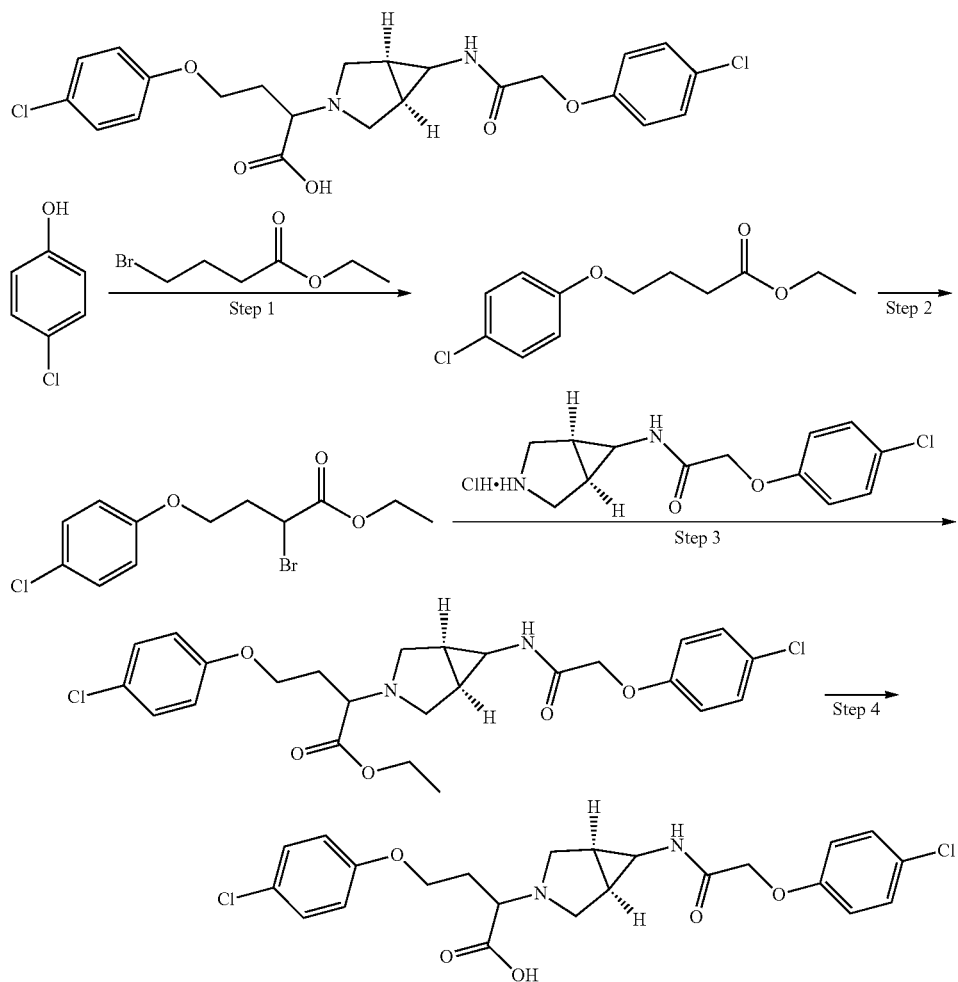

white solid. LCMS (ES) m/z=243.1 [M+H]$^+$. $^1$H NMR (400 MHz, CDCl3): δ ppm 1.25 (t, J=7.2 Hz, 3H), 2.06-2.12 (m, 2H), 2.49 (t, J=7.6 Hz, 2H), 3.97 (t, J=6.0 Hz, 2H), 4.11-4.17 (m, 2H), 6.80 (d, J=8.8 Hz, 2H), 7.21 (d, J=8.8 Hz, 2H).

Step 1:

To a solution of 4-chlorophenol (10 g, 77.784 mmol, 1 equiv) in N,N-dimethylformamide (100 mL) was added anhydrous potassium carbonate (21.5 g, 116.6 mmol, 2 equiv) and ethyl 4-bromobutanoate (16.7 mL, 116.677 mmol, 1.5 equiv). The reaction mixture was heated to 140° C. and stirred for 4 h. The progress of the reaction was monitored by TLC. After completion of reaction, the reaction mixture was allowed to cool to 27° C., filtered the solid and washed with ethyl acetate (700 mL). The filtrate was washed with water (2×200 mL), brine solution (100 mL), dried over anhydrous sodium sulphate, filtered and concentrated under reduced pressure to give the crude product. The crude product was purified by silica gel column chromatography using 10% ethyl acetate in hexane as eluent to obtain ethyl 4-(4-chlorophenoxy)butanoate (17.0 g, 89% yield) as Step 2:

To a solution of ethyl 4-(4-chlorophenoxy)butanoate (2.0 g, 8.240 mmol, 1.0 equiv) in dry tetrahydrofuran (30 mL) was added lithium diisopropylamide solution (2.0 M in THF/heptane/ethylbenzene) (6.2 mL, 12.36 mmol, 1.5 equiv) slowly at −78° C. The reaction mixture was stirred for another 1 h at −78° C. After 1 h, a solution of carbon tetrabromide (4.0 g, 12.36 mmol, 1.5 equiv) in dry tetrahydrofuran (30 mL) was added at −78° C., the mixture was gradually allowed to warm to 27° C. and then stirred for 2 h. The mixture was quenched with saturated aqueous solution of ammonium chloride (100 mL) and extracted with ethyl acetate (3×100 mL). The combined organics were dried over anhydrous sodium sulphate, filtered and concentrated under reduced pressure to give the crude product. The crude product was purified by silica gel column chromatography using 10% ethyl acetate in hexane as eluent to obtain ethyl 2-bromo-4-(4-chlorophenoxy)butanoate (0.45 g, 17% yield) as colourless liquid. $^1$H NMR (400 MHz, CDCl3): δ ppm 1.30 (t, J=7.2 Hz, 3H), 2.36-2.43 (m, 1H), 2.52-2.59 (m, 1H), 4.06-4.10 (m, 2H), 4.22-4.27 (m, 2H), 4.52-4.55 (m, 1H), 6.81 (d, J=8.8 Hz, 2H), 7.23 (d, J=8.8 Hz, 2H).

Step 3:

To a solution of N-((1R,5S)-3-azabicyclo[3.1.0]hexan-6-yl)-2-(4-chlorophenoxy)acetamide hydrochloride (0.2 g, 0.659 mmol, 1 equiv) in N,N-dimethylformamide (2 mL) were added ethyl 2-bromo-4-(4-chlorophenoxy)butanoate (0.42 g, 1.319 mmol, 2 equiv) and triethyl amine (0.28 mL, 1.979 mmol, 3.0 equiv). The resulting mixture was stirred for 16 h at 27° C. The progress of the reaction was monitored by TLC. After completion of reaction, the reaction mixture was quenched with water (50 mL) and extracted with ethyl acetate (3×30 mL). The combined organics were washed with water (30 mL), brine solution (20 mL), dried over anhydrous sodium sulphate, filtered and concentrated under reduced pressure to obtain the crude product. which was purified by silica gel column chromatography using 60% ethyl acetate in hexane as eluent to obtain ethyl 4-(4-chlorophenoxy)-2-((1R,5S)-6-(2-(4-chlorophenoxy)acetamido)-3-azabicyclo[3.1.0]hexan-3-yl)butanoate (0.16 g, 47% yield) as pale brown solid. LCMS (ES) m/z=507.1 [M+H]$^+$. $^1$H NMR (400 MHz, CDCl3): δ ppm 1.25 (t, J=7.2 Hz, 5H), 2.00-2.09 (m, 1H), 2.13-2.20 (m, 1H), 2.85-2.96 (m, 3H), 3.07 (t, J=8.4 Hz, 2H), 3.56-3.59 (m, 1H), 3.91-3.97 (m, 2H), 3.97-4.18 (m, 2H), 4.41 (s, 2H), 6.44 (bs, 1H), 6.78-6.83 (m, 4H), 7.21 (d, J=8.8 Hz, 2H), 7.26 (d, J=8.8 Hz, 2H).

Step 4:

To a solution of ethyl 4-(4-chlorophenoxy)-2-((1R,5S)-6-(2-(4-chlorophenoxy)acetamido)-3-azabicyclo[3.1.0]hexan-3-yl)butanoate (0.13 g, 0.256 mmol, 1 equiv) in a mixture of tetrahydrofuran (5 mL) and water (2 mL) was added lithium hydroxide monohydrate (0.1 g, 2.562 mmol, 10 equiv). The mixture was heated to 50° C. and stirred for 16 h. The progress of the reaction was monitored by TLC. After completion of reaction, the mixture was diluted with cold water (10 mL), acidified with 1.5 M hydrochloric acid to pH~2 to 3 at 0° C. The aqueous layer was extracted with ethyl acetate (3×50 mL). The combined organic layer was washed with water (30 mL), brine solution (30 mL), dried over anhydrous sodium sulphate, filtered and concentrated under reduced pressure to obtain crude product. The crude product was recrystalised by using dichloromethane to obtain 4-(4-chlorophenoxy)-2-((1R,5S)-6-(2-(4-chlorophenoxy)acetamido)-3-azabicyclo[3.1.0]hexan-3-yl)butanoic acid (0.075 g, 62% yield) as white solid. LCMS (ES) m/z=479.0 [M+H]$^+$. $^1$H NMR (400 MHz, DMSO-d$_6$): δ ppm 1.52-1.54 (m, 2H), 1.92-1.96 (m, 1H), 2.00-2.05 (m, 1H), 2.76 (s, 2H), 2.85-2.93 (m, 3H), 3.38-3.42 (m, 1H), 3.94-3.95 (m, 2H), 4.40 (s, 2H), 6.91-6.94 (m, 4H), 7.27-7.32 (m, 4H), 8.05 (d, J=3.2 Hz, 1H). $^{13}$C NMR (100 MHz, DMSO-d$_6$): δ ppm 22.88-23.05, 29.95, 30.28, 47.61, 52.18, 59.07, 65.46, 67.62, 116.70, 116.95, 124.65, 125.27, 129.63, 129.67, 157.11, 157.82, 168.47, 173.35.

TABLE 12

| Cmpd # | Structure | Name | LCMS m/z [M + H]$^+$ | $^1$H-NMR (400 MHz, DMSO-d$_6$) |
|---|---|---|---|---|
| 82 | 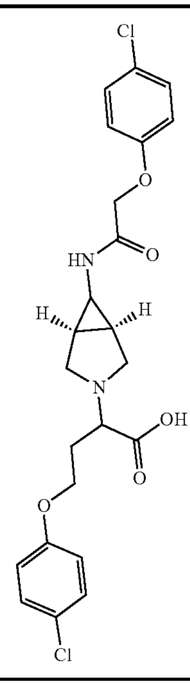 | 4-(4-chlorophenoxy)-2-((1R,5S)-6-(2-(4-chlorophenoxy)acetamido)-3-azabicyclo[3.1.0]hexan-3-yl)butanoic acid | 479 | 1.52-1.54 (m, 2 H), 1.92-1.96 (m, 1 H), 2.00-2.05 (m, 1 H), 2.76 (s, 2 H), 2.85-2.93 (m, 3 H), 3.38-3.42 (m, 1 H), 3.94-3.95 (m, 2 H), 4.40 (s, 2 H), 6.91-6.94 (m, 4 H), 7.27-7.32 (m, 4 H), 8.05 (d, J = 3.2 Hz, 1 H). |

Enantiomer separation of Examples 11 and 12:

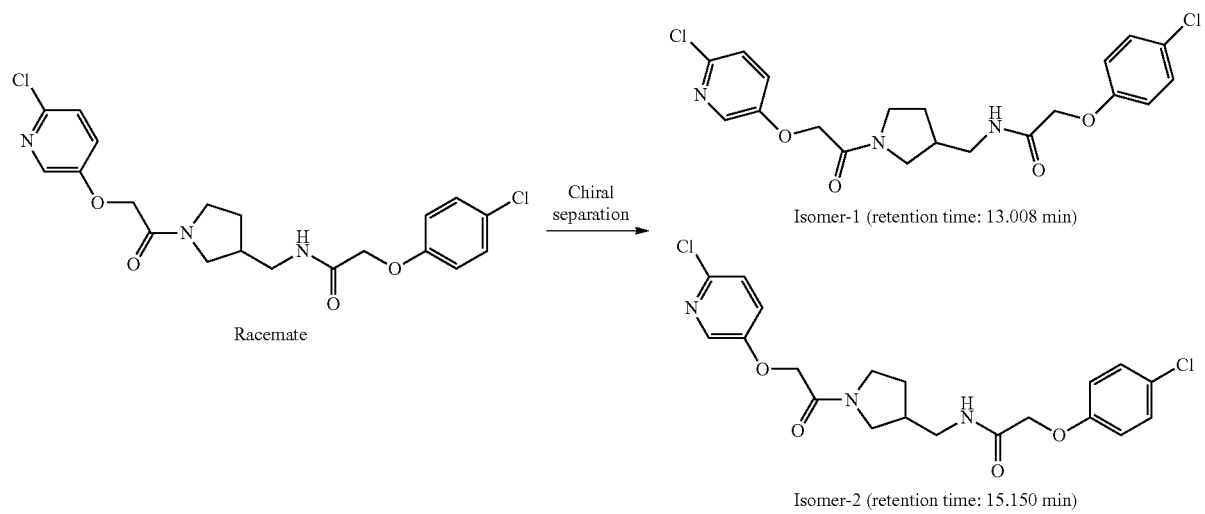 [SMILES: O=C(COc1ccc(Cl)cc1)NCC1CCN(C(=O)COc2ccc(Cl)nc2)C1 ; O=C(COc1ccc(Cl)cc1)NCC1CCN(C(=O)COc2ccc(Cl)nc2)C1 ; O=C(COc1ccc(Cl)cc1)NCC1CCN(C(=O)COc2ccc(Cl)nc2)C1]

Chiral separation of 2-(4-chlorophenoxy)-N-((1-(2-((6-chloropyridin-3-yl)oxy)acetyl)pyrrolidin-3-yl)methyl)acetamide The racemate compound 2-(4-chlorophenoxy)-N-((1-(2-((6-chloropyridin-3-yl)oxy)acetyl)pyrrolidin-3-yl)methyl)acetamide (0.320 g, 0.729 mmol) was resolved into two enantiomers by chiral prep purification using the following HPLC condition.
Column: Chiralpak IA (250 mm×4.6 mm×5 μm)
Mobile phase: MTBE:MeOH with 0.1% DEA (85:15)
Flow rate: 1.0 mL/min.

The peak eluting at 13.008 min was assigned as isomer—1 with and that eluting at 15.150 min was assigned as isomer—2. Both the purified fractions were evaporated under vacuo to afford 0.102 g of isomer—1 (chiral purity 99.86%) and 0.112 g of isomer—2 (chiral purity 95.59%, ee 91.18%) as white solid.

Note:
For isomer—1, the ee was not calculated because of the minor impurity at 20.235 min (0.14%). However, there is no contamination of isomer—2 in the isomer—1 fraction as evident from chiral HPLC of the individual isomers.

Example 83: ATF4 Cell Based Assay

The ATF4 reporter assay measures the effect of Thapsigargin induced cellular stress on ATF4 expression. For this reporter assay, a stable cell line was created by transfecting SH-SY5Y cells with a plasmid containing the NanoLuc® luciferase gene fused to the 5'-UTR of ATF4, under the control of the CMV promoter. The ATF4 5'-UTR contains two open reading frames which mediate the cellular stress-dependent translation of the reporter gene. Clones stably expressing the reporter construct were isolated and selected based on the luminescence response to thapsigargin and inhibition of this signal by test compounds. Briefly, SH-SY5Y-ATF4-NanoLuc cells were challenged with Thapsigargin for 14-18 hours to determine the stress effect with or without test compounds.

Cells were propagated in growth media consisting of 90% DMEM F12 (InVitrogen #11320-033), 10% Fetal Bovine Serum (Gibco #10438-026), 5 mM Glutamax (Gibco #35050-061), 5 mM Hepes, (Gibco #15630-080), and 0.5 mg/ml Geneticin (Gibco #10131-027). Cells were prepared for the assay by removing all media from cells, washing the plated cells with phosphate buffered saline, and detached by adding a solution comprised of 10% Tryple express solution (InVitrogen12604-021) and 90% enzyme-free cell dissociation buffer HANKS base (Gibco 13150-016). The trypsin was deactivated by adding assay media comprised of 90% phenol-red free DMEM F12 (InVitrogen, 11039), 10% Fetal Bovine Serum (Gibco #10438-026), (5 mM Glutamax (Gibco #35050-061), 5 mM Hepes, (Gibco #15630-080), and 0.5 mg/ml Geneticin (Gibco #10131-027). Suspended cells were spun down at 300 g for 5 min, the supernatant was removed and the cell pellet was suspended in warm media (30-37° C.) comprised as above at (1e6 cell/ml).

Assay plates were prepared by adding 250 nL of compound stock solution in 100% DMSO to each well, followed by dispensing 20 microliters/well cell suspension to deliver 15-20 k cell/well. Cells were incubated for 1 hour at 37° C. Then, 5 μL of 1.5 μM or 1 μM of Thapsigargin (final concentration: 200-300 nM) was added to each well of cells. Assay plates containing cells were incubated for 14-18 hours at 37° C.

The measurement of luciferase produced by the ATF4 constructs was measured as follows. Aliquots of the Nano-Glo reagent (Nano-Glo® Luciferase Assay Substrate, Promega, N113, Nano-Glo® Luciferase Assay Buffer, Promega, N112 (parts of Nano-Glo® Luciferase Assay System, N1150) were brought to room temperature, the substrate and buffer were mixed according to manufacturer's instructions. The cell plates were equilibrated to room temperature. 25 microliters/well of the mixed Nano-Glo reagent were dispensed into assay wells and pulse spun to settle contents and the plate was sealed with film. The plates were incubated at room temperature for 1 hour before detecting luminescence on an Envision plate reader.

Example 84—Capsule Composition

An oral dosage form for administering the present invention is produced by filing a standard two piece hard gelatin capsule with the ingredients in the proportions shown in Table 2, below.

TABLE 13

| INGREDIENTS | AMOUNTS |
| --- | --- |
| 2-(4-chlorophenoxy)-N-((1-(2-(4-chlorophenoxy)acetyl)pyrrolidin-3-yl)methyl)acetamide (Compound of Example 1) | 7 mg |
| Lactose | 53 mg |
| Talc | 16 mg |
| Magnesium Stearate | 4 mg |

Example 85—Injectable Parenteral Composition

An injectable form for administering the present invention is produced by stirring 1.7% by weight of 2-(4-chlorophenoxy)-N-((1-(2-(4-chlorophenoxy)ethyl)pyrrolidin-3-yl)methyl)acetamide (Compound of Example 2) in 10% by volume propylene glycol in water.

Example 86 Tablet Composition

The sucrose, calcium sulfate dihydrate and an ATF4 pathway inhibiting compound as shown in Table 3 below, are mixed and granulated in the proportions shown with a 10% gelatin solution. The wet granules are screened, dried, mixed with the starch, talc and stearic acid, screened and compressed into a tablet.

TABLE 14

| INGREDIENTS | AMOUNTS |
| --- | --- |
| 2-(4-chlorophenoxy)-N-((1-(2-(4-chlorophenoxy)ethyl)-5-oxopyrrolidin-3-yl)methyl)acetamide (Compound of Example 3) | 12 mg |
| calcium sulfate dehydrate | 30 mg |
| Sucrose | 4 mg |
| Starch | 2 mg |
| Talc | 1 mg |
| stearic acid | 0.5 mg |

Biological Activity

Compounds of the invention are tested for activity against ATF4 translation in the above assay.

The compounds of Examples 2, 3, 4, 8, 14, 15, 22, 23, 27, 28, 32, 35, 37, 38, 40, 43, 44, 45, 47, 48, 51, 52, 55, 57, 59, 61, 62, 68, 69, 72, 73, 74, 76, 77, 78, 79, 80, and 82 were tested generally according to the above ATF4 cell based assay and in a set of two or more experimental runs exhibited an average ATF4 pathway inhibitory activity (IC$_{50}$)<100 nM.

The compounds of Examples 1, 9, 16, 18, 21, 24, 25, 29, 30, 31, 33, 34, 36, 39, 41, 42, 46, 49, 50, 53, 54, 56, 58, 60, 63, 64, 65, 66, 67, 70, 71, 75, and 81 were tested generally according to the above ATF4 cell based assay and in a set of two or more experimental runs exhibited an average ATF4 pathway inhibitory activity (IC$_{50}$) between 101 and 1,000 nM.

The compounds of Examples 6, 7, 10, 11, 12, 13, 17, 19, 20 and 26 were tested generally according to the above ATF4 cell based assay and in a set of two or more experimental runs exhibited an average ATF4 pathway inhibitory activity (IC$_{50}$) between 1,001 and 10,000 nM.

The compound of Example 25 was tested generally according to the above ATF4 cell based assay and in a set of two or more experimental runs exhibited an average ATF4 pathway inhibitory activity (IC$_{50}$) of 480.77 nM.

The compound of Example 30 was tested generally according to the above ATF4 cell based assay and in a set of two or more experimental runs exhibited an average ATF4 pathway inhibitory activity (IC$_{50}$) of 252.4 nM.

The compound of Example 37 was tested generally according to the above ATF4 cell based assay and in a set of two or more experimental runs exhibited an average ATF4 pathway inhibitory activity (IC$_{50}$) of 69.5 nM.

The compound of Example 41 was tested generally according to the above ATF4 cell based assay and in a set of two or more experimental runs exhibited an average ATF4 pathway inhibitory activity (IC$_{50}$) of 772.2 nM.

The compound of Example 48 was tested generally according to the above ATF4 cell based assay and in a set of two or more experimental runs exhibited an average ATF4 pathway inhibitory activity (IC$_{50}$) of 17 nM.

The compound of Example 54 was tested generally according to the above ATF4 cell based assay and in a set of two or more experimental runs exhibited an average ATF4 pathway inhibitory activity (IC$_{50}$) of 309.3 nM.

The compound of Example 59 was tested generally according to the above ATF4 cell based assay and in a set of two or more experimental runs exhibited an average ATF4 pathway inhibitory activity (IC$_{50}$) of 19 nM.

The compound of Example 64 was tested generally according to the above ATF4 cell based assay and in a set of two or more experimental runs exhibited an average ATF4 pathway inhibitory activity (IC$_{50}$) of 127 nM.

The compound of Example 68 was tested generally according to the above ATF4 cell based assay and in a set of two or more experimental runs exhibited an average ATF4 pathway inhibitory activity (IC$_{50}$) of 14.3 nM.

The compound of Example 71 was tested generally according to the above ATF4 cell based assay and in a set of two or more experimental runs exhibited an average ATF4 pathway inhibitory activity (IC$_{50}$) of 136.5 nM.

The compound of Example 77 was tested generally according to the above ATF4 cell based assay and in a set of two or more experimental runs exhibited an average ATF4 pathway inhibitory activity (IC$_{50}$) of 65 nM.

REFERENCES

1. Wek R C, Jiang H-Y, Anthony T G. *Coping with stress: eIF2 kinases and translational control. Biochem. Soc. Trans.* 2006 February; 34 (Pt I):7-11.
2. Hinnebusch A G, Lorsch J R. *The mechanism of eukaryotic translation initiation: new insights and challenges. Cold Spring Harb Perspect Biol.* 2012; 4(10).
3. Krishnamoorthy T, Pavitt G D, Zhang F, Dever T E, Hinnebusch A G. *Tight binding of the phosphorylated alpha subunit of initiation factor 2 (eIF2alpha) to the regulatory subunits of guanine nucleotide exchange factor eIF2B is required for inhibition of translation initiation. Mol Cell Biol.* 2001 August; 21(15):5018-30.
4. Hinnebusch A G. *Translational regulation of GCN4 and the general amino acid control of yeast. Annu. Rev. Microbiol.* 2005; 59:407-50.
5. Jackson R J, Hellen C U T, Pestova T V. *The mechanism of eukaryotic translation initiation and principles of its regulation. Nat Rev Mol Cell Biol.* 2010 February I; I 1(2):113-27.
6. Harding H P, Novoa I, Zhang Y, Zeng H, Wek R, Schapira M, et al. *Regulated translation initiation controls stress-* induced gene expression in mammalian cells. *Mol. Cell.* 2000 November; 6(5):1099-108.
7. Palam L R, Baird T D, Wek R C. *Phosphorylation of eIF2 facilitates ribosomal bypass of an inhibitory upstream ORF to enhance CHOP translation. Journal of Biological Chemistry.* 2011 April I; 286(13):10939-49.
8. Vattem K M, Wek R C. *Reinitiation involving upstream ORFs regulates ATF4 mRNA translation in mammalian cells. Proc Natl Acad Sci USA.* 2004 Aug. 3; 101(31): 11269-74.
9. Ma Y, Brewer J W, Diehl J A, Hendershot L M. *Two distinct stress signaling pathways converge upon the CHOP promoter during the mammalian unfolded protein response. J. Mol. Biol.* 2002 May 17; 318(5):1351-65.
10. Pavitt G D, Ron D. *New insights into translational regulation in the endoplasmic reticulum unfolded protein response. Cold Spring Harb Perspect Biol.* 2012 June; 4(6).
11. Ron D, Walter P. *Signal integration in the endoplasmic reticulum unfolded protein response. Nat Rev Mol Cell Biol.* 2007 July; 8(7):519-29.
12. Gardner B M, Walter P. *Unfolded proteins are Irel-activating ligands that directly induce the unfolded protein response. Science.* 2011 Sep. 30; 333(6051):1891-4.
13. Harding H P, Zhang Y, Bertolotti A, Zeng H, Ron D. *Perk is essential for translational regulation and cell survival during the unfolded protein response. Mol Cell.* 2000 May; 5(5):897-904.
14. Walter P, Ron D. *The unfolded protein response: from stress pathway to homeostatic regulation. Science.* 2011 Nov. 25; 334(6059):1081-6.
15. Tabas I, Ron D. *Integrating the mechanisms of apoptosis induced by endoplasmic reticulum stress. Nat Cell Biol.* 2011 March I; 13(3):184-90.
16. Shore G C G, Papa F R F, Oakes S A S. *Signaling cell death from the endoplasmic reticulum stress response. Current Opinion in Cell Biology.* 2011 April I; 23(2):143-9.
17. Bi M, Naczki C, Koritzinsky M, Fels D, 174 WO 2014/144952 PC T/US2014/029568 Blais J, Hu N, Harking H, Novoa I, Varia M, Raleigh J, Scheuner D, Kaufman R J, Bell J, Ron D, Wouters B G, Koumenis C. 2005. *ER stress-regulated translation increases tolerance to extreme hypoxia and promotes tumor growth. EMBO J.* 24:3470-3481.
18. Bobrovnikova-Marjon E, Pytel D, Vaites L P, Singh N, Koretzky G A, Diehl J A. 2010. *PERK promotes cancer cell proliferation and tumor growth by limiting oxidative DNA damage. Oncogene* 29: 3881-3895.
19. Avivar-Valderas A, Bobrovnikova-Marjon E, Diehl A, Nagi C, Debnath J, Aguirre-Guiso JA 2011. *PERK integrates autophagy and oxidative stress responses to promote survival during extracellular matrix detachment. Mol Cel Biol* 31:3616-3629.
20. Axten J M., Medina J. R., Feng Y., Shu A., Romeril S. P. et al. 2012. *Discovery of 7-methy-5(1-([3-10 (trifluoromethyl)phenyl]acetyl)-2, 3-dihydro-1H-indol-5yl)-7H-pyrrolo [2,3-d]pyrimidin-4 amine (GSK2606414), a potent and selective first-in class inhibitor of protein kinase R (PKR)-like endplasmic reticulum kinase (PERK). J. Med. Chem.* 55(16):7193-7207
21. Ye J. Kumanova M., Hart L. S., Sloane K., Zhang H. et al. 2010. *The GCN2-ATF4 pathway is critical for tumour cell survival and proliferation in response to nutrient deprivation. EMBO J.* 29: 2082-2096.
22. Moreno J A, Radford H, Peretti D, Steinert J R, Verity N, Martin M G, Halliday M, Morgan J, Dinsdale D, Ortori C A, Barrett D A, Tsaytler P, Bertolotti A, Willis A E, Bushell M, Mallucci G R. 2012. *Sustained translational repression by eIF2n-P mediates prion neurodegeneration. Nature* 485:507-511.
23. Pavitt G D and Proud C G. 2009. *Protein synthesis and its control in neuronal cells with a focus on vanishing white matter disease. Biochem Soc Trans* 37:1298-20 1310.
24. Costa-Mattioli M. Gobert D., Harding H., Herdy B. Azzi M., Bruno M. et al, 2005. *Translational control of hippocampal synaptic plasticity and memory by the eIF2n kinase GCN2. Nature* 436:1166-1173.
25. Costa-Mattioli M., Gobert D., Stern E., Garnache K., Colina R I, Cuello C., Sossin W., Kaufman R., Pelletier J., Rosenblum et al. 2007. *eIF2n phosphorylation bidirectionally regulates the switch from short to long term synaptic plasticity and memory. Cell* 25 129: 195-206.
26. Zhu P. J, Huan W., Kalikulov D., Yoo J. W., Placzek A. N., Stoica L, Zhou H., Bell J. C., Frielander M. J., Krnjevic K., Noebels J. L., Costa-Mattioli M. 2011. *Suppression of PKR promotes network excitability and enhanced cognition by interferon-7-mediated disinhibition. Cell* 147: 1384-1396.
27. Borck G., Shin B. S., Stiller B., et al 2012. *eIF2γ mutation that disrupts eIF2 complex integrity links intellectual disability to impaired translation* 30 *initiation. Mol Cell* 48:1-6.
28. Zeenko V. V., Wang C, Majumder M, Komar A. A., Snider M. D., Merrick W. C., Kaufman R. J. and Hatzoglou M. (2008). *An efficient in vitro translation system from mammalian cell lacking translational inhibition caused by eIF2 phosphorylation. RNA* 14: 593-602.
29. Mikami S., Masutani M., Sonenber N., Yokoyama S. And Imataka H. 175 WO 2014/144952 PC T/US2014/ 029568 2006. *An efficient mammalian cell-free translation system supplemented with translation factors. Protein Expr. Purif.* 46:348-357.

While the preferred embodiments of the invention are illustrated by the above, it is to be understood that the invention is not limited to the precise instructions herein disclosed and that the right to all modifications coming within the scope of the following claims is reserved.

What is claimed is:
1. A method of treating a disease selected from Alzheimer's disease, spinal cord injury, traumatic brain injury, ischemic stroke, stroke, diabetes, Parkinson disease, Huntington's disease, Creutzfeldt-Jakob Disease, and related prion diseases, progressive supranuclear palsy, amyotrophic lateral sclerosis, myocardial infarction, cardiovascular disease, inflammation, fibrosis, chronic and acute diseases of the liver, chronic and amuicute diseases of the lung, chronic and acute diseases of the kidney, chronic traumatic encephalopathy (CTE), neurodegeneration, dementia, cognitive impairment, atherosclerosis, ocular diseases, in organ transplantation and arrhythmias, in a mammal in need thereof, which comprises administering to such mammal a therapeutically effective amount of a compound represented by the following Formula:

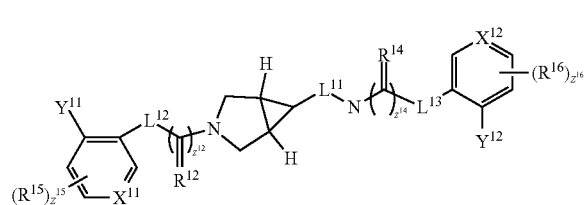

wherein:
X$^{11}$ and X$^{12}$ are independently —CH— or —N—;
L$^{12}$ and L$^{13}$ are independently: —NH—, —N(CH$_3$)—, —NH—CH$_2$—, —CH$_2$—C(O)—NH—, —NH—C(O)—CH$_2$—, —CH$_2$—O—, —CH$_2$—CH$_2$—O—, —CH$_2$—CH$_2$—CH$_2$—O—; —O—CH$_2$—, —O—CH$_2$—CH$_2$— or —O—CH$_2$—CH$_2$—CH$_2$—;
L$^{11}$ is selected from: a bond, —O—, —CH$_2$—, —CH$_2$—CH$_2$—, and —CH$_2$—CH$_2$—CH$_2$—;
Y$^{11}$ is hydrogen or is C$_{1-2}$alkyl and taken together with L$^{12}$ to form piperidinyl, tetrahydrofuranyl or tetrahydropyranyl;
Y$^{12}$ is hydrogen or is C$_{1-2}$alkyl and taken together with L$^{13}$ to form tetrahydrofuranyl or tetrahydropyranyl;
R$^{11}$ is selected from: hydrogen, methyl, fluoro, —OH;
R$^{15}$ and R$^{16}$ are independently hydrogen, —CH$_3$—, —OCH$_3$—, —CF$_3$—, fluoro or chloro;
R$^{12}$ and R$^{14}$ are O;
z$^{12}$ and z$^{14}$ are independently 0 or 1; and
z$^{15}$ and z$^{16}$ are independently an integer from 0 to 2;
or a salt thereof including a pharmaceutically acceptable salt thereof.

2. The method of claim 1, wherein the mammal is a human.

3. The method of inhibiting the ATF4 pathway in a mammal in need thereof, which comprises administering to such mammal a therapeutically effective amount of a compound represented by the following Formula:

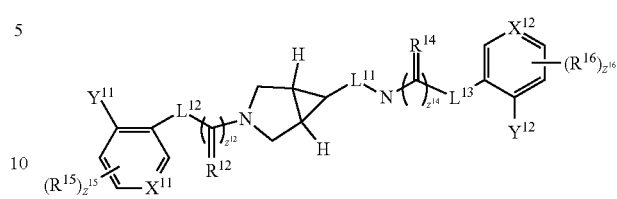

wherein:
X$^{11}$ and X$^{12}$ are independently —CH— or —N—;
L$^{12}$ and L$^{13}$ are independently: —NH—, —N(CH$_3$)—, —NH—CH$_2$—, —CH$_2$—C(O)—NH—, —NH—C(O)—CH$_2$—, —CH$_2$—O—, —CH$_2$—CH$_2$—O—, —CH$_2$—CH$_2$—CH$_2$—O—; —O—CH$_2$—, —O—CH$_2$—CH$_2$— or —O—CH$_2$—CH$_2$—CH$_2$—;
L$^{11}$ is selected from: a bond, —O—, —CH$_2$—, —CH$_2$—CH$_2$—, and —CH$_2$—CH$_2$—CH$_2$—;
Y$^{11}$ is hydrogen or is C$_{1-2}$alkyl and taken together with L$^{12}$ to form piperidinyl, tetrahydrofuranyl or tetrahydropyranyl;
Y$^{12}$ is hydrogen or is C$_{1-2}$alkyl and taken together with L$^{13}$ to form tetrahydrofuranyl or tetrahydropyranyl;
R$^{11}$ is selected from: hydrogen, methyl, fluoro, —OH;
R$^{15}$ and R$^{16}$ are independently hydrogen, —CH$_3$—, —OCH$_3$—, —CF$_3$—, fluoro or chloro;
R$^{12}$ and R$^{14}$ are O;
z$^{12}$ and z$^{14}$ are independently 0 or 1; and
z$^{15}$ and z$^{16}$ are independently an integer from 0 to 2;
or a salt thereof including a pharmaceutically acceptable salt thereof.

4. The method of claim 3, wherein the mammal is a human.

* * * * *